United States Patent
Yano et al.

(10) Patent No.: US 10,865,344 B2
(45) Date of Patent: Dec. 15, 2020

(54) LOW MOLECULAR WEIGHT POLAR COMPOUND FOR HOMOGENEOUSLY ALIGNING LIQUID CRYSTAL MEDIUM, AND LIQUID CRYSTAL MEDIUM CONTAINING SAME

(71) Applicants: JNC CORPORATION, Tokyo (JP); JNC PETROCHEMICAL CORPORATION, Tokyo (JP)

(72) Inventors: Tomohiro Yano, Chiba (JP); Fumitaka Kondou, Chiba (JP); Shin-ichi Yamamoto, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 95 days.

(21) Appl. No.: 16/300,958

(22) PCT Filed: Feb. 24, 2017

(86) PCT No.: PCT/JP2017/007041
§ 371 (c)(1),
(2) Date: Nov. 13, 2018

(87) PCT Pub. No.: WO2017/199512
PCT Pub. Date: Nov. 23, 2017

(65) Prior Publication Data
US 2019/0367813 A1 Dec. 5, 2019

(30) Foreign Application Priority Data

May 18, 2016 (JP) .................. 2016-099756
Sep. 21, 2016 (JP) .................. 2016-183559

(51) Int. Cl.
| | | |
|---|---|---|
| *G02F 1/1333* | (2006.01) | |
| *C09K 19/56* | (2006.01) | |
| *C07C 69/18* | (2006.01) | |
| *C07C 69/54* | (2006.01) | |
| *C07C 229/30* | (2006.01) | |
| *C09K 19/30* | (2006.01) | |
| *C09K 19/34* | (2006.01) | |
| *C09K 19/54* | (2006.01) | |
| *C09K 19/04* | (2006.01) | |

(52) U.S. Cl.
CPC ............ *C09K 19/56* (2013.01); *C07C 69/18* (2013.01); *C07C 69/54* (2013.01); *C07C 229/30* (2013.01); *C09K 19/3001* (2013.01); *C09K 19/3003* (2013.01); *C09K 19/3066* (2013.01); *C09K 19/3068* (2013.01); *C09K 19/3402* (2013.01); *C09K 19/542* (2013.01); *C09K 2019/0466* (2013.01); *C09K 2019/301* (2013.01); *C09K 2019/3004* (2013.01); *C09K 2019/308* (2013.01); *C09K 2019/3016* (2013.01); *C09K 2019/3077* (2013.01); *C09K 2019/3083* (2013.01); *C09K 2019/3422* (2013.01); *C09K 2019/548* (2013.01)

(58) Field of Classification Search
CPC ............... C09K 19/56; C09K 19/3001; C09K 19/3003; C09K 19/3066; C09K 19/3068; C09K 19/3402; C09K 19/542; C09K 2019/0466; C09K 2019/3004; C09K 2019/301; C09K 2019/3016; C09K 2019/3077; C09K 2019/308; C09K 2019/3083; C09K 2019/3422; C09K 2019/548; G02F 1/1333; C07C 69/18; C07C 69/54; C07C 229/30
USPC .......................................... 252/299.4
See application file for complete search history.

(56) References Cited

U.S. PATENT DOCUMENTS

| | | |
|---|---|---|
| 5,384,067 A | 1/1995 | Doane et al. |
| 10,392,339 B2 | 8/2019 | Tanaka et al. |
| 10,442,992 B2 | 10/2019 | Saito et al. |
| 2013/0182202 A1 | 7/2013 | Graziano et al. |
| 2013/0314655 A1 | 11/2013 | Archetti et al. |
| 2016/0075950 A1 | 3/2016 | Kobayashi et al. |
| 2019/0292455 A1 | 9/2019 | Yano et al. |
| 2019/0367813 A1* | 12/2019 | Yano .............. C09K 19/20 |

FOREIGN PATENT DOCUMENTS

| | | |
|---|---|---|
| JP | H07507083 | 8/1995 |
| JP | 2003287755 | 10/2003 |
| JP | 2005128201 | 5/2005 |
| JP | 2013543526 | 12/2013 |
| JP | 2014037366 | 2/2014 |
| JP | 2014513150 | 5/2014 |
| JP | 2014196434 | 10/2014 |
| JP | 2015125151 | 7/2015 |
| JP | 6070973 | 2/2017 |
| WO | 9323496 | 11/1993 |
| WO | 2014094959 | 6/2014 |

(Continued)

OTHER PUBLICATIONS

"International Search Report (Form PCT/ISA/210) of PCT/JP2017/007042" dated Apr. 25, 2017, with English translation thereof, pp. 1-6.

(Continued)

*Primary Examiner* — Geraldina Visconti
(74) *Attorney, Agent, or Firm* — JCIPRNET

(57) ABSTRACT

A liquid crystal composition without requiring an alignment film or alignment treatment on a substrate. The problem is solved by a low molecular weight polar compound capable of homogeneously aligning a liquid crystal medium relative to the substrate, for example, a low molecular weight polar compound represented by formula (1):

M-P   (1)

In formula (1), M is a nonpolar group having 1 or more carbons, and P is a polar group.

12 Claims, 1 Drawing Sheet

(56) References Cited

FOREIGN PATENT DOCUMENTS

| WO | 2014174929 | 10/2014 |
|----|------------|---------|
| WO | 2014192657 | 12/2014 |
| WO | 2017199512 | 11/2017 |
| WO | 2017199513 | 11/2017 |
| WO | 2017199514 | 11/2017 |

OTHER PUBLICATIONS

"International Search Report (Form PCT/ISA/210) of PCT/JP2017/007043", dated May 9, 2017, with English translation thereof, pp. 1-4.
"Office Action of Japan Related Application, application No. 2018-518099", dated Jul. 9, 2019, with English translation thereof, p. 1-p. 6.
Office Action of Japan Counterpart Application, with English translation thereof, dated Feb. 25, 2019, pp. 1-5.
"Office Action of Japan Related Application No. 2018-518098", with English translation thereof, dated Mar. 3, 2019, pp. 1-4.
"Decision to Grant a Patent of Japanese Counterpart Application," dated Aug. 13, 2019, with English translation thereof, pp. 1-5.
"Invitation pursuant to Rule 62a(1) EPC of Europe Counterpart Application", dated Nov. 29, 2019, p. 1-p. 2.
"Office Action of Japan Counterpart Application, application No. 2018-518097", dated Sep. 10, 2019, with English translation thereof, p. 1-p. 12.
"Office Action of Japan Related Application, application No. 2018-518098", dated Sep. 10, 2019, with English translation thereof, p. 1-p. 10.
Osamu Haba et al., "UV-Induced Stable Planar Alignment of Nematic Liquid Crystals Using a Polypropyleneimine Dendrimer Having a Mesogen Consisting of Cinnamate and Azobenzene Moieties", Molecular Crystals and Liquid Crystals, Jul. 2015, pp. 201-209.
Il Hwa Jeong et al., "Novel Approach to Achieve Conventional Polyimide-less IPS/FFS LCDs", SID 2014 Digest, Jun. 2014, pp. 1418-1420.
"International Search Report (Form PCT/ISA/210) of PCT/JP2017/007041," dated Apr. 25, 2017, with English translation thereof, pp. 1-6.
Office Action of Japan Counterpart Application, with English translation thereof, dated Jan. 28, 2020, pp. 1-6.
"Office Action of Japan Related Application No. 2018-518098", with English translation thereof, dated Jan. 28, 2020, pp. 1-6.
"Office Action of Related U.S. Appl. No. 16/301,444", dated Jan. 27, 2020, pp. 1-6.
"Search Report of Europe Counterpart Application", dated Mar. 31, 2020, pp. 1-19.
"Office Action of Related U.S. Appl. No. 16/301,446", dated Apr. 17, 2018, pp. 1-38.
"Notice of Allowance of Related U.S. Appl. No. 16/301,444,", dated Apr. 29, 2020, pp. 1-13.

\* cited by examiner

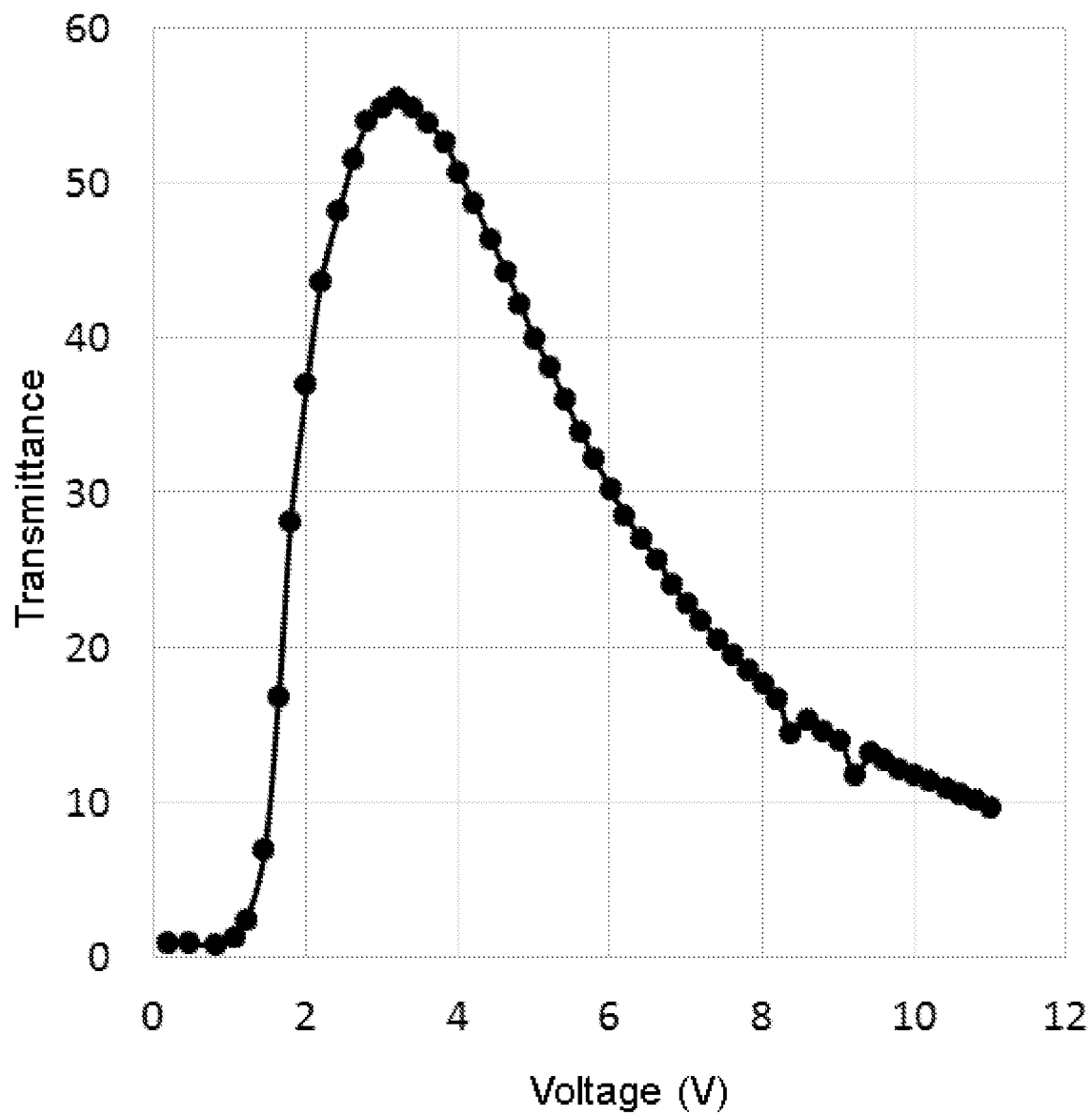

LOW MOLECULAR WEIGHT POLAR COMPOUND FOR HOMOGENEOUSLY ALIGNING LIQUID CRYSTAL MEDIUM, AND LIQUID CRYSTAL MEDIUM CONTAINING SAME

CROSS-REFERENCE TO RELATED APPLICATION

This application is a 371 application of International PCT application serial no. PCT/JP2017/007041, filed on Feb. 24, 2017, which claims the priority benefits of Japan application no. 2016-099756, filed on May 18, 2016, and Japan application no. 2016-183559, filed on Sep. 21, 2016. The entirety of each of the abovementioned patent applications is hereby incorporated by reference herein and made a part of this specification.

TECHNICAL FIELD

The invention relates to a low molecular weight polar compound (hereinafter, also referred to merely as "polar compound") for homogeneously aligning a liquid crystal medium relative to a substrate and a liquid crystal medium containing the low molecular weight polar compound.

BACKGROUND ART

In a liquid crystal display device, a liquid crystal medium in a liquid crystal cell is aligned by providing an alignment film on a substrate or applying alignment treatment (polarized UV irradiation, rubbing or the like) onto the substrate.

On the other hand, a report has been made on a technology on aligning the liquid crystal medium by adding a polar compound or the like to the liquid crystal medium even without applying such alignment treatment (Patent literature No. 1). A matter reported therein is the technology on causing homeotropic alignment (vertical alignment).

Meanwhile, specific examples of the technology for homogeneously aligning the liquid crystal medium include a technology of using a polymerizable dendrimer having an azobenzene skeleton (Non-patent literature No. 1) and a technology of using a polymerizable compound (Non-patent literature No. 2), in which the technologies require the alignment treatment such as polarized UV irradiation and rubbing, although the alignment film is not used.

CITATION LIST

Patent Literature

Patent literature No. 1: JP 2013-543526 A.
Patent literature No. 2: JP 2003-287755 A.

Non-Patent Literature

Non-patent literature No. 1: Mol. Cryst. Liq. Cryst., Volume 610, Issue 1, 2015, Page 201-209
Non-patent literature No. 2: Society for Information Display International Symposium (2014), 45(1), 1418-1420

SUMMARY OF INVENTION

Technical Problem

The invention has been made in view of the situation described above, and an object of the invention is to provide a low molecular weight polar compound capable of homogeneously aligning a liquid crystal medium relative to a substrate without requiring an alignment film or alignment treatment such as polarized UV irradiation and rubbing for aligning the liquid crystal medium, which has been used so far, and a liquid crystal medium containing the low molecular weight polar compound.

Solution to Problem

The present inventors have conducted various studies in order to solve the problem, and as a result, have found that the object of the invention can be achieved by a low molecular weight polar compound formed of a nonpolar group and a polar group, preferably, having a specific structure, and thus have completed the invention.

Item 1. A liquid crystal medium to be sealed between a pair of substrates subjected to neither alignment treatment nor an alignment film and having a transparent electrode formed on at least one of the substrates, wherein the liquid crystal medium contains a low molecular weight polar compound for homogeneously aligning the liquid crystal medium relative to the substrate, so that the homogeneous alignment of the liquid crystal medium relative to the substrate can occur spontaneously.

Item 2. A low molecular weight polar compound, homogeneously aligning a liquid crystal medium relative to a substrate.

Item 3. The low molecular weight polar compound according to item 2, having a positive-phase negative-phase CV product of 1.3 or more.

Item 4. The low molecular weight polar compound according to item 2 or 3, represented by formula (2) or (3):

Formula 9

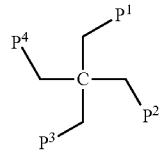

(2)

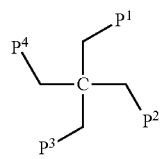

(3)

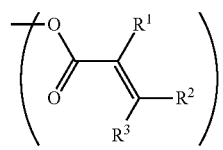

(Q-0)

wherein, in formulas (2) and (3),
$R^4$ is hydrogen, halogen or alkyl having 1 to 20 carbons, and in $R^4$, at least one piece of —$CH_2$— may be independently replaced by —O— or —S—, and at least one piece of —$(CH_2)_2$— may be replaced by —CH=CH—, and in the groups, at least one hydrogen may be replaced by halogen,
$P^1$, $P^2$, $P^3$ and $P^4$ are independently a group represented by formula (Q-0) or straight-chain, branched-chain or cyclic alkyl having 1 to 25 carbons, and in $P^1$, $P^{2s}$ $P^3$ and $P^4$, at least one piece of —$CH_2$— nonadjacent to each other may be independently replaced by —N(—$P^0$)—, —O—, —S—, —CO—, —CO—O—, —O—CO— or —O—CO—O— in such a manner that N, O and/or S atoms are not directly connected to each other, at least one tertiary carbon (CH group) may be replaced by N, at least one hydrogen may be independently replaced by F or Cl, and at least one piece of —(CH$_2$)$_2$— may be independently replaced by —CH=CH— or —C≡C—, in which P$^1$, P$^2$, P$^3$ and P$^4$ contain one or more heteroatoms selected from N, S and/or O, and P$^0$ is independently straight-chain, branched-chain or cyclic alkyl having 1 to 25 carbons, and in P$^0$, at least one piece of —CH$_2$— nonadjacent to each other may be independently replaced by —N(—P$^0$)—, —O—, —S—, —CO—, —CO—O—, —O—CO— or —O—CO—O— in such a manner that N, O and/or S atoms are not directly connected to each other, at least one tertiary carbon (CH group) may be replaced by N, at least one hydrogen may be independently replaced by F or Cl, and at least one piece of —(CH$_2$)$_2$— may be independently replaced by —CH=CH— or —C≡C—, in which P$^0$ contains one or more heteroatoms selected from N, S and/or O, and in formula (Q-0), R$^1$, R$^2$ and R$^3$ are independently hydrogen, halogen or alkyl having 1 to 20 carbons, and in R$^1$, R$^2$ and R$^3$, at least one piece of —CH$_2$— may be independently replaced by —O— or —S—, and at least one piece of —(CH$_2$)$_2$— may be replaced by —CH=CH—, and in the groups, at least one hydrogen may be replaced by halogen.

Item 5. A liquid crystal composition, containing at least one low molecular weight polar compound according to any one of items 2 to 4.

Item 6. The liquid crystal composition according to item 5, wherein a total positive-phase negative-phase CV product, which is a product of the positive-phase negative-phase CV product and a content of the low molecular weight polar compound, is 0.01 or more.

Item 7. The liquid crystal composition according to item 6, wherein a ratio (total positive-phase negative-phase CV product/surface free energy (N/m)) of the total positive-phase negative-phase CV product to surface free energy of the substrate is 0.025 to 1.

Item 8. The liquid crystal composition according to any one of items 5 to 7, further containing at least one liquid crystal compound represented by any one of formulas (5) to (7):

Formula 10

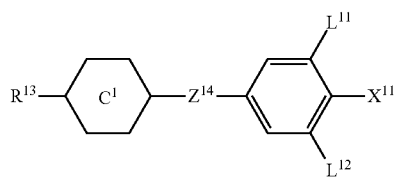

(5)

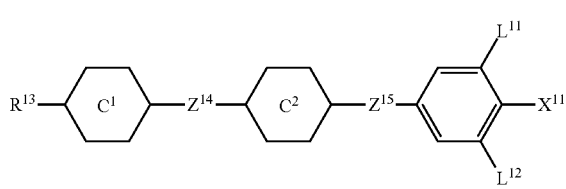

(6)

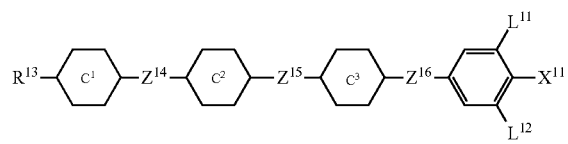

(7)

wherein, in formulas (5) to (7),

R$^{13}$ is alkyl having 1 to 10 carbons or alkenyl having 2 to 10 carbons, and in R$^{13}$, at least one piece of —CH$_2$— may be replaced by —O—, and at least one hydrogen may be replaced by fluorine;

X$^{11}$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$;

ring C$^1$, ring C$^2$ and ring C$^3$ are independently 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;

Z$^{14}$, Z$^{15}$ and Z$^{16}$ are independently a single bond, —(CH$_2$)$_2$—, —CH=CH—, —C≡C—, —COO—, —CF$_2$O—, —OCF$_2$—, —CH$_2$O— or —(CH$_2$)$_4$—; and L$^{11}$ and L$^{12}$ are independently hydrogen or fluorine.

Item 9. The liquid crystal composition according to any one of items 5 to 8, further containing a liquid crystal compound represented by formula (8):

Formula 11

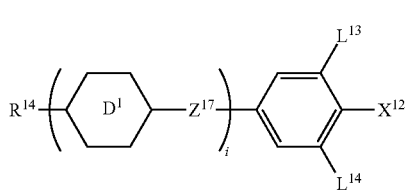

(8)

wherein, in formula (8),

R$^{14}$ is alkyl having 1 to 10 carbons or alkenyl having 2 to 10 carbons, and in R$^{14}$, at least one piece of —CH$_2$— may be replaced by —O—, and at least one hydrogen may be replaced by fluorine;

X$^{12}$ is —C≡N or —C≡C—C≡N;

ring D$^1$ is 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;

Z$^{17}$ is a single bond, —(CH$_2$)$_2$—, —C≡C—, —COO—, —CF$_2$O—, —OCF$_2$— or —CH$_2$O—;

L$^{13}$ and L$^{14}$ are independently hydrogen or fluorine; and i is 1, 2, 3 or 4.

Item 10. The liquid crystal composition according to any one of items 5 to 9, further containing at least one liquid crystal compound represented by any one of formulas (16) to (18):

Formula 12

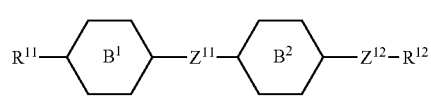

(16)

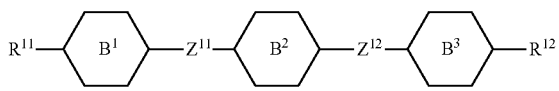

(17)

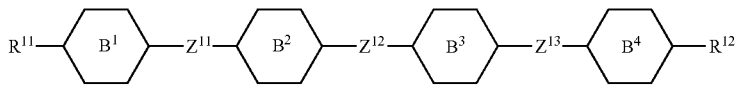

(18)

wherein, in formulas (16) to (18), $R^{11}$ and $R^{12}$ are independently alkyl having 1 to 10 carbons, alkoxy having 1 to 10 carbons, alkoxyalkyl having 2 to 10 carbons, alkenyl having 2 to 10 carbons or difluorovinyl;

ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and $Z^{11}$, $Z^{12}$ and $Z^{13}$ are independently a single bond, —(CH$_2$)$_2$—, —CH=CH—, —C≡C— or —COO—.

Item 11. The liquid crystal composition according to any one of items 5 to 10, further containing a polymerizable compound represented by formula (19):

Formula 13

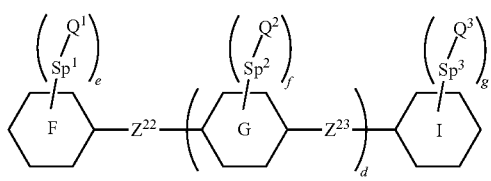

(19)

wherein, in formula (19), ring F and ring I are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one hydrogen may be independently replaced by halogen, alkyl having 1 to 12 carbons, alkoxy having 1 to 12 carbons, or alkyl having 1 to 12 carbons in which at least one hydrogen is replaced by halogen;

ring G is 1,4-cyclohexylene, 1,4-cyclohexenylene, 1,4-phenylene, naphthalene-1,2-diyl, naphthalene-, 3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one hydrogen may be independently replaced by halogen, alkyl having 1 to 12 carbons, alkoxy having 1 to 12 carbons, or alkyl having 1 to 12 carbons in which at least one hydrogen is replaced by halogen;

$Z^{22}$ and $Z^{23}$ are independently a single bond or alkylene having 1 to 10 carbons, and in $Z^{22}$ and $Z^{23}$, at least one piece of —CH$_2$— may be independently replaced by —O—, —CO— or —COO—, and at least one piece of —CH$_2$CH$_2$— may be independently replaced by —CH=CH—, —C(CH$_3$)=CH— or —C(CH$_3$)=C(CH$_3$)—, and in the groups, at least one hydrogen may be replaced by fluorine or chlorine;

$Q^1$, $Q^2$ and $Q^3$ are independently a polymerizable group;

$Sp^1$, $Sp^2$ and $Sp^3$ are independently a single bond or alkylene having 1 to 10 carbons, and in $Sp^1$, $Sp^2$ and $Sp^3$, at least one piece of —CH$_2$— may be independently replaced by —O—, —COO—, —OCO— or —OCOO—, and at least one piece of —CH$_2$CH$_2$— may be independently replaced by —CH=CH— or —C≡C—, and in the groups, at least one hydrogen may be independently replaced by fluorine or chlorine;

d is 0, 1 or 2; and e, f and g are independently 0, 1, 2, 3 or 4, and a sum of e, f and g is 1 or more.

Item 12. The liquid crystal composition according to item 11, wherein, in formula (19), $Q^1$, $Q^2$ and $Q^3$ are independently a polymerizable group represented by any one of formulas (Q-1) to (Q-5):

Formula 14

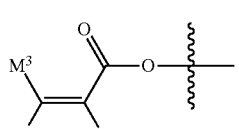

(Q-1)

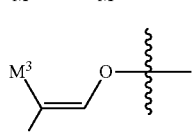

(Q-2)

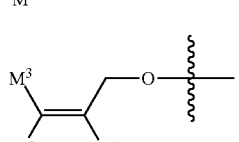

(Q-3)

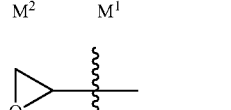

(Q-4)

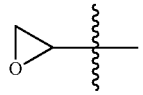

(Q-5)

wherein, in formulas (Q-1) to (Q-5), $M^1$, $M^2$ and $M^3$ are independently hydrogen, fluorine, alkyl having 1 to 5 carbons, or alkyl having 1 to 5 carbons in which at least one hydrogen is replaced by halogen.

Item 13. The liquid crystal composition according to item 11, wherein the polymerizable compound represented by formula (19) is a polymerizable compound represented by any one of formulas (19-1) to (19-7):

Formula 15

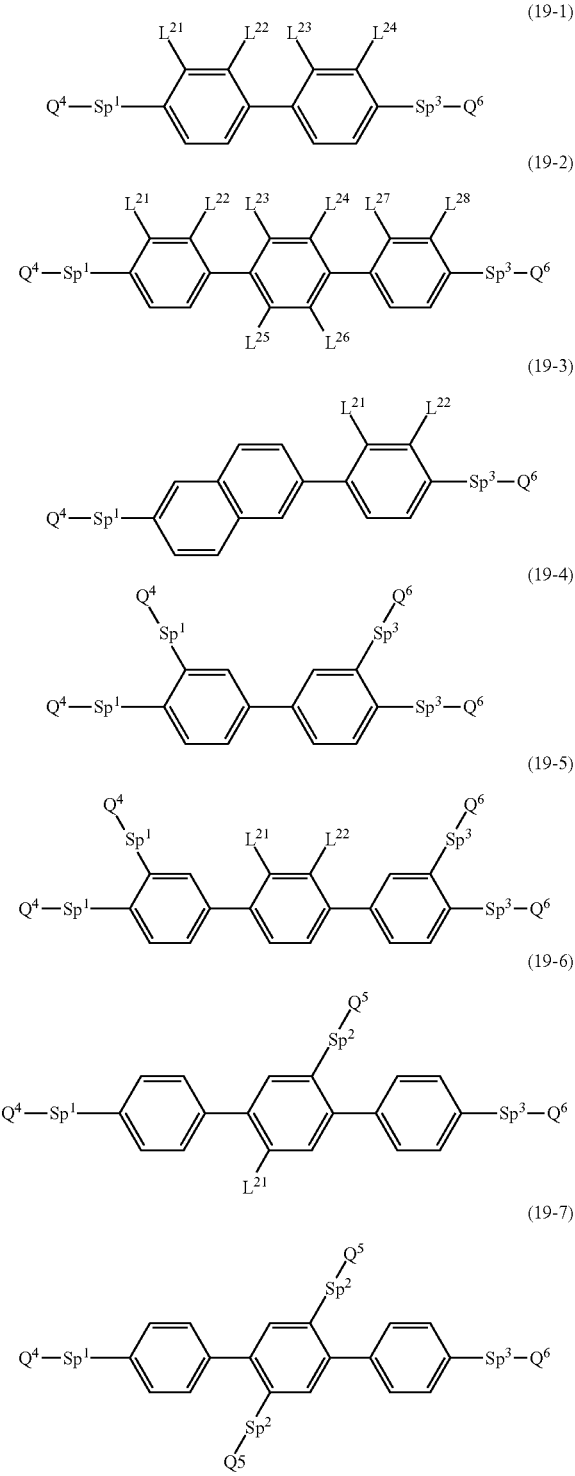

wherein, in formulas (19-1) to (19-7), $L^{21}$, $L^{22}$, $L^{23}$, $L^{24}$, $L^{25}$, $L^{26}$, $L^{27}$ and $L^{28}$ are independently hydrogen, fluorine or methyl;

$Sp^1$, $Sp^2$ and $Sp^3$ are independently a single bond or alkylene having 1 to 10 carbons, and in $Sp^1$, $Sp^2$ and $Sp^3$, at least one piece of —CH$_2$— may be independently replaced by —O—, —COO—, —OCO— or —OCOO—, and at least one piece of —(CH$_2$)$_2$— may be independently replaced by —CH=CH— or —C≡C—, and in the groups, at least one hydrogen may be independently replaced by fluorine or chlorine; and $Q^4$, $Q^5$ and $Q^6$ are independently a polymerizable group represented by any one of formulas (Q-1) to (Q-3), in which $M^1$, $M^2$ and $M^3$ are independently hydrogen, fluorine, alkyl having 1 to 5 carbons, or alkyl having 1 to 5 carbons in which at least one hydrogen is replaced by halogen:

Formula 16

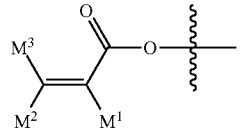

(Q-1)

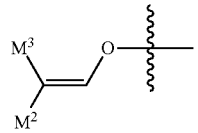

(Q-2)

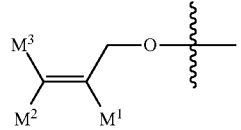

(Q-3)

Item 14. The liquid crystal composition according to any one of items 5 to 13, further containing at least one selected from a polymerization initiator, a polymerization inhibitor, an optically active compound, an antioxidant, an ultraviolet light absorber, a light stabilizer, a heat stabilizer and an antifoaming agent.

Advantageous Effects of Invention

A technology capable of homogeneously aligning a liquid crystal medium by using a low molecular weight additive has not been found so far. According to preferred embodiments in the present application invention, the liquid crystal medium can be homogeneously aligned merely by adding a specific low molecular weight polar compound thereto, and a need for an alignment film or alignment treatment that has been applied so far for aligning liquid crystals can be eliminated. As a result, for example, a polyimide-less device can be achieved for a mode using a transverse electric field, such as an FFS mode.

BRIEF DESCRIPTION OF DRAWINGS

FIG. 1 shows a voltage-transmittance curve in Example 1.

DESCRIPTION OF EMBODIMENTS

Usage of terms herein is as described below. A term "liquid crystal medium" means a liquid crystal or liquid crystalline material used in a liquid crystal display device or apparatus. Although the medium is not always limited to the following, specific examples thereof include a liquid crystal compound, a liquid crystal composition and a polymer liquid crystal. Terms "liquid crystal composition" and "liquid crystal display device" may be occasionally abbreviated as "composition" and "device," respectively. A term "liquid crystal display device" is a generic term for a liquid crystal display panel and a liquid crystal display module. A term "liquid crystal compound" is a generic term for a compound having a liquid crystal phase such as a nematic phase and a smectic phase, and a compound having no liquid crystal phase but being mixed with the composition for the purpose of adjusting characteristics such as a temperature range of the nematic phase, viscosity and dielectric anisotropy. The compound has a six-membered ring such as 1,4-cyclohexylene and 1,4-phenylene and has rod-like molecular structure. A term "polymerizable compound" is a compound to be added for the purpose of forming a polymer in the composition. A term "low molecular weight compound" means a material not classified as "polymer." A term "polymer" means a material in which a compound having a structure capable of causing a polymerization reaction has a repeated structure of a monomer unit, formed by the polymerization reaction. A compound having high molecular weight that is synthesized by a reaction which is not the polymerization reaction, and has no repeated structure of the monomer unit is a low molecular weight compound. Moreover, a compound having the structure capable of causing the polymerization reaction, and the compound before polymerization is the low molecular weight compound.

The liquid crystal composition is prepared by mixing a plurality of liquid crystal compounds. A proportion (content) of the liquid crystal compound is expressed in terms of weight percent (% by weight) based on the weight of the liquid crystal composition. An additive such as a polymerizable compound, a polymerization initiator, a polymerization inhibitor, an optically active compound, an antioxidant, an ultraviolet light absorber, a light stabilizer, a heat stabilizer, an antifoaming agent and a dye is added to the liquid crystal composition, when necessary. A proportion (amount of addition) of the additive is expressed in terms of weight percent (% by weight) based on the weight of the liquid crystal composition in a manner similar to the proportion of the liquid crystal compounds. Weight parts per million (ppm) may be occasionally used. A proportion of the polymerization initiator and the polymerization inhibitor is exceptionally expressed based on the weight of the polymerizable compound.

For example, a compound represented by formula (X) means one compound, a mixture of two compounds or a mixture of three or more compounds, represented by formula (X). A symbol such as $B^1$, $C^1$ and F surrounded by a hexagonal shape corresponds to ring $B^1$, ring $C^1$ and ring F, respectively. The hexagonal shape represents a six-membered ring such as a cyclohexane ring and a benzene ring or a fused ring such as a naphthalene ring. An oblique line crossing the hexagonal shape represents that arbitrary hydrogen on the ring may be replaced by a group such as —$Sp^1$-$Q^1$. A subscript such as e represents the number of groups subjected to replacement. When the subscript is 0, such replacement is not performed.

A symbol (for example, a superscript to R) of a terminal group is used for a plurality of component compounds. In the compounds, two groups represented by two arbitrary terminal groups having the same symbol may be identical or different. For example, in one case, a terminal group of compound (Y) is ethyl, and a terminal group having the same symbol of compound (Z) is ethyl. In another case, a terminal group of compound (Y) is ethyl, and a terminal group having the same symbol of compound (Z) is propyl. A same rule applies also to a symbol of any other terminal group, a ring, a bonding group or the like. In formula (8), when i is 2, two of ring $D^1$ exists. In the compound, two groups represented by two of ring $D^1$ may be identical or different. A same rule applies also to two of arbitrary ring $D^1$ when i is larger than 2. A same rule applies also to a symbol of any other ring, a bonding group or the like.

An expression "at least one piece of 'X'" means that the number of 'X' is arbitrary. An expression "at least one piece of 'X' may be replaced by 'Y'" means that, when the number of 'X' is 1, a position of 'X' is arbitrary, and also when the number of 'X' is 2 or more, positions thereof can be selected without restriction. A same rule applies also to an expression "at least one piece of 'X' is replaced by 'Y'." An expression "at least one piece of X may be replaced by Y, Z or W" means including a case where at least one piece of X is replaced by Y, a case where at least one piece of X is replaced by Z, and a case where at least one piece of X is replaced by W, and also a case where a plurality of pieces of X are replaced by at least two pieces of Y, Z and W. For example, alkyl in which at least one piece of —$CH_2$-(or —$(CH_2)_2$—) may be replaced by —O— (or —CH=CH—) includes alkyl, alkenyl, alkoxy, alkoxyalkyl, alkoxyalkenyl and alkenyloxyalkyl. In addition, a case where two pieces of consecutive —$CH_2$— are replaced by —O— to form —O—O— is not preferred. In the liquid crystal compound, in alkyl or the like, a case where —$CH_2$— of a methyl part (—$CH_2$—H) is replaced by —O— to form —O—H is not preferred.

Halogen means fluorine, chlorine, bromine or iodine. Preferred halogen is fluorine or chlorine. Further preferred halogen is fluorine. Alkyl is straight-chain alkyl or branched-chain alkyl, but unless otherwise noted, includes no cyclic alkyl. In general, straight-chain alkyl is preferred to branched-chain alkyl. A same rule applies also to a terminal group such as alkoxy and alkenyl. With regard to a configuration of 1,4-cyclohexylene, trans is preferred to cis for increasing the maximum temperature of the nematic phase. Then, 2-fluoro-1,4-phenylene means two divalent groups described below. In a chemical formula, fluorine may be leftward (L) or rightward (R). A same rule applies also to an asymmetrical divalent group formed by removing two hydrogens from a ring, such as tetrahydropyran-2,5-diyl.

Formula 17

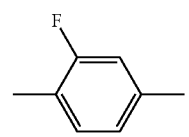

(L)

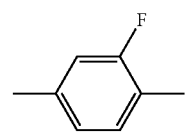

(R)

The invention relates to a liquid crystal medium to be sealed between a pair of substrates subjected to neither alignment treatment nor an alignment film and having a transparent electrode formed on at least one of the substrates, wherein the liquid crystal medium contains a low molecular weight polar compound for homogeneously aligning the liquid crystal medium relative to the substrate, so that the homogeneous alignment of the liquid crystal medium relative to the substrate can occur spontaneously. More specifically, the invention relates to a liquid crystal or liquid crystalline material to be spontaneously homogeneously aligned relative to the substrate, for example, a liquid crystal compound, a liquid crystal composition and a polymer liquid crystal to be spontaneously homogeneously aligned relative to the substrate. In the following, each element structuring the invention will be described in detail.

1. Low Molecular Weight Polar Compound

The polar compound of the invention is a polar compound for homogeneously aligning the liquid crystal medium relative to the substrate, and is the low molecular weight compound. Here, a liquid crystal cell is formed of two substrates subjected to neither alignment treatment nor an alignment film for aligning the liquid crystal medium (the transparent electrode is formed on at least one of the substrates) and the liquid crystal medium interposed therebetween, and the liquid crystal medium homogeneously aligns relative to the substrates by the polar compound added to the liquid crystal medium. An expression "homogeneously align" means that the liquid crystal medium aligns in parallel to a substrate surface, and also the liquid crystal medium aligns inside a plane in parallel to the substrate surface. A chemical structure of the polar compound of the invention is preferably composed of a nonpolar group and a polar group. Although the invention is not bound by a specific principle, the polar group interacts with the substrate or the electrode formed on the substrate, and the nonpolar group interacts with the liquid crystal medium, thereby presumably homogeneously aligning the liquid crystal medium relative to the substrate. The polar compound may have a polymerizable group, and the polar compound having the polymerizable group aligns the liquid crystal medium, and simultaneously is polymerized and copolymerized with any other polymerizable compound by irradiation with ultraviolet light or the like. Thus, alignment before polymerization can be stabilized.

1.1 Positive-Phase Negative-Phase CV Product of Low Molecular Weight Polar Compound A term "positive-phase negative-phase CV product" means a value expressed in terms of a numerical form as to what degree of the polar group and the nonpolar group exist in one molecule, in which the value increases in a compound having a chemical structure in which the polar group having larger electrical bias and the nonpolar group having smaller electrical bias coexist, and the value decreases in the compound having the chemical structure in which the molecule as a whole is neutral.

The positive-phase negative-phase CV product is measured as a product of reciprocal CV values (1/Rf) of each Rf value (development distance of sample/development distance of moving layer) after developing the compound by normal-phase TLC and reversed-phase TLC. The compound having a small Rf value upon measuring the compound by the normal-phase TLC has the polar group, and the compound having the small Rf value upon measuring the compound by the reversed-phase TLC has the nonpolar group. Two characteristics described above may be occasionally simultaneously satisfied in one compound, and neither may be occasionally satisfied. As a standard measuring method, the compound is developed with a mixed solvent (4:1 in a volume ratio) of toluene and ethyl acetate by using TLC (Silica gel 60 F254) made by Merck Ltd. in measuring the compound by the normal-phase TLC, and the compound is developed with methanol by using TLC (Silica gel 60 RP-18 F254s) made by Merck Ltd. in measuring the compound by the reversed-phase TLC.

Positive-phase negative-phase $CV$ product=$1/Rf(p) \times 1/Rf(n)$

Rf(p): Rf value in a positive phase

Rf(n): Rf value in a negative phase

The low molecular weight polar compound of the invention has features of having a positive-phase negative-phase CV product of 1.3 or more, preferably 1.3 to 50.0, further preferably 1.4 to 15.0, and still further preferably 1.5 to 6.0. If the positive-phase negative-phase CV product is adjusted in the range described above, a preferred alignment state can be obtained, and an influence on values of physical properties derived from any other component of the liquid crystal medium can be reduced by suppressing an amount of addition, and moreover, the range of conditions such as the temperature range in which homogeneous alignment is obtained can be extended.

In the low molecular weight polar compound of the invention, a structure thereof is not particularly limited, as long as the low molecular weight polar compound can homogeneously align the liquid crystal medium relative to the substrate. Specific examples of the structure will be described below.

1.2 Low Molecular Weight Polar Compound Represented by Formula (1)

Formula 18

$$M\text{-}P \qquad (1)$$

In formula (1), M is a nonpolar group having 1 or more carbons, and P is a polar group.

In formula (1), M is preferably a nonpolar group having 1 to 50 carbons, further preferably a nonpolar group having 3 to 35 carbons, still further preferably a nonpolar group having 4 to 25 carbons, and particularly preferably a group formed by combining an alkyl chain, cyclohexylene, phenylene and so forth.

In formula (1), P is preferably independently straight-chain, branched-chain or cyclic alkyl having 1 to 25 carbons, and in P, at least one piece of —$CH_2$— nonadjacent to each other may be independently replaced by —N(—P)—, —O—, —S—, —CO—, —CO—O—, —O—CO— or —O—CO—O— in such a manner that N, O and/or S atoms are not directly connected to each other, at least one tertiary carbon (CH group) may be replaced by N, at least one hydrogen may be independently replaced by F or Cl, and at least one piece of —$(CH_2)_2$— may be independently replaced by —CH=CH— or —C≡C—, in which P contains one or more heteroatoms selected from N, S and/or O. P is further preferably a hydroxyl group, an amino group, a carboxyl group, a sulfone group, an ester bond, acrylate, methacrylate or the like.

In addition, $P^0$ in "—N(—$P^0$)—" is independently straight-chain, branched-chain or cyclic alkyl having 1 to 25 carbons, and in $P^0$, at least one piece of —$CH_2$— nonadjacent to each other may be independently replaced by —N(—$P^0$)—, —O—, —S—, —CO—, —CO—O—, —O—CO— or —O—CO—O— in such a manner that N, O and/or S atoms are not directly connected to each other, at least one tertiary carbon (CH group) may be replaced by N, at least one hydrogen may be independently replaced by F or Cl, and at least one piece of —$(CH_2)_2$— may be independently replaced by —CH=CH— or —C≡C—, in which $P^0$ contains one or more heteroatoms selected from N, S and/or O.

1.3 Low Molecular Weight Polar Compound Represented by Formula (2) or (3)

A polar compound represented by formula (2) or (3) is preferred among the polar compounds represented by formula (1).

Formula 19

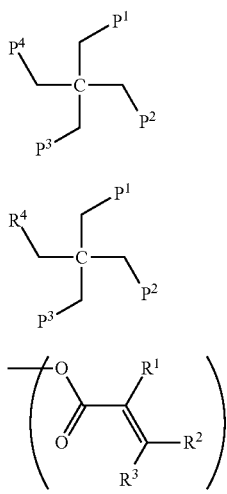

(Q-0)

In formulas (2) and (3), $R^4$ is hydrogen, halogen or alkyl having 1 to 20 carbons, and in $R^4$, at least one piece of —$CH_2$— may be independently replaced by —O— or —S—, and at least one piece of —$(CH_2)_2$— may be replaced by —CH=CH—, and in the groups, at least one hydrogen may be replaced by halogen, $P^1$, $P^2$, $P^3$ and $P^4$ are independently a group represented by formula (Q-0) or straight-chain, branched-chain or cyclic alkyl having 1 to 25 carbons, and in $P^1$, $P^2$, $P^3$ and $P^4$, at least one piece of —$CH_2$— nonadjacent to each other may be independently replaced by —N(—P)—, —O—, —S—, —CO—, —CO—O—, —O—CO— or —O—CO—O— in such a manner that N, O and/or S atoms are not directly connected to each other, at least one tertiary carbon (CH group) may be replaced by N, at least one hydrogen may be independently replaced by F or Cl, and at least one piece of —$(CH_2)_2$— may be independently replaced by —CH=CH— or —C≡C—, in which $P^1$, $P^2$, $P^3$ and $P^4$ contain one or more heteroatoms selected from N, S and/or O, and $P^0$ is independently straight-chain, branched-chain or cyclic alkyl having 1 to 25 carbons, and in $P^0$, at least one piece of —$CH_2$— nonadjacent to each other may be independently replaced by —N(—$P^0$)—, —O—, —S—, —CO—, —CO—O—, —O—CO— or —O—CO—O— in such a manner that N, O and/or S atoms are not directly connected to each other, at least one tertiary carbon (CH group) may be replaced by N, at least one hydrogen may be independently replaced by F or Cl, and at least one piece of —$(CH_2)_2$— may be independently replaced by —CH=CH— or —C≡C—, in which $P^0$ contains one or more heteroatoms selected from N, S and/or O, and in formula (Q-0), $R^1$, $R^2$ and $R^3$ are independently hydrogen, halogen or alkyl having 1 to 20 carbons, and in $R^1$, $R^2$ and $R^3$, at least one piece of —$CH_2$— may be independently replaced by —O— or —S—, and at least one piece of —$(CH_2)_2$— may be replaced by —CH=CH—, and in the groups, at least one hydrogen may be replaced by halogen.

$P^1$ to $P^4$ in formula (2) and $P^1$ to $P^3$ in formula (3) are preferably acrylate or methacrylate, and $R^1$ in formula (3) is preferably alkyl, alkyl having 1 to 30 carbons, alkyl having 1 to 20 carbons or alkyl having 2 to 10 carbons.

A polar compound having a chemical structure described below is preferred among the polar compounds represented by formula (2) or (3):

Formula 20

$R^1$ in formula (2-1) is straight-chain or cyclic alkyl having 1 to 4 carbons; and $R^1$, $R^2$, $R^3$ and $R^4$ in formulas (2-2) and (3-1) are independently hydrogen, halogen or alkyl having 1 to 20 carbons, and in $R^1$, $R^2$, $R^3$ and $R^4$, at least one piece of —$CH_2$— may be independently replaced by —O— or —S—, and at least one piece of —$(CH_2)_2$— may be replaced by —CH=CH—, and in the groups, at least one hydrogen may be replaced by halogen.

A polar compound having the following chemical structure is further preferred.

Formula 21

1.4 Low Molecular Weight Polar Compound Represented by Formula (4)

A polar compound represented by formula (4) is preferred among the polar compounds represented by formula (1).

Formula 22

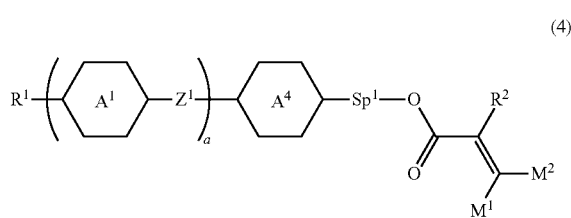

(4)

In formula (4),
R$^1$ is alkyl having 1 to 15 carbons, and in R$^1$, at least one piece of —CH$_2$— may be independently replaced by —O— or —S—, and at least one piece of —(CH$_2$)$_2$— may be independently replaced by —CH=CH— or —C≡C—, and in the groups, at least one hydrogen may be replaced by halogen;

ring A$^1$ and ring A$^4$ are independent 1,4-cyclohexylene, 1,4-cyclohexenylene, 1,4-phenylene, naphthalene-2,6-diyl, decahydronaphthalene-2,6-diyl, 1,2,3,4-tetrahydronaphthalene-2,6-diyl, tetrahydropyran-2,5-diyl, 1,3-dioxane-2,5-diyl, pyrimidine-2,5-diyl, pyridine-2,5-diyl, fluorene-2,7-diyl, phenanthrene-2,7-diyl, anthracene-2,6-diyl, perhydrocyclopenta[a]phenanthrene-3,17-diyl or 2,3,4,7,8,9,10,11,12,13,14,15,16,17-tetradecahydrocyclopenta[a]phenanthrene-3,17-diyl, and in the rings, at least one hydrogen may be independently replaced by fluorine, chlorine, alkyl having 1 to 12 carbons, alkenyl having 2 to 12 carbons, alkoxy having 1 to 11 carbons or alkenyloxy having 2 to 11 carbons, and in the groups, at least one hydrogen may be independently replaced by fluorine or chlorine;

Z$^1$ is a single bond or alkylene having 1 to 10 carbons, and in Z$^1$, at least one piece of —CH$_2$— may be independently replaced by —O—, —CO—, —COO—, —OCO— or —OCOO—, and at least one piece of —(CH$_2$)$_2$— may be independently replaced by —CH=CH— or —C≡C—, and in the groups, at least one hydrogen may be replaced by halogen;

Sp$^1$ is a single bond or alkylene having 1 to 10 carbons, and in Sp$^1$, at least one piece of —CH$_2$— may be independently replaced by —O—, —CO—, —COO—, —OCO— or —OCOO—, and at least one piece of —(CH$_2$)$_2$— may be independently replaced by —CH=CH— or —C≡C—, and in the groups, at least one hydrogen may be replaced by halogen;

M$^1$ and M$^2$ are independently hydrogen, halogen, alkyl having 1 to 5 carbons, or alkyl having 1 to 5 carbons in which at least one hydrogen is replaced by halogen;

a is 0, 1, 2, 3 or 4; and

R$^2$ is a group represented by formula (1a) or formula (1b):

Formula 23

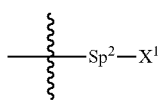

(1a)

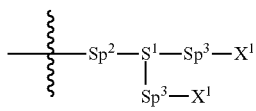

(1b)

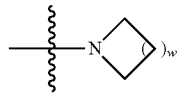

(x1)

in formulas (1a) and (1b),

Sp$^2$ and Sp$^3$ are independently a single bond or alkylene having 1 to 10 carbons, and in Sp$^2$ and Sp$^3$, at least one piece of —CH$_2$— may be independently replaced by —O—, —NH—, —CO—, —COO—, —OCO— or —OCOO—, and at least one piece of —(CH$_2$)$_2$— may be independently replaced by —CH=CH— or —C≡C—, and in the groups, at least one hydrogen may be replaced by halogen;

S$^1$ is >CH— or >N—; and

X$^1$ is independently —OH, —NH$_2$, —OR$^3$, —N(R$^3$)$_2$, a group represented by formula (x1), —COOH, —SH, —B(OH)$_2$ or a group represented by —Si(R$^3$)$_3$, in which R$^3$ is hydrogen or alkyl having 1 to 10 carbons, and in R$^3$, at least one piece of —CH$_2$— may be replaced by —O— and at least one piece of —(CH$_2$)$_2$— may be replaced by —CH=CH—, and in X$^1$, at least one hydrogen may be replaced by halogen, and w in formula (x1) is 1, 2, 3 or 4.

In formula (4), preferred ring A$^1$ or ring A$^2$ is 1,4-cyclohexylene, 1,4-phenylene, perhydrocyclopenta[a]phenanthrene-3,17-diyl or 2,3,4,7,8,9,10,11,12,13,14,15,16,17-tetradecahydrocyclopenta[a]phenanthrene-3,17-diyl, and in the rings, at least one hydrogen may be replaced by fluorine or alkyl having 1 to 5 carbons. Further preferred ring A$^1$ or ring A$^4$ is 1,4-cyclohexylene, 1,4-phenylene or perhydrocyclopenta[a]phenanthrene-3,17-diyl, and in the rings, for example, as in 1-methyl-1,4-cyclohexylene, 2-ethyl-1,4-cyclohexylene and 2-fluoro-1,4-phenylene, at least one hydrogen may be replaced by fluorine, methyl or ethyl.

In formula (4), preferred Z$^1$ is a single bond, —(CH$_2$)$_2$—, —CH=CH—, —C≡C—, —COO—, —OCO—, —CF$_2$O—, —OCF$_2$—, —CH$_2$O—, —OCH$_2$— or —CF=CF—. Further preferred Z$^1$ is a single bond, —(CH$_2$)$_2$— or —CH=CH—. Particularly preferred Z$^1$ is a single bond.

In formula (4), preferred Sp$^1$ is a single bond, alkylene having 1 to 5 carbons, or alkylene having 1 to 5 carbons in which one piece of —CH$_2$— is replaced by —O—. Further preferred Sp$^1$ is a single bond, alkylene having 1 to 3 carbons, or alkylene having 1 to 3 carbons in which one piece of —CH$_2$— is replaced by —O—.

In formula (4), preferred M$^1$ or M$^2$ is hydrogen, fluorine, methyl, ethyl or trifluoromethyl. Further preferred M$^1$ or M$^2$ is hydrogen.

In formula (4), preferred a is 0, 1, 2 or 3. Further preferred a is 0, 1 or 2.

In formulas (1a) and (1b), preferred Sp$^2$ or Sp$^3$ is alkylene having 1 to 7 carbons or alkylene having 1 to 5 carbons in which one piece of —CH$_2$— is replaced by —O—. Further preferred Sp$^2$ or Sp$^3$ is alkylene having 1 to 5 carbons or alkylene having 1 to 5 carbons in which one piece of —CH$_2$— is replaced by —O—. Particularly preferred Sp$^2$ or Sp$^3$ is —CH$_2$—.

In formulas (1a) and (1b), preferred X$^1$ is —OH, —NH$_2$, —OR$^3$, —N(R$^3$)$_2$, a group represented by formula (x1) or a group represented by —Si(R$^3$)$_3$, in which R$^3$ is hydrogen or alkyl having 1 to 5 carbons, and in R$^3$, at least one piece of —CH$_2$— may be replaced by —O—, at least one piece of —(CH$_2$)$_2$— may be replaced by —CH=CH—, and in the groups, at least one hydrogen may be replaced by fluorine, and w in formula (x1) is 1, 2, 3 or 4. Further preferred $X^1$ is —OH, —NH$_2$ or —N(R$^3$)$_2$. Particularly preferred $X^1$ is —OH.

Further specific examples of the polar compound represented by formula (4) include the following.

Formula 24

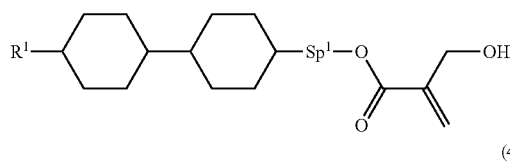
(4-1)

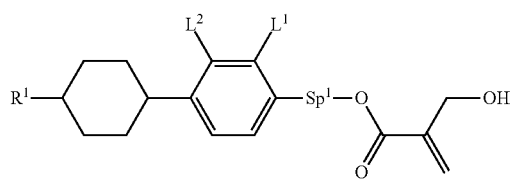
(4-2)

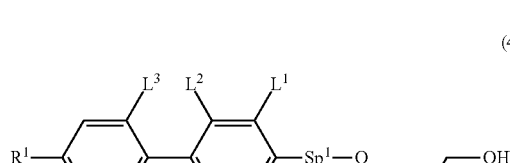
(4-3)

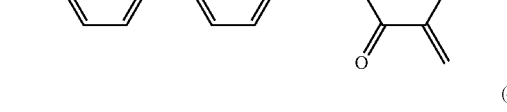
(4-4)

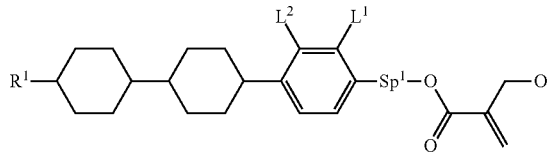
(4-5)

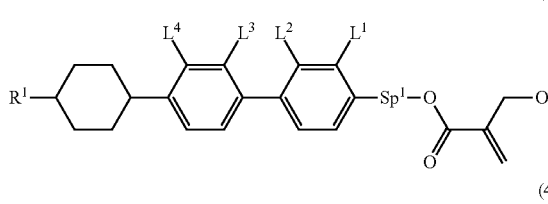
(4-6)

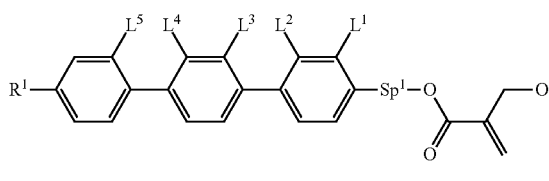
(4-7)

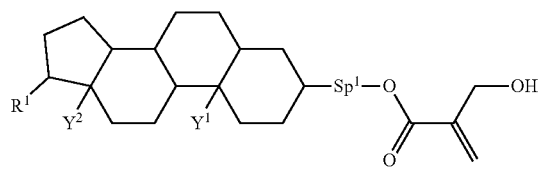
(4-8)

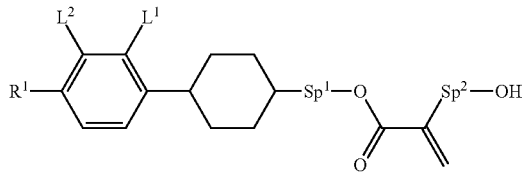
(4-9)

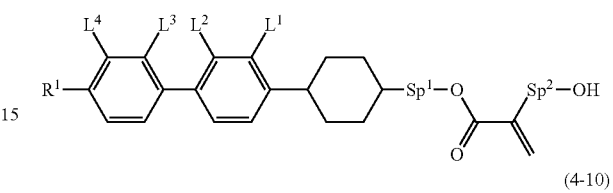
(4-10)

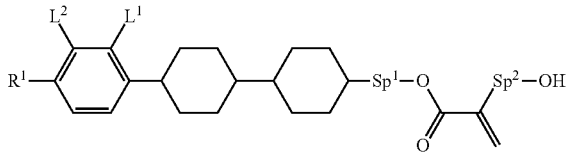

In formulas (4-1) to (4-10), $R^1$ is alkyl having 1 to 10 carbons;

$Sp^1$ is a single bond or alkylene having 1 to 5 carbons, and in $Sp^1$, at least one piece of —CH$_2$— may be replaced by —O—, and in the groups, at least one hydrogen may be replaced by fluorine;

$Sp^2$ is alkylene having 1 to 5 carbons, and in $Sp^2$, at least one piece of —CH$_2$— may be replaced by —O—;

$L^1$, $L^2$, L, $L^4$ and $L^5$ are independently hydrogen, fluorine, methyl or ethyl; and $Y^1$ and $Y^2$ are independently hydrogen or methyl.

Further specific examples of the polar compound represented by formula (4) include the following.

Formula 25

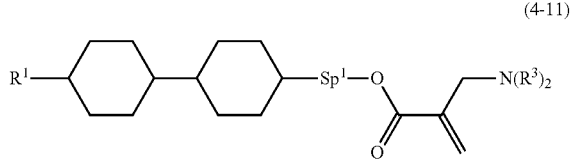
(4-11)

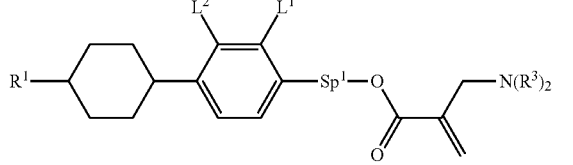
(4-12)

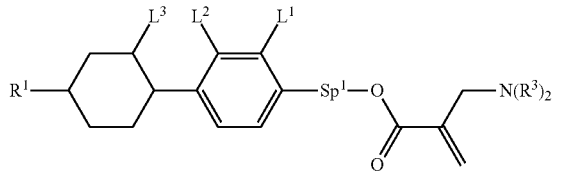
(4-13)

-continued (4-14)
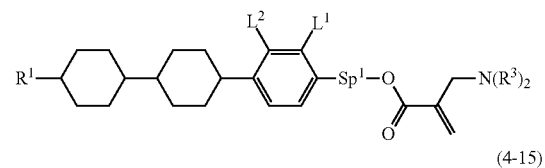

(4-15)
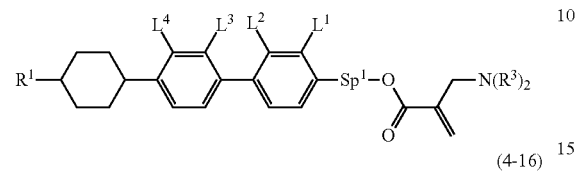

(4-16)
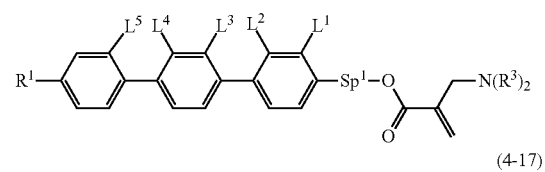

(4-17)
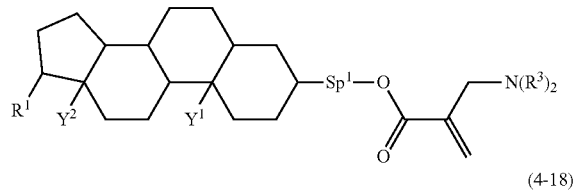

(4-18)
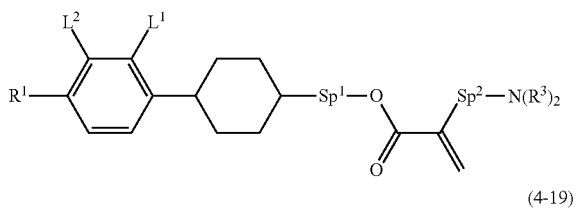

(4-19)
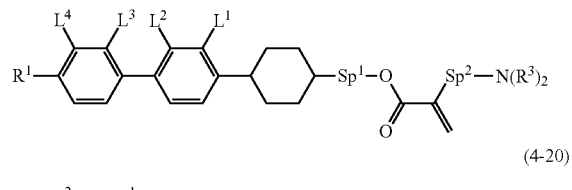

(4-20)
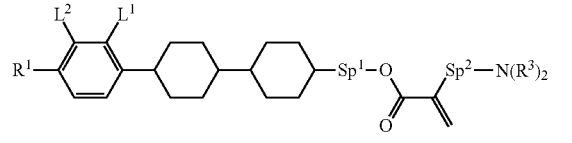

In formulas (4-11) to (4-20), $R^1$ is alkyl having 1 to 10 carbons;

$Sp^1$ is a single bond or alkylene having 1 to 5 carbons, and in $Sp^1$, at least one piece of —$CH_2$— may be replaced by —O—, and in the groups, at least one hydrogen may be replaced by fluorine;

$Sp^2$ is alkylene having 1 to 5 carbons, and in $Sp^2$, at least one piece of —$CH_2$— may be replaced by —O—;

$L^1$, $L^2$, $L^3$, $L^4$ and $L^5$ are independently hydrogen, fluorine, methyl or ethyl;

$Y^1$ and $Y^2$ are independently hydrogen or methyl; and $R^3$ is hydrogen, methyl or ethyl.

A polar compound having the following chemical structure is further preferred.

Formula 26

(4-11-1)
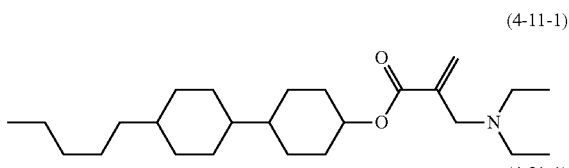

(4-21-1)
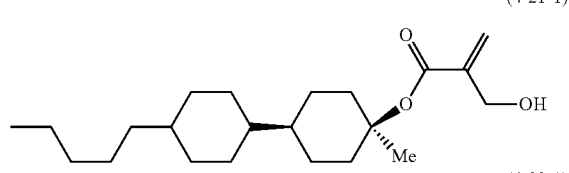

(4-22-1)
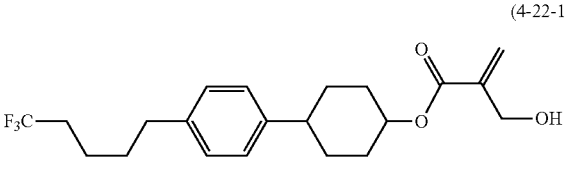

1.5 Synthesis of Low Molecular Weight Polar Compound

The polar compound represented by formula (1) and the polar compounds represented by formulas (2) and (3) each are a bonded body of the nonpolar group and the polar group, and if knowledge of publicly-known organic synthesis for those skilled in the art is utilized, the polar compounds can be easily prepared.

Low Molecular Weight Polar Compound Represented by Formula (2)

For example, as a method for preparing the polar compound represented by formula (2-1) or the polar compound represented by formula (2-2) classified in the polar compound represented by formula (2), the polar compound can be prepared in such a manner that pentaerythritol is esterified with arbitrary carboxylic acid or acid chloride as described below.

Formula 27

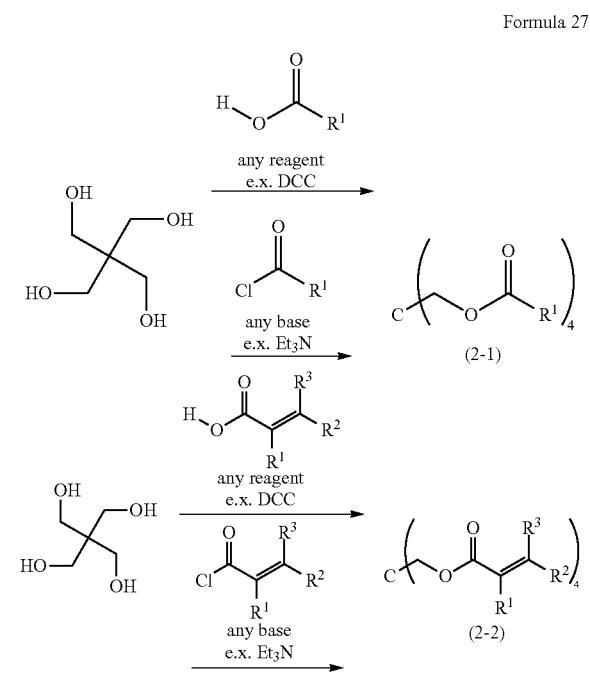

Low Molecular Weight Polar Compound Represented by Formula (3)

Moreover, for example, as a method for preparing the polar compound represented by formula (3-1) classified in the polar compound represented by formula (3), the polar compound can be prepared in such a manner that triol is prepared by allowing paraformaldehyde to react with arbitrary aldehyde under basic conditions, and arbitrary carboxylic acid or acid chloride is esterified as described below.

Formula 28

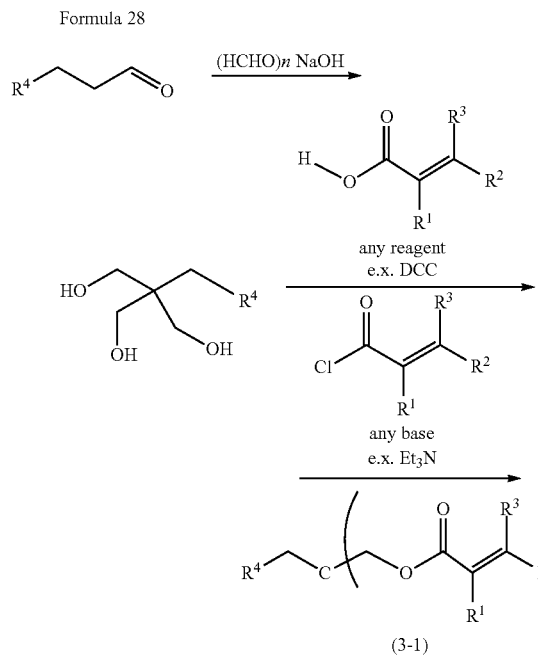

Low Molecular Weight Polar Compound Represented by Formula (4)

The polar compound represented by formula (4) is also the bonded body of the nonpolar group and the polar group, and if the knowledge of publicly-known organic synthesis for those skilled in the art is utilized, the polar compound can be easily prepared.

Formation of a Bonding Group

An example of a method for forming a bonding group in compound (4) is as described in the scheme below. In the scheme, $MSG^1$ (or $MSG^2$) is a monovalent organic group having at least one ring. Monovalent organic groups represented by a plurality of $MSG^1$ (or $MSG^2$) may be identical or different. Compounds (1A) to (1G) correspond to compound (4) or an intermediate of compound (4).

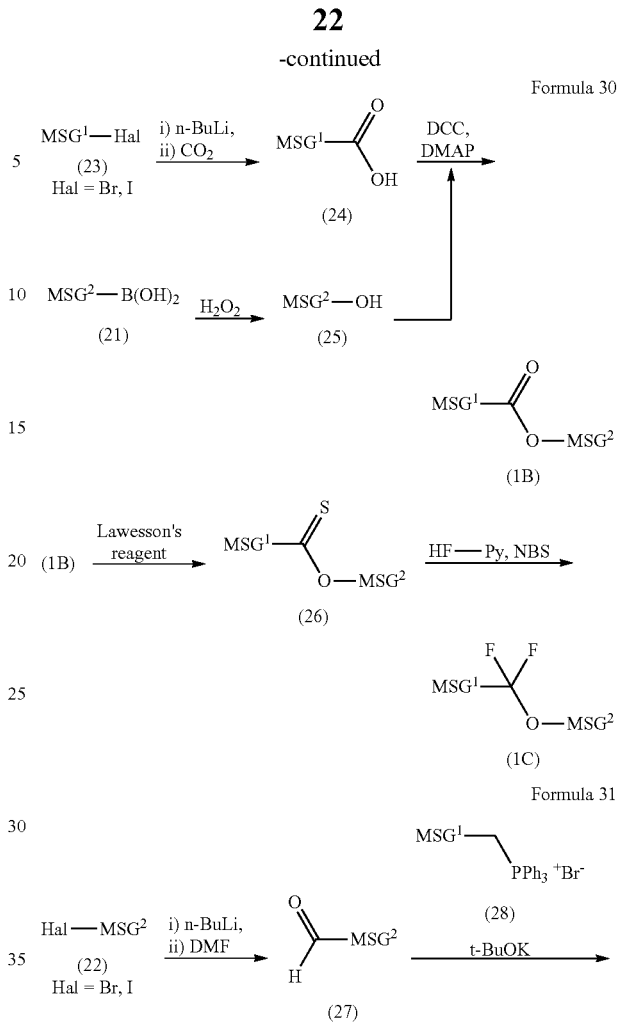

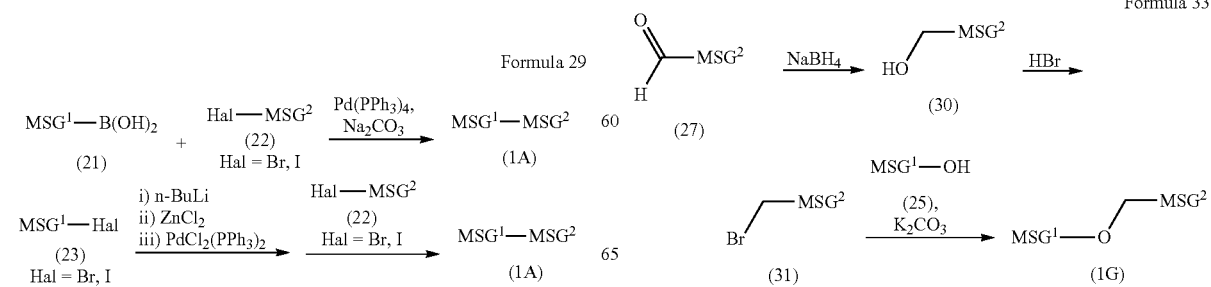

Formula 34

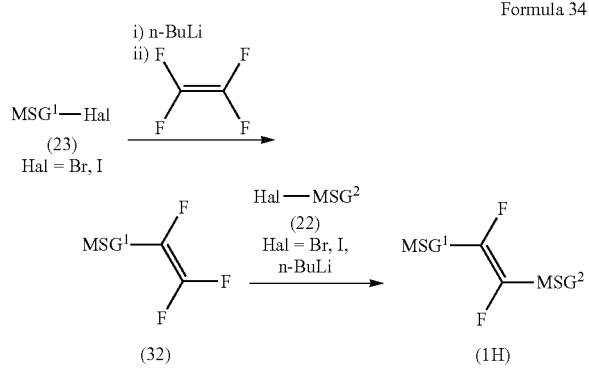

(I) Formation of a Single Bond

Compound (1A) is prepared by allowing aryl boronic acid (21) to react with compound (22) in the presence of carbonate and a tetrakis(triphenylphosphine) palladium catalyst. Compound (1A) is also prepared by allowing compound (23) to react with n-butyllithium and subsequently with zinc chloride, and further with compound (22) in the presence of a dichlorobis(triphenylphosphine)palladium catalyst.

(II) Formation of —COO— and —OCO—

Carboxylic acid (24) is obtained by allowing compound (23) to react with n-butyllithium and subsequently with carbon dioxide. Compound (1B) having —COO— is prepared by dehydration of carboxylic acid (24) and phenol (25) derived from compound (21) in the presence of 1,3-dicyclohexylcarbodiimide (DCC) and 4-dimethylaminopyridine (DMAP). A compound having —OCO— is also prepared according to the method.

(III) Formation of —CF$_2$O— and —OCF$_2$—

Compound (26) is obtained by sulfurizing compound (1B) with a Lawesson's reagent. Compound (1C) having —CF$_2$O— is prepared by fluorinating compound (26) with a hydrogen fluoride-pyridine complex and N-bromosuccinimide (NBS). Refer to M. Kuroboshi et al., Chem. Lett., 1992, 827. Compound (1C) is also prepared by fluorinating compound (26) with (diethylamino)sulfur trifluoride (DAST). Refer to W. H. Bunnelle et al., J. Org. Chem. 1990, 55, 768. A compound having —OCF$_2$— is also prepared according to the method.

(IV) Formation of —CH=CH—

Aldehyde (27) is obtained by allowing compound (22) to react with n-butyllithium and subsequently with N,N-dimethylformamide (DMF). Compound (1D) is prepared by allowing phosphorus ylide generated by allowing phosphonium salt (28) to react with potassium t-butoxide to react with aldehyde (27). A cis isomer may be generated depending on reaction conditions, and therefore the cis isomer is isomerized into a trans isomer according to a publicly-known method, when necessary.

(V) Formation of —(CH$_2$)$_2$—

Compound (1E) is prepared by hydrogenating compound (1D) in the presence of a palladium on carbon catalyst.

(VI) Formation of —C≡C—

Compound (29) is obtained by allowing compound (23) to react with 2-methyl-3-butyn-2-ol in the presence of a catalyst of dichloropalladium and copper iodide and then performing deprotection of the resulting compound under basic conditions. Compound (1F) is prepared by allowing compound (29) to react with compound (22) in the presence of a catalyst of dichlorobis(triphenylphosphine) palladium and copper halide.

(VII) Formation of —CH$_2$O— and —OCH$_2$—

Compound (30) is obtained by reducing compound (27) with sodium borohydride. Compound (31) is obtained by brominating the obtained compound with hydrobromic acid. Compound (1G) is prepared by allowing compound (25) to react with compound (31) in the presence of potassium carbonate. A compound having —OCH$_2$— is also prepared according to the method.

(VIII) Formation of —CF=CF—

Compound (32) is obtained by treating compound (23) with n-butyllithium and then allowing the treated compound to react with tetrafluoroethylene. Compound (1H) is prepared by treating compound (22) with n-butyllithium and then allowing the treated compound to react with compound (32).

Formation of Ring A$^1$ and Ring A$^2$

A starting material is commercially available or a synthetic method is well known with regard to a ring such as 1,4-cyclohexylene, 1,4-cyclohexenylene, 1,4-phenylene, 2-fluoro-1,4-phenylene, 2-methyl-1,4-phenylene, 2-ethyl-1,4-phenylene, naphthalene-2,6-diyl, decahydronaphthalene-2,6-diyl, 1,2,3,4-tetrahydronaphthalene-2,6-diyl, tetrahydropyran-2,5-diyl, 1,3-dioxane-2,5-diyl, pyrimidine-2,5-diyl, pyridine-2,5-diyl, perhydrocyclopenta[a]phenanthrene-3,17-diyl and 2,3,4,7,8,9,10,11,12,13,14,15,16,17-tetradecahydrocyclopenta[a]phenanthrene-3,17-diyl.

Any other method for preparing a compound having a specific chemical structure classified in the polar compound represented by formula (4) is as described below. In description of synthesis methods described below, definitions of R$^1$, M$^1$ and M$^2$ are identical to the definitions described above. In addition, "MES" represents a site formed of A$^1$, Z$^1$ and A$^4$ in formula (4).

Compound (4-51) in which R$^2$ in formula (4) is —CH$_2$—OH can be prepared according to the method described below. Compound (c) is obtained by allowing compound (a) to react with compound (b) in the presence of N, N'-dicyclohexylcarbodiimide (DCC) and N, N-dimethyl-4-aminopyridine (DMAP). Compound (4-51) can be derived therefrom by allowing compound (c) to react with formaldehyde (HCHO) in the presence of 1,4-diazabicyclo[2.2.2]octane (DABCO). In addition, compound (c) can also be prepared by allowing compound (a) to react with compound (d) in the presence of a base such as triethylamine.

Formula 35

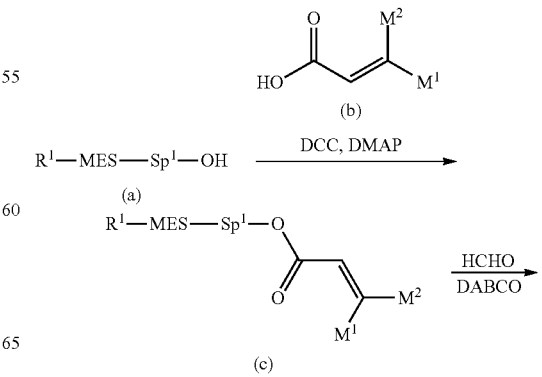

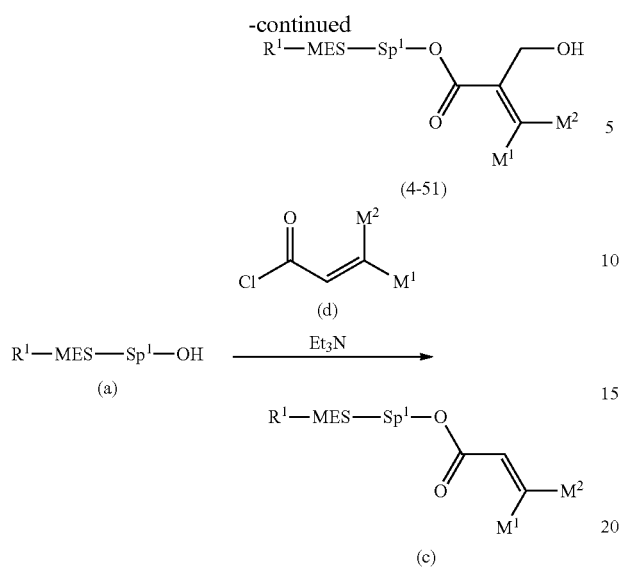

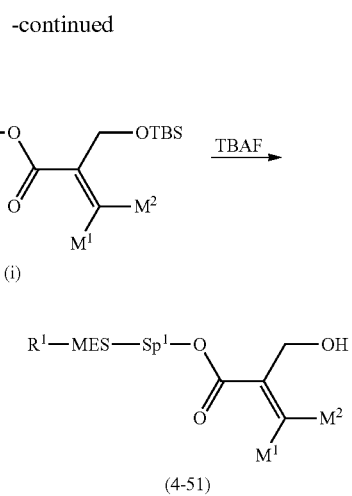

Compound (4-51) can also be prepared according to the method described below. Compound (f) is obtained by allowing compound (e) to react with formaldehyde in the presence of DABCO. Next, compound (g) is obtained by allowing t-butyldimethylsilyl chloride (TBSCl) and imidazole to act on compound (f), and then compound (h) is obtained by allowing compound (g) to hydrolyze with a base such as lithium hydroxide. Compound (i) is obtained by allowing compound (a) to react with compound (h) in the presence of DCC and DMAP, and then compound (4-51) can be derived by performing deprotection of compound (i) by using tetrabutylammonium fluoride (TBAF).

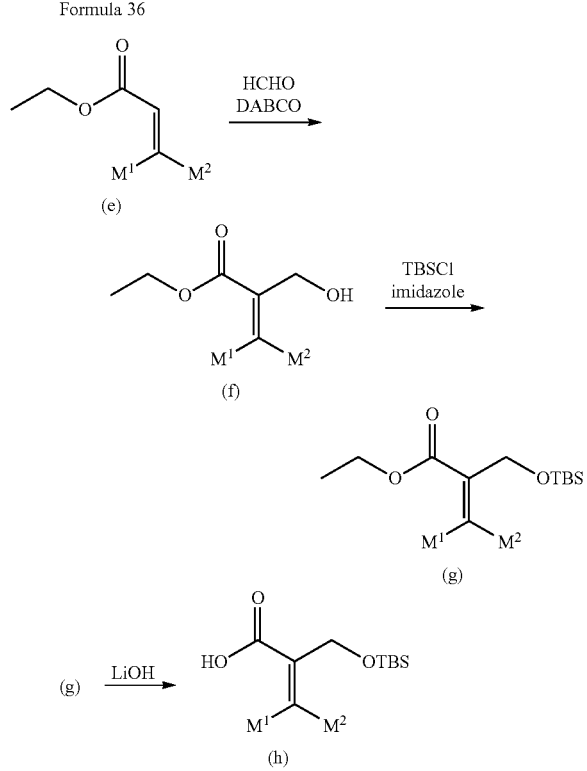

Compound (4-52) in which $R^2$ in formula (4) is —$(CH_2)_2$—OH can be prepared according to the method described below. Compound (j) is obtained by allowing phosphorus tribromide to act on compound (4-51). Next, compound (4-52) can be derived therefrom by allowing indium to act on compound (j) and then allowing the resulting compound to react with formaldehyde.

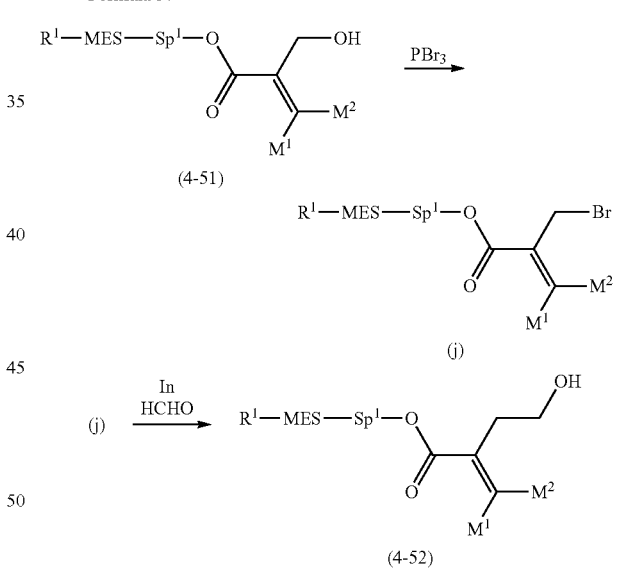

2. Liquid Crystal Compound

A preferred liquid crystal compound represented by any one of formulas (5) to (8) and (16) to (18) used in the invention will be described below. The liquid crystal composition satisfying at least one of characteristics such as high maximum temperature, low minimum temperature, small viscosity, suitable optical anisotropy, large positive or negative dielectric anisotropy, large specific resistance, high stability to ultraviolet light, high stability to heat and a large elastic constant can be prepared by suitably combining the compounds. A liquid crystal compound different from the compounds may be added thereto, when necessary.

2.1 Liquid Crystal Compound Represented by Formulas (5) to (7)

Formula 38

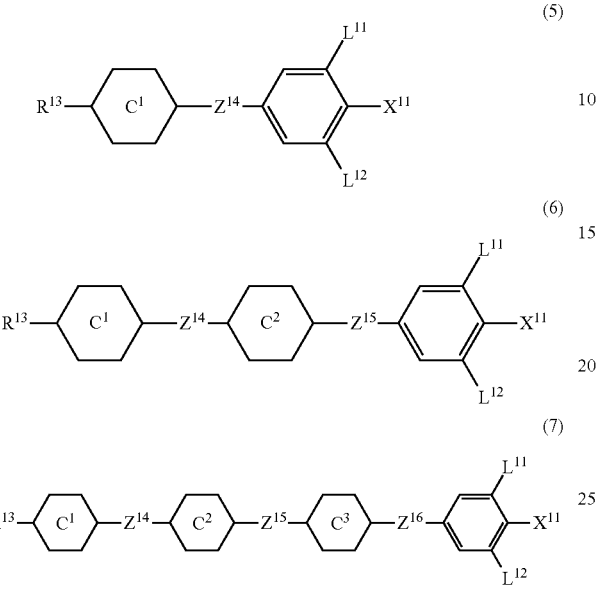

In formulas (5) to (7), $R^{13}$ is alkyl having 1 to 10 carbons or alkenyl having 2 to 10 carbons, and in $R^{13}$, at least one piece of —$CH_2$— may be replaced by —O—, and at least one hydrogen may be replaced by fluorine;

$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;

ring $C^1$, ring $C^2$ and ring $C^3$ are independently 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;

$Z^{14}$, $Z^{15}$ and $Z^{16}$ are independently a single bond, —$(CH_2)_2$—, —CH=CH—, —C≡C—, —COO—, —$CF_2O$—, —$OCF_2$—, —$CH_2O$— or —$(CH_2)_4$—; and $L^{11}$ and $L^{12}$ are independently hydrogen or fluorine.

The liquid crystal compound represented by formulas (5) to (7) each is a compound having a halogen-containing group or a fluorine-containing group at a right terminal. Preferred examples thereof include compounds (5-1) to (5-16), compounds (6-1) to (6-113) and compounds (7-1) to (7-57). In the formulas, $R^{13}$ and $X^{11}$ are defined in the same manner as in formulas (5) to (7).

Formula 39

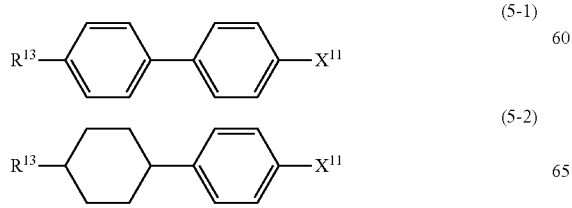

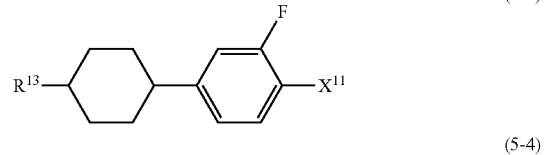

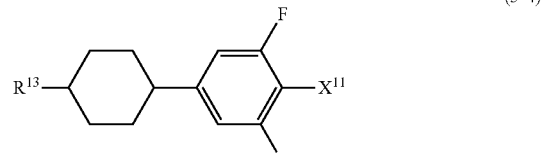

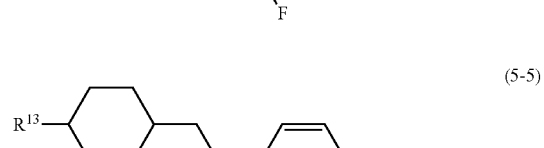

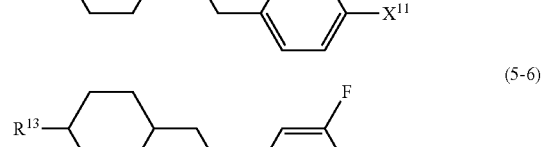

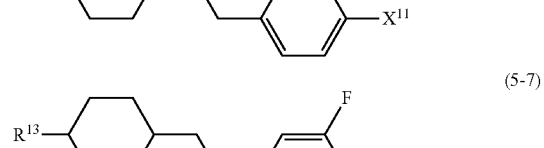

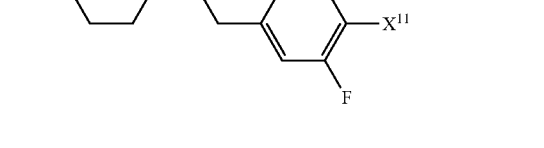

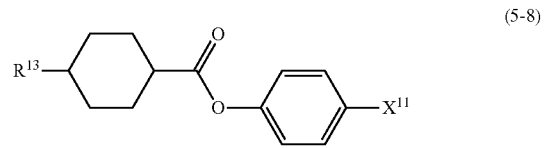

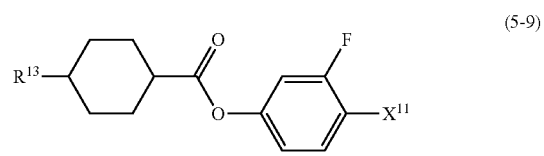

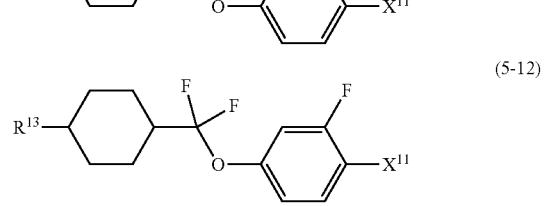

(5-13) 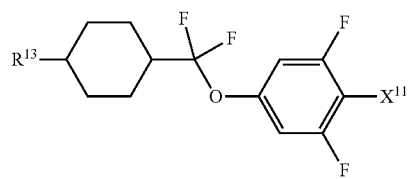
(5-14) 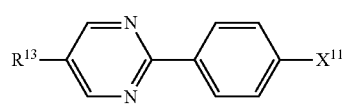
(5-15) 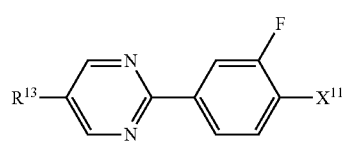
(5-16) 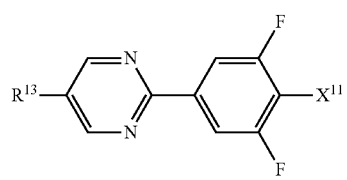
Formula 40
(6-1) 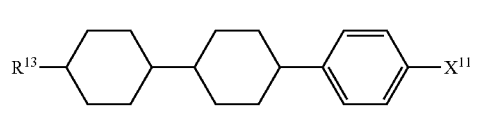
(6-2) 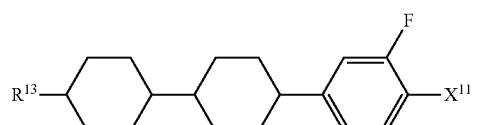
(6-3) 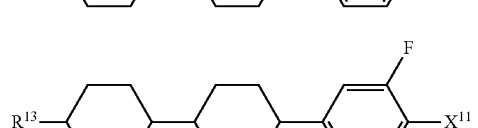
(6-4) 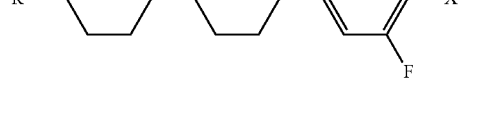
(6-5) 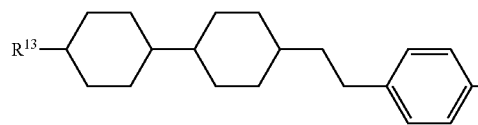
(6-6) 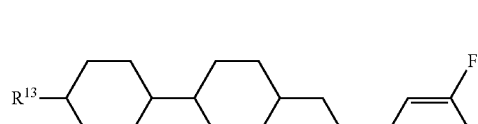
(6-7) 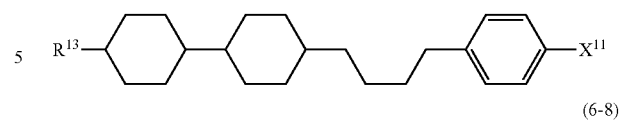
(6-8) 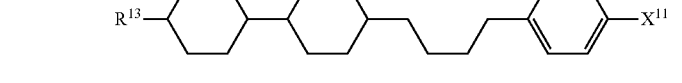
(6-9) 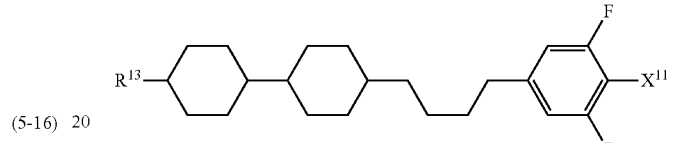
(6-10) 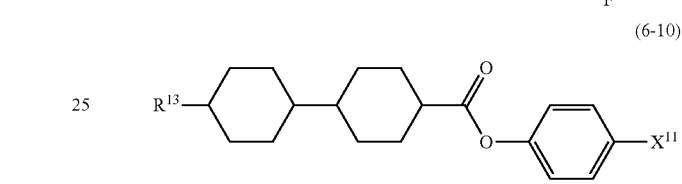
(6-11) 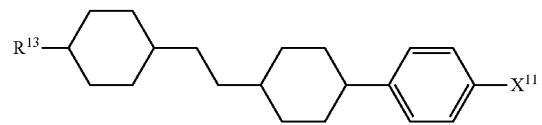
(6-12) 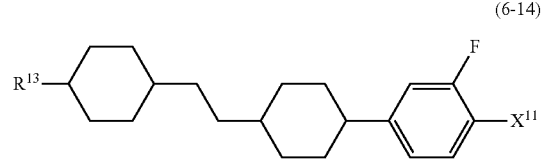
(6-13) 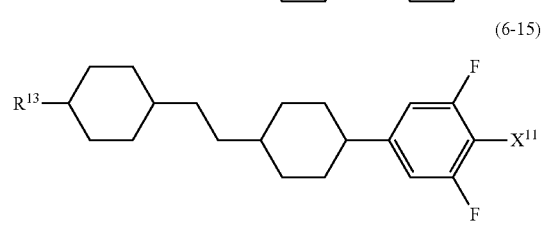
(6-14) 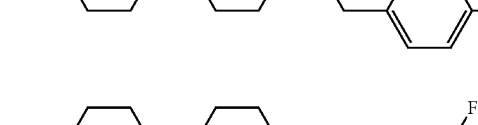
(6-15) 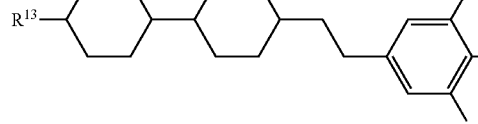

(6-16) 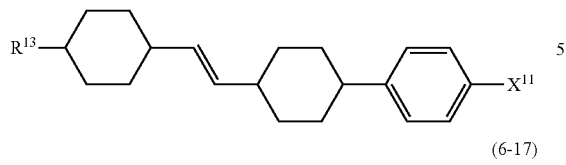
(6-17) 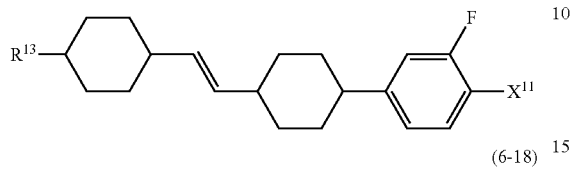
(6-18) 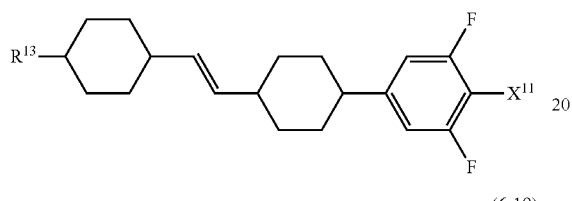
(6-19) 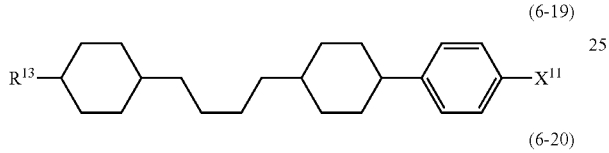
(6-20) 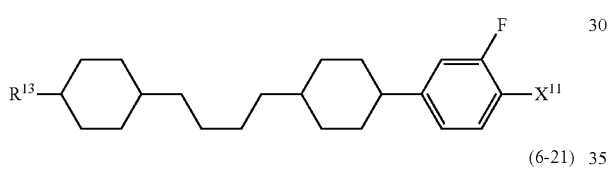
(6-21) 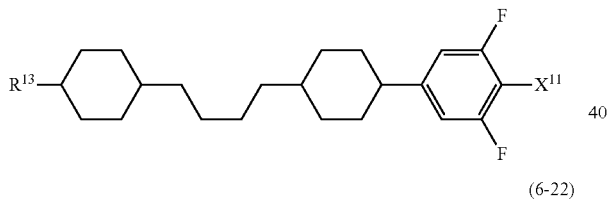
(6-22) 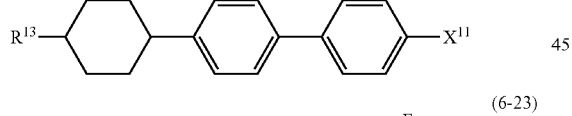
(6-23) 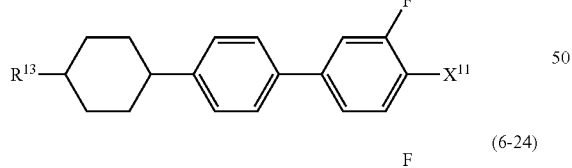
(6-24) 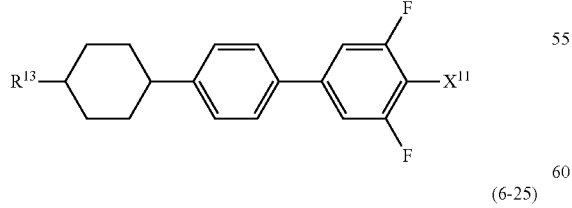
(6-25) 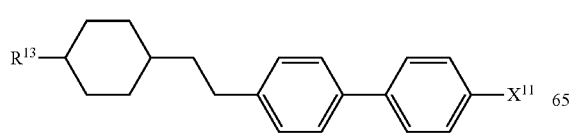
(6-26) 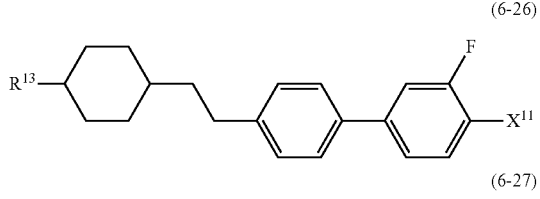
(6-27) 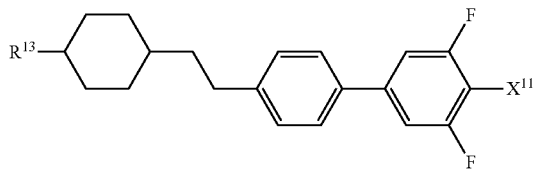
(6-28) 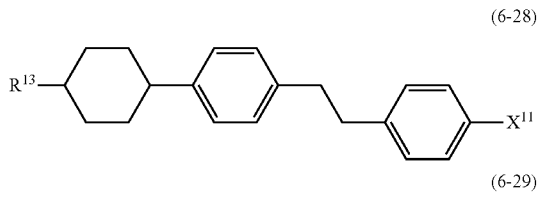
(6-29) 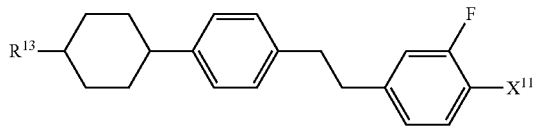
(6-30) 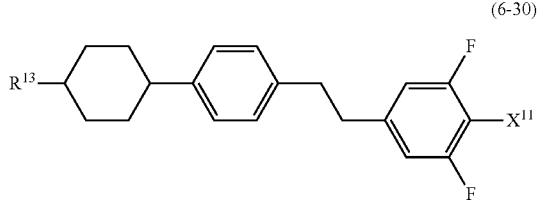
(6-31) 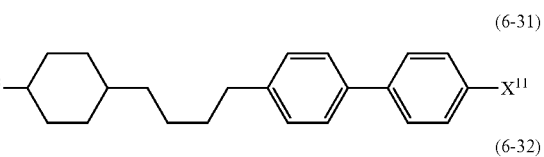
(6-32) 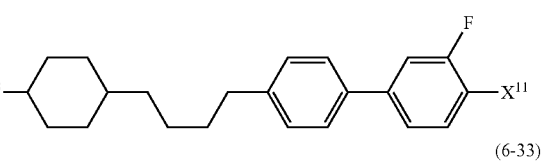
(6-33) 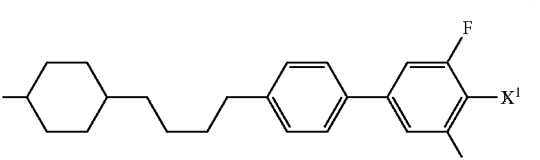
(6-34) 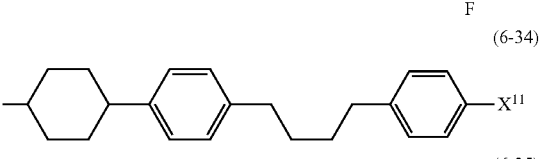
(6-35) 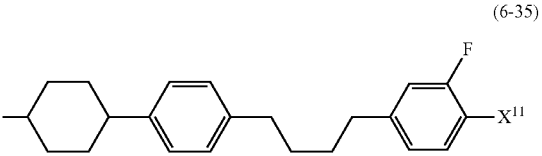

(6-36)
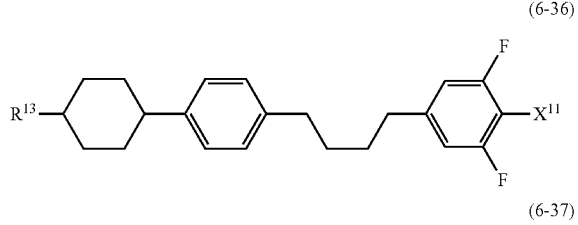
(6-37)
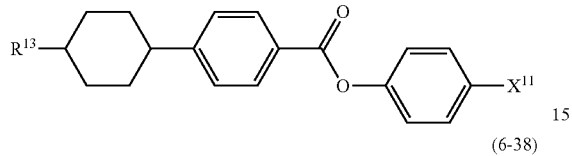
(6-38)
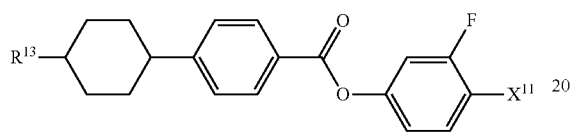
Formula 41
(6-39)
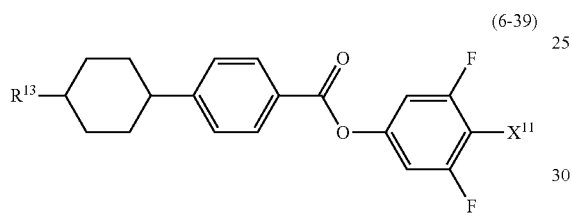
(6-40)
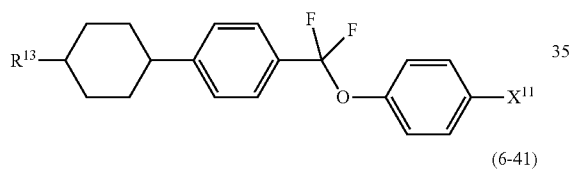
(6-41)
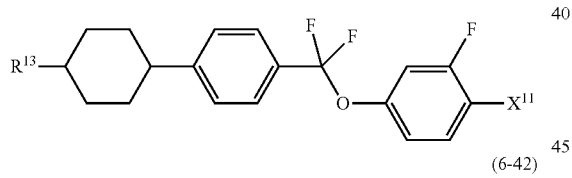
(6-42)
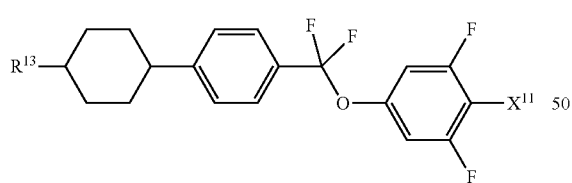
(6-43)
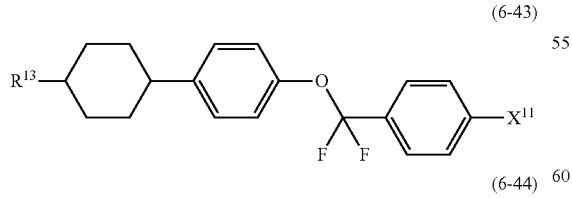
(6-44)
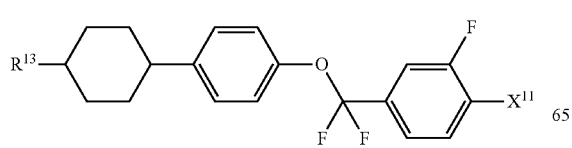
(6-45)
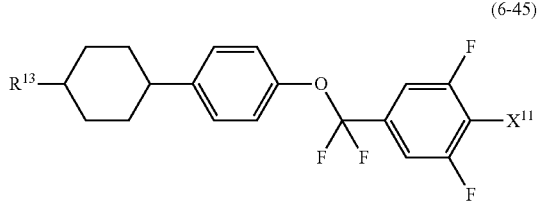
(6-46)
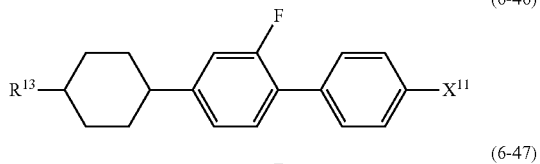
(6-47)
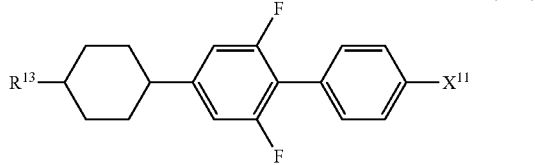
(6-48)
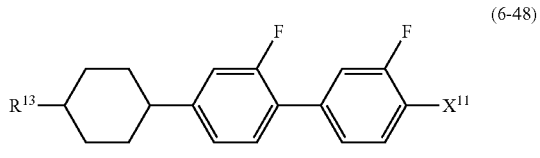
(6-49)
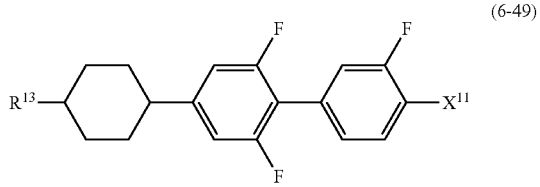
(6-50)
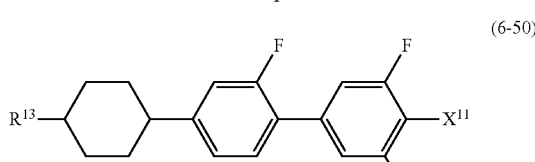
(6-51)
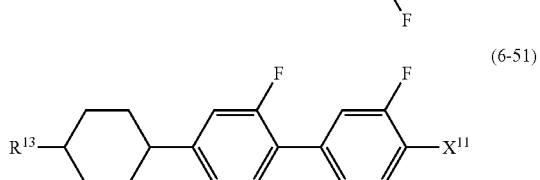
(6-52)
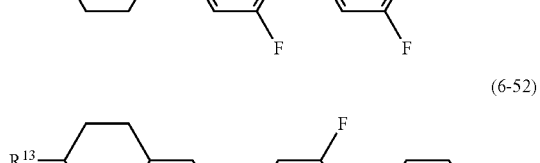
(6-53)
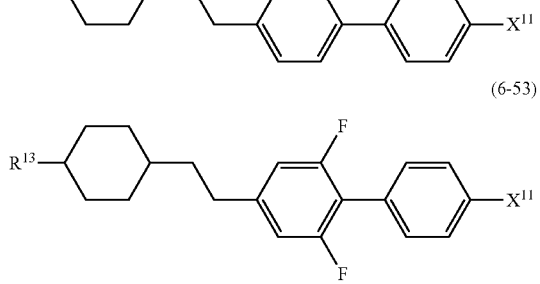

(6-54) 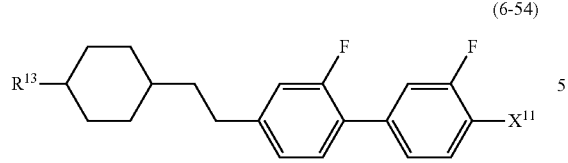
(6-55) 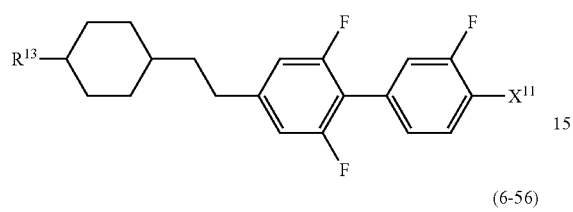
(6-56) 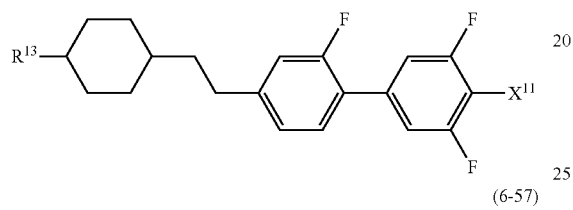
(6-57) 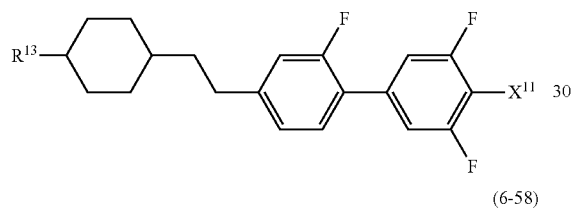
(6-58) 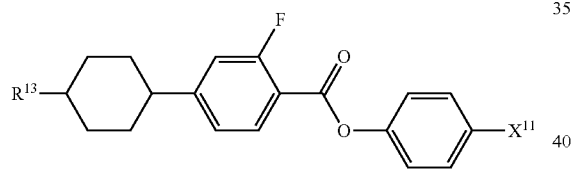
(6-59) 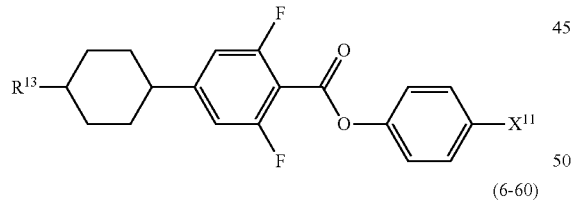
(6-60) 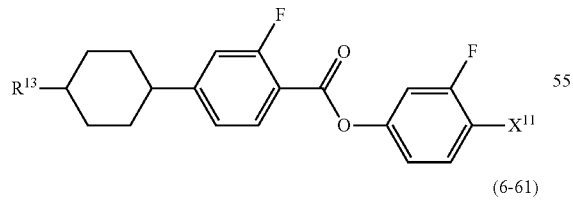
(6-61) 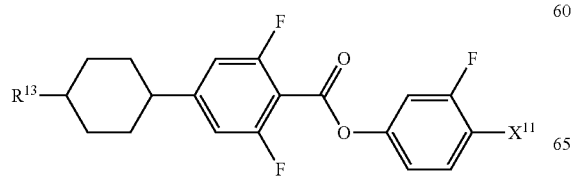
(6-62) 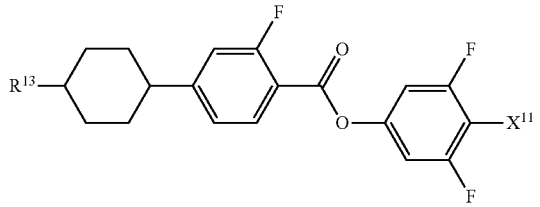
(6-63) 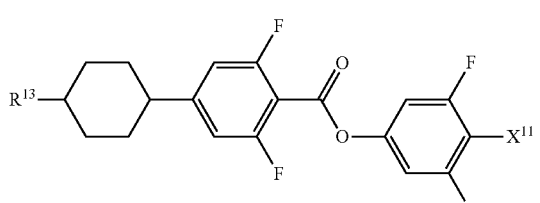
(6-64) 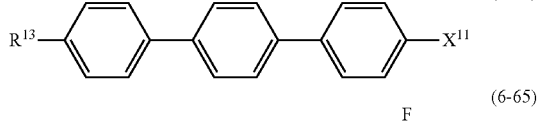
(6-65) 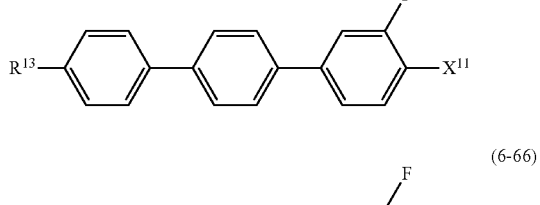
(6-66) 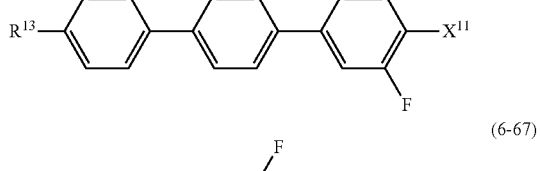
(6-67) 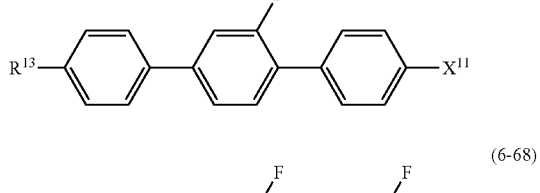
(6-68) 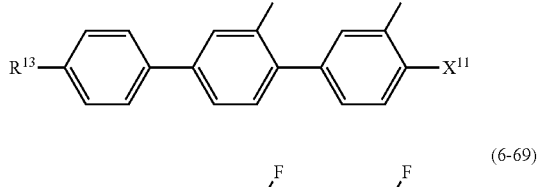
(6-69) 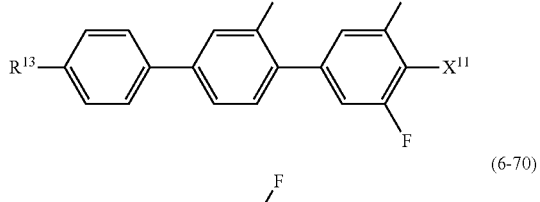
(6-70) 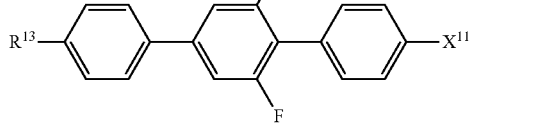

(6-71) 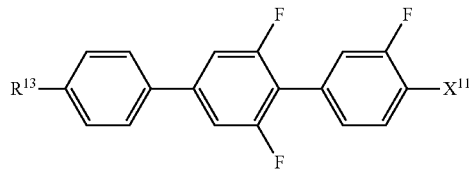
(6-72) 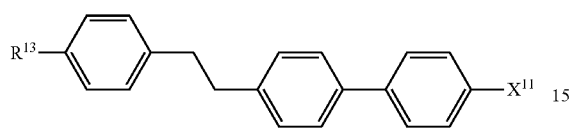
(6-73) 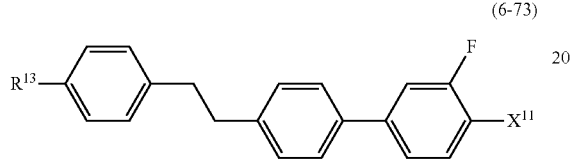
(6-74) 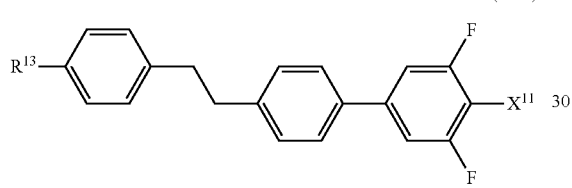
(6-75) 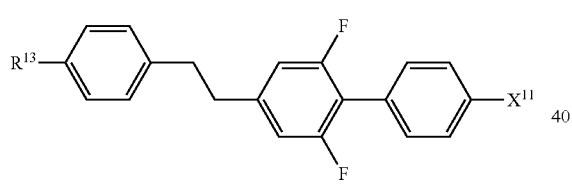
(6-76) 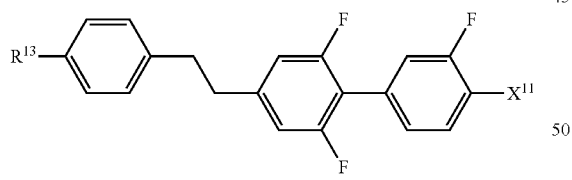
Formula 42
(6-77) 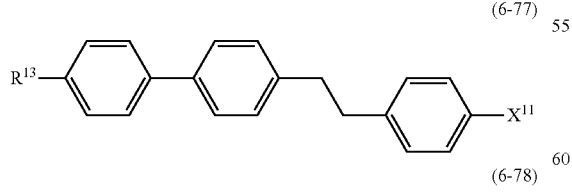
(6-78) 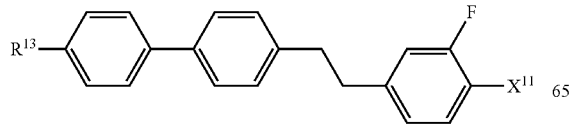
(6-79) 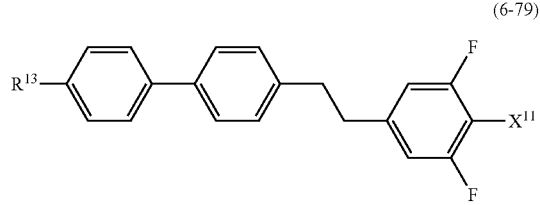
(6-80) 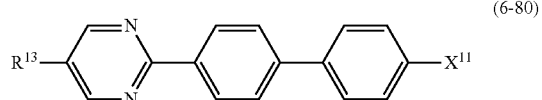
(6-81) 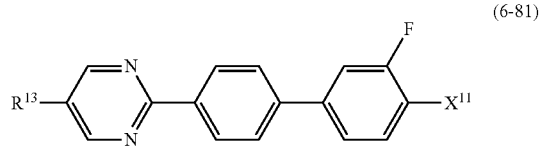
(6-82) 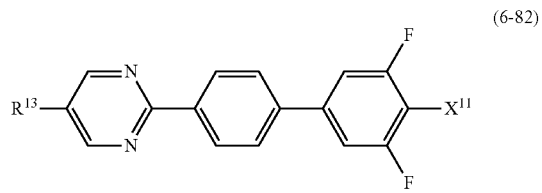
(6-83) 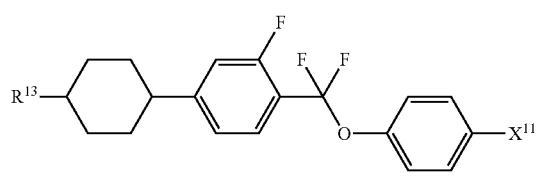
(6-84) 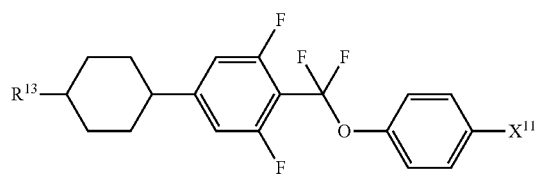
(6-85) 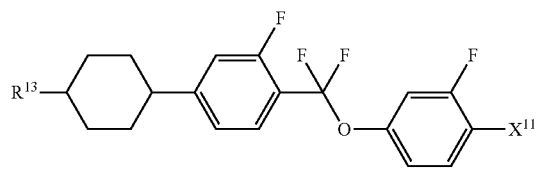
(6-86) 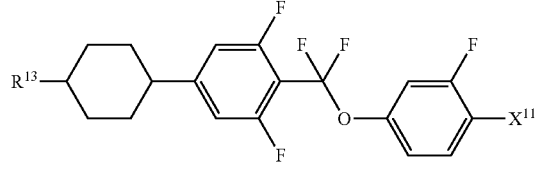

(6-87)
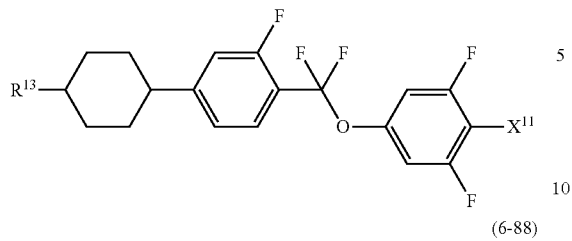
(6-88)
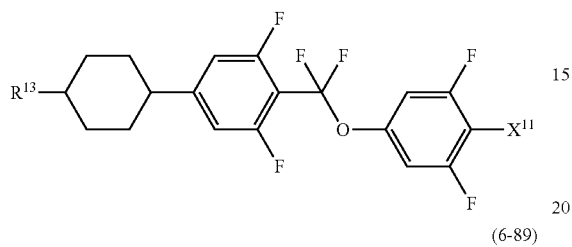
(6-89)
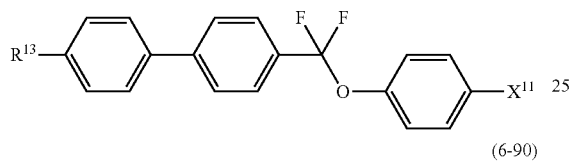
(6-90)
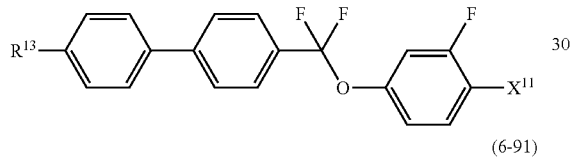
(6-91)
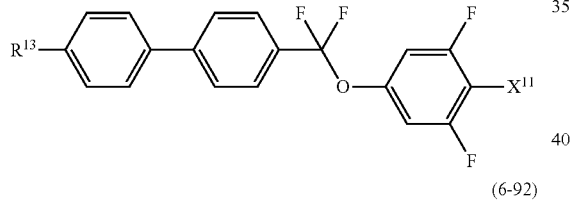
(6-92)
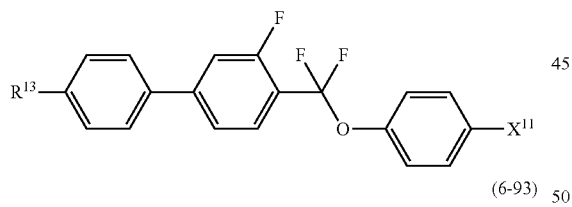
(6-93)
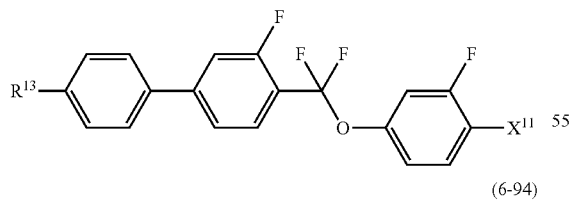
(6-94)
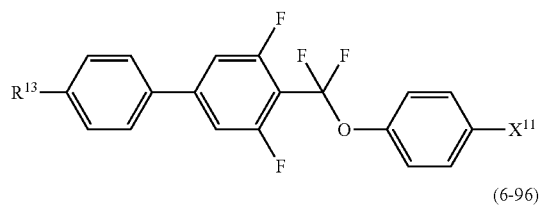
(6-95)
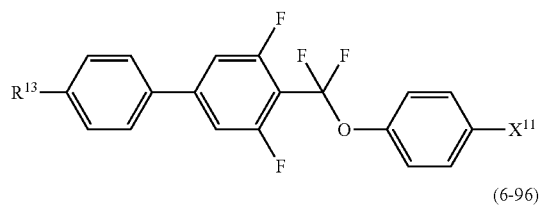
(6-96)
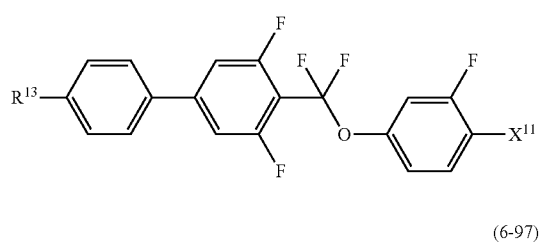
(6-97)
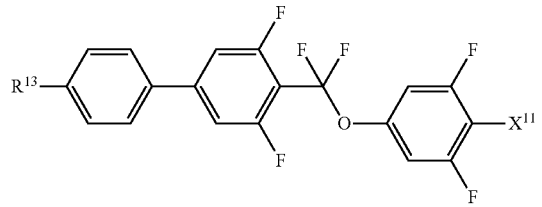
(6-98)
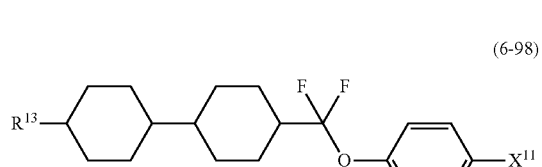
(6-99)
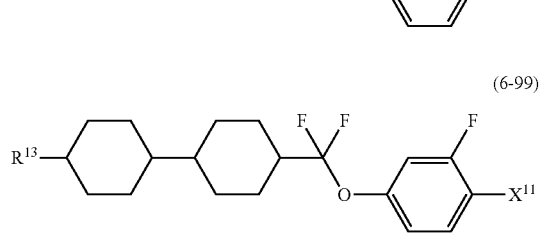
(6-100)
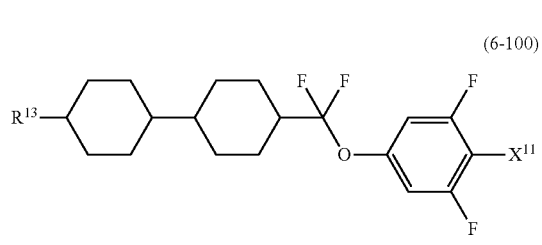
(6-101)
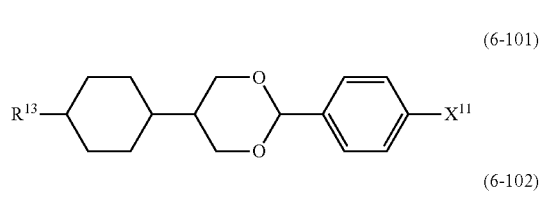
(6-102)

(6-103)
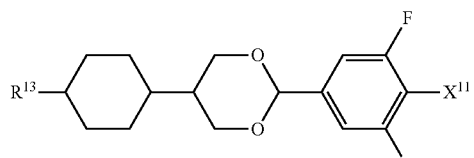
(6-104)
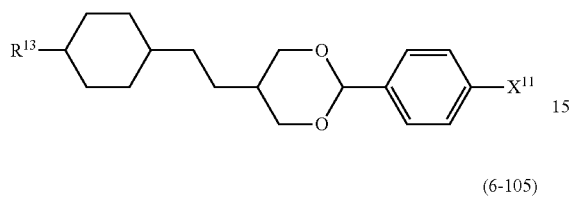
(6-105)
(6-106)
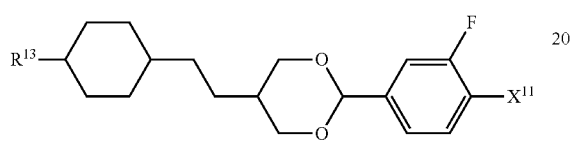
(6-107)
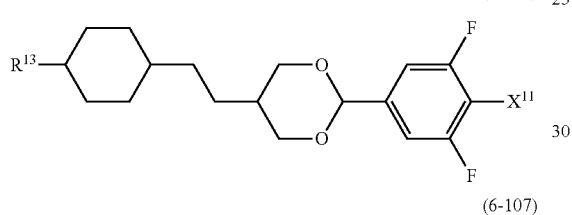
(6-108)
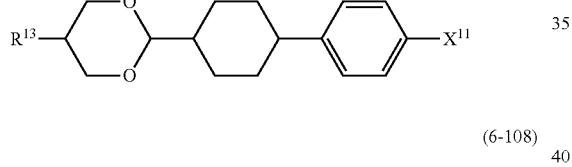
(6-109)
(6-110)
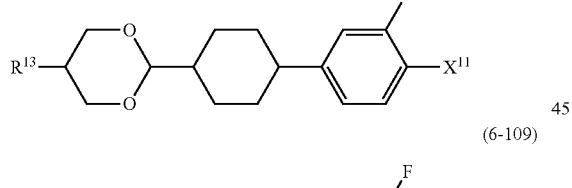
(6-111)
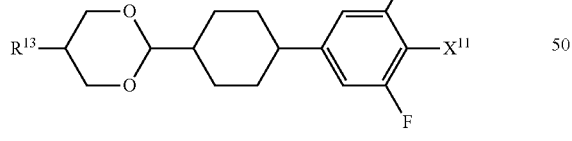
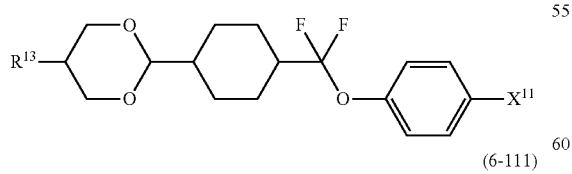
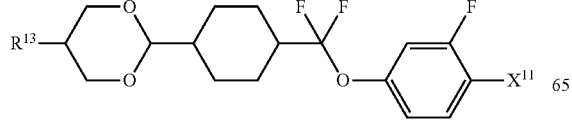
(6-112)
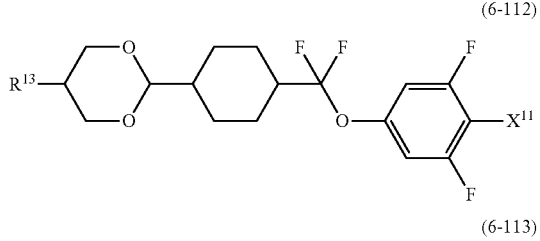
(6-113)
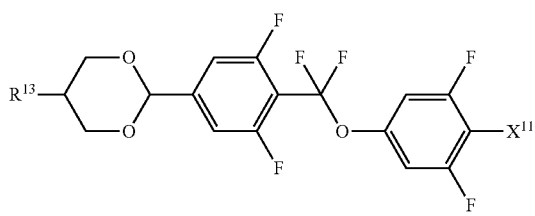
Formula 43
(7-1)
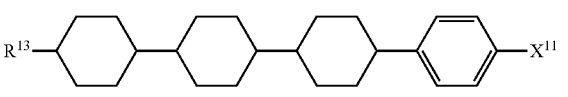
(7-2)
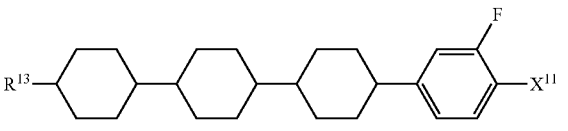
(7-3)
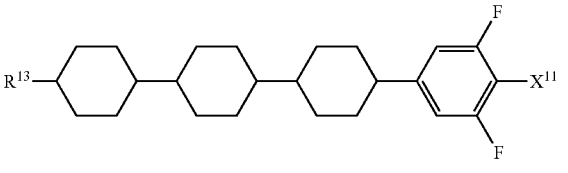
(7-4)
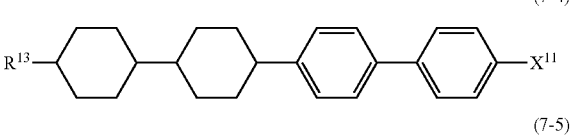
(7-5)
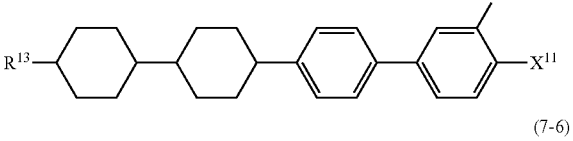
(7-6)
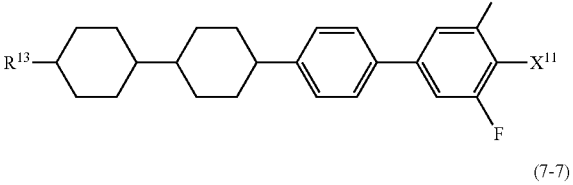
(7-7)
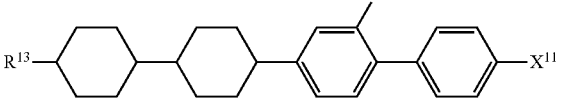

-continued

-continued
(7-27)
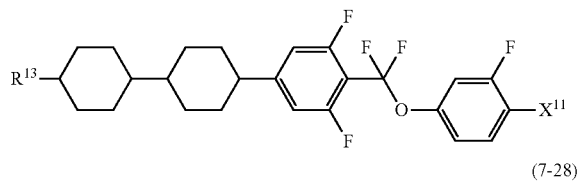
(7-28)
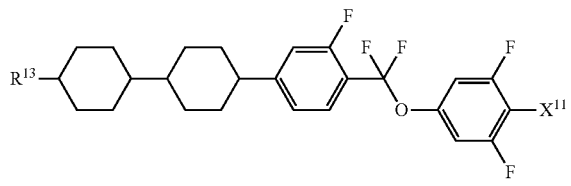
(7-29)
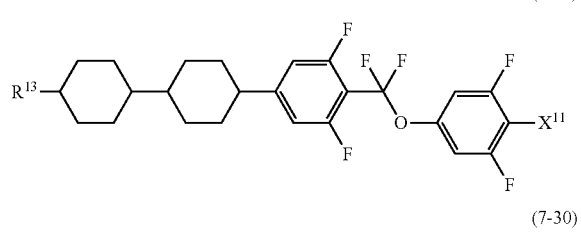
(7-30)
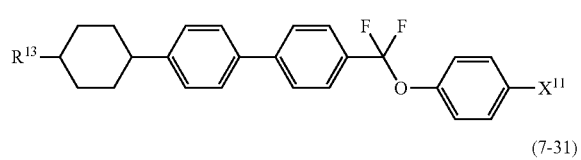
(7-31)
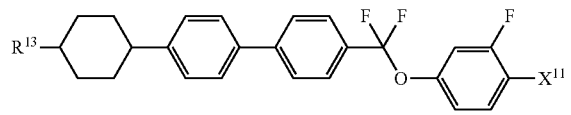
(7-32)
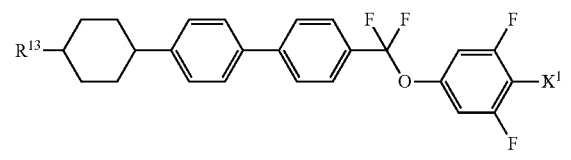
(7-33)
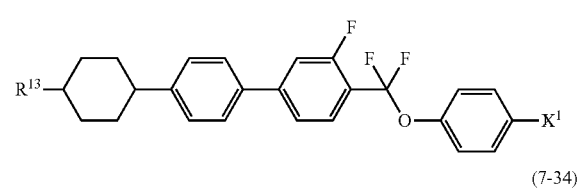
(7-34)
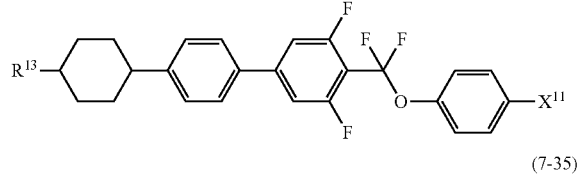
(7-35)
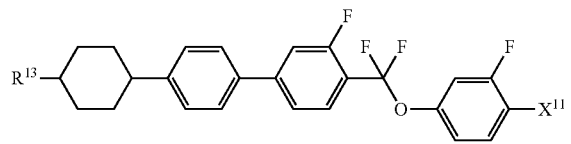
-continued
(7-36)
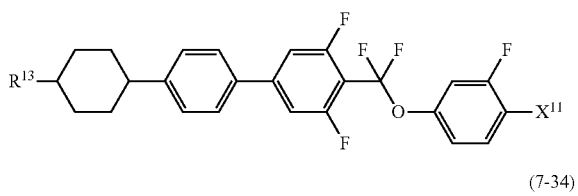
(7-34)
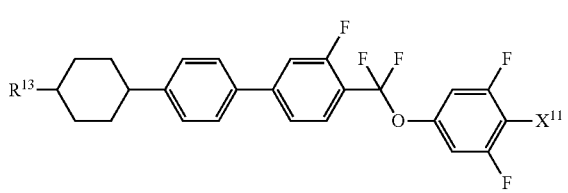
(7-38)
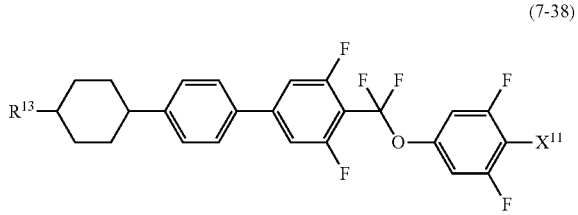
Formula 44
(7-39)
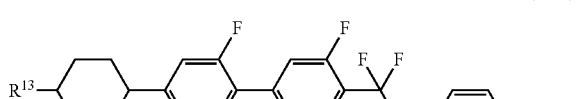
(7-40)
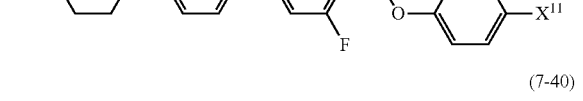
(7-41)
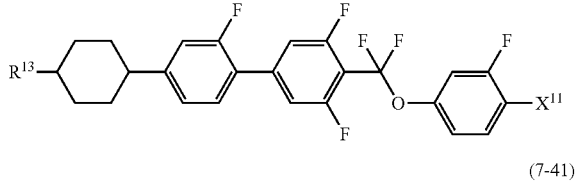
(7-42)
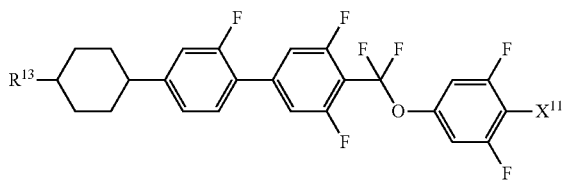
(7-43)
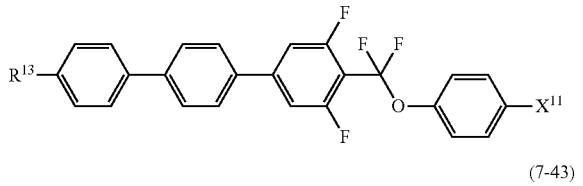
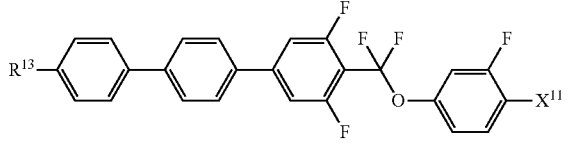

(7-44)
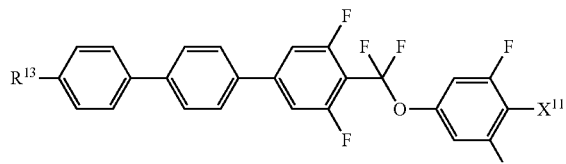

(7-45)
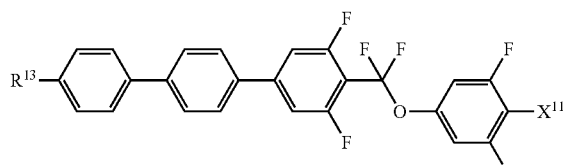

(7-46)
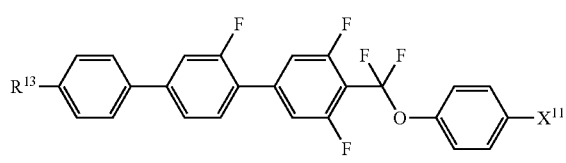

(7-47)
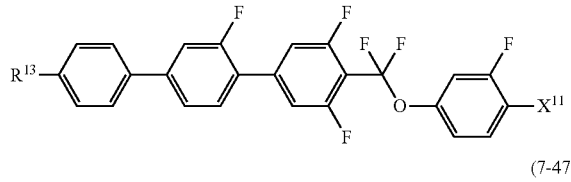

(7-48)
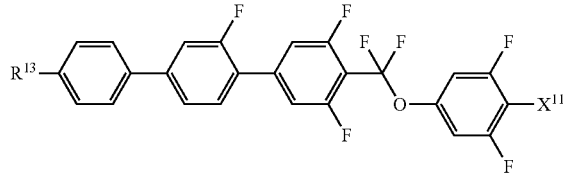

(7-49)
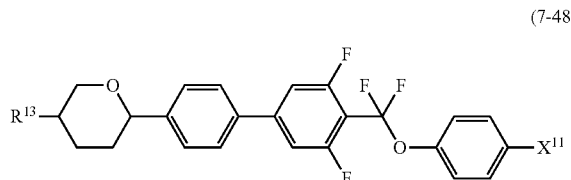

(7-50)
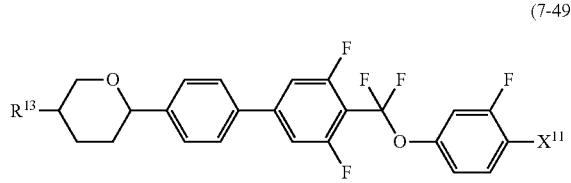

(7-51)
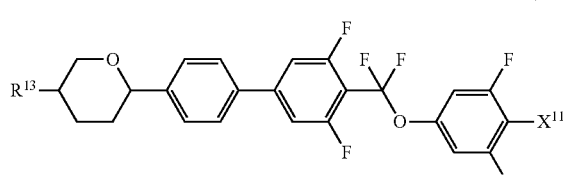

(7-52)
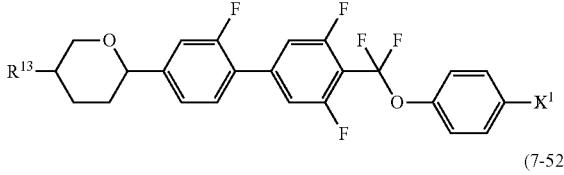

(7-53)
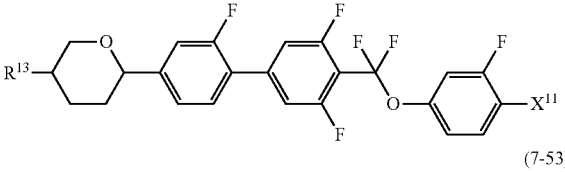

(7-54)
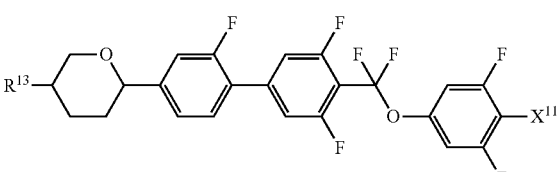

(7-55)
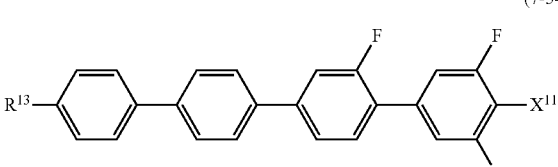

(7-56)
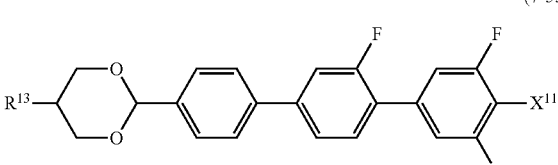

(7-57)
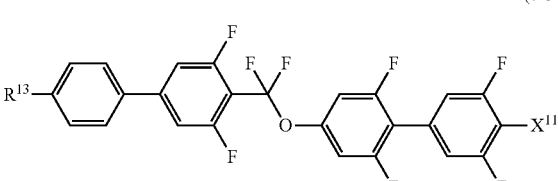

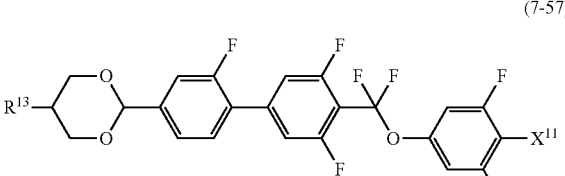

The liquid crystal compound represented by formulas (5) to (7) each has positive dielectric anisotropy, and superb stability to heat and light, and therefore is used when a composition for an IPS mode, an FFS mode, an OCB mode or the like is prepared. A content of the compounds each is suitably in the range of 1 to 99% by weight, preferably in the range of 10 to 97% by weight, and further preferably in the range of 40 to 95% by weight, based on the weight of the liquid crystal composition. When the compounds each are added to a composition having negative dielectric anisotropy, a content thereof is preferably 30% by weight or less based on the weight of the liquid crystal composition. An elastic constant of the composition can be adjusted, and a voltage-transmittance curve of the device can be adjusted, by adding the compounds thereto.

2.2 Liquid Crystal Compound Represented by Formula (8)

Formula 45

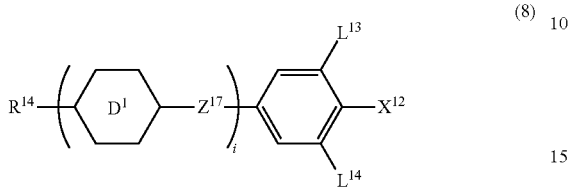

(8)

In formula (8), $R^{14}$ is alkyl having 1 to 10 carbons or alkenyl having 2 to 10 carbons, and in $R^{14}$, at least one piece of —CH$_2$— may be replaced by —O—, and at least one hydrogen may be replaced by fluorine;

$X^{12}$ is —C≡N or —C≡C—C≡N;

ring $D^1$ is 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;

$Z^{17}$ is a single bond, —(CH$_2$)$_2$—, —C≡C—, —COO—, —CF$_2$O—, —OCF$_2$— or —CH$_2$O—;

$L^{13}$ and $L^{14}$ are independently hydrogen or fluorine; and i is 1, 2, 3 or 4.

The liquid crystal compound represented by formula (8) is a compound in which a right-terminal group is —C≡N or —C≡C—C≡N. Preferred examples thereof include compounds (8-1) to (8-64). In the formulas, $R^{14}$ and $X^{12}$ are defined in the same manner as in formula (8).

Formula 46

(8-1)

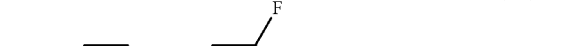
(8-2)

(8-3)

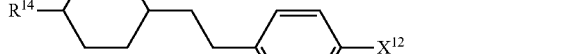
(8-4)

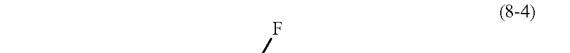
(8-5)

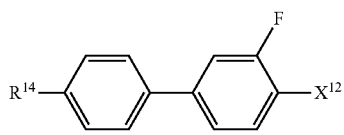
(8-6)

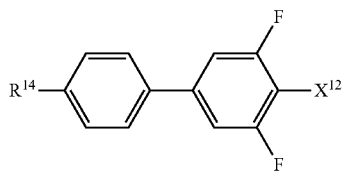
(8-7)

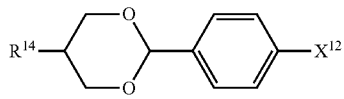
(8-8)

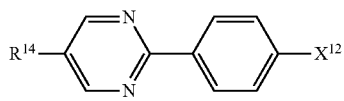
(8-9)

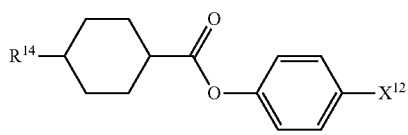
(8-10)

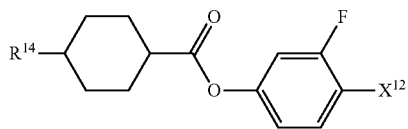
(8-11)

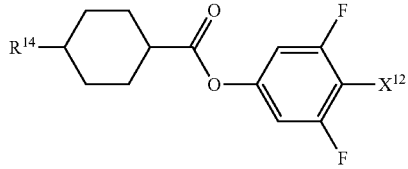
(8-12)

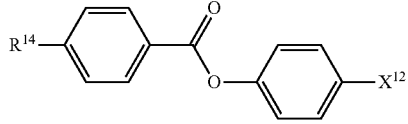
(8-13)

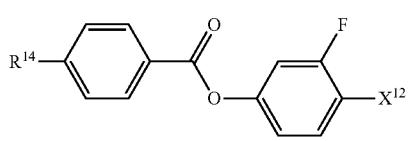
(8-14)

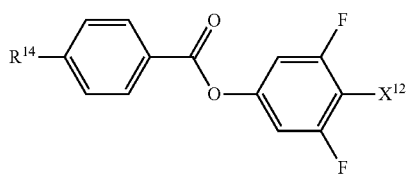
(8-15)

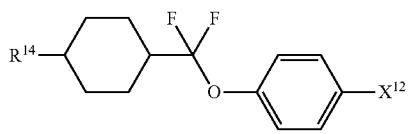
(8-16)

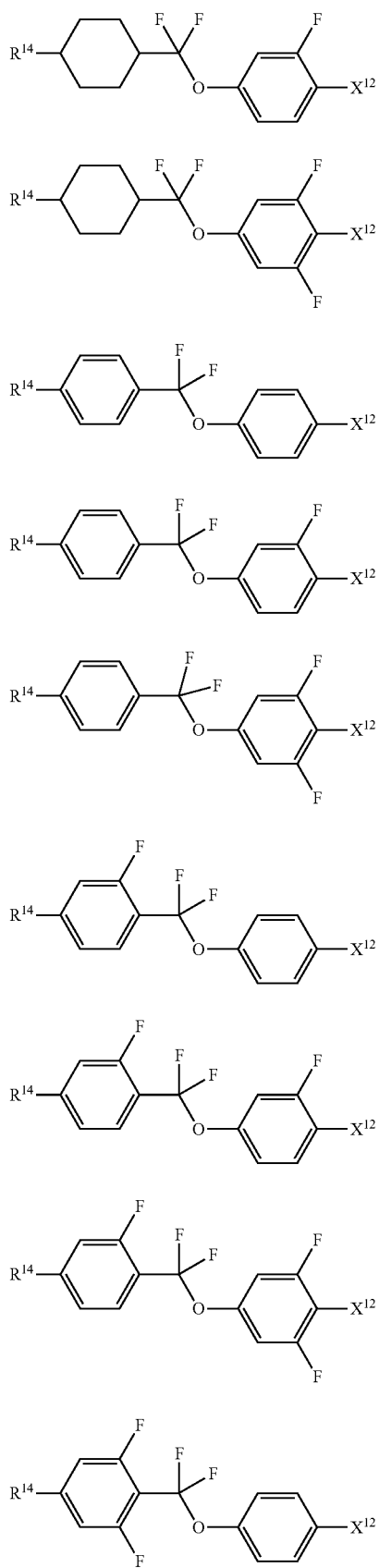
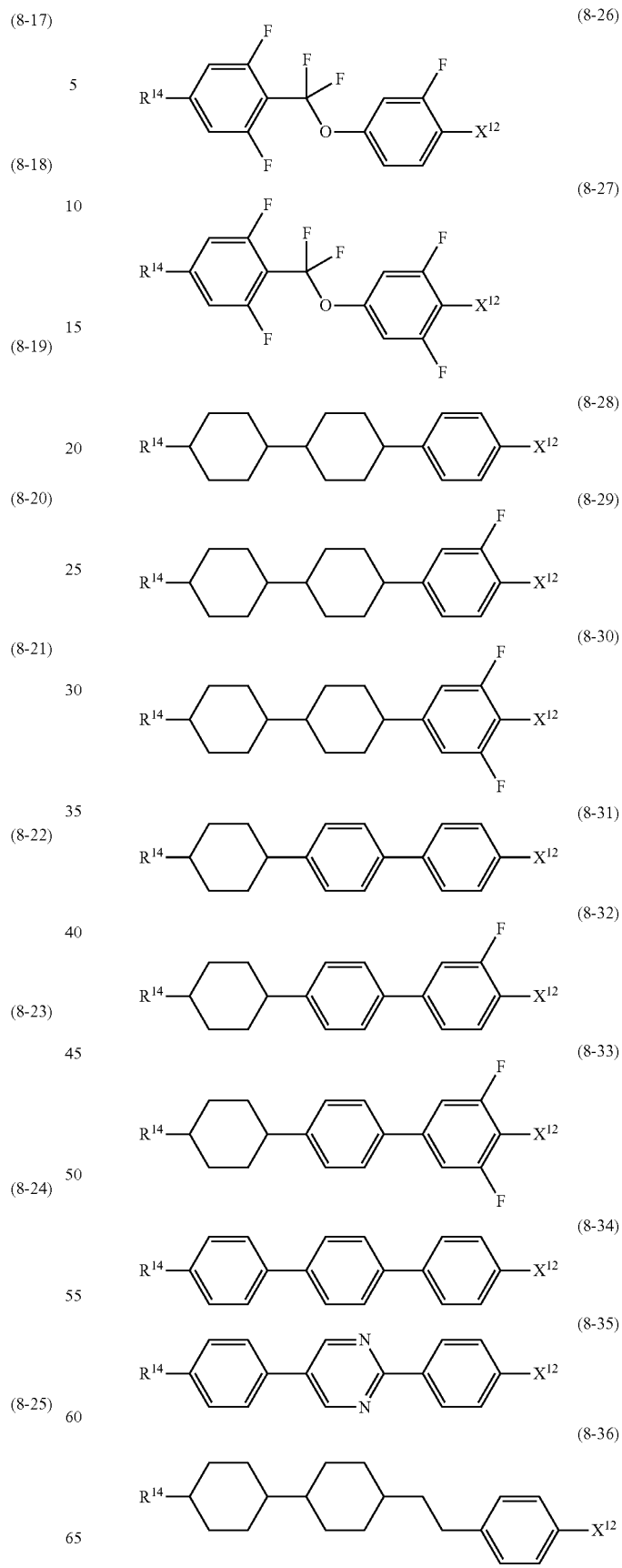

(8-37)
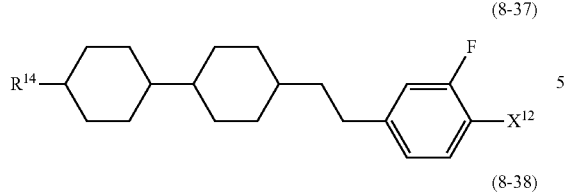
(8-38)
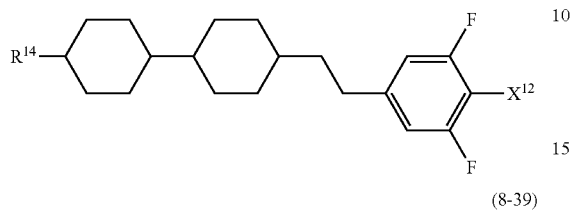
(8-39)
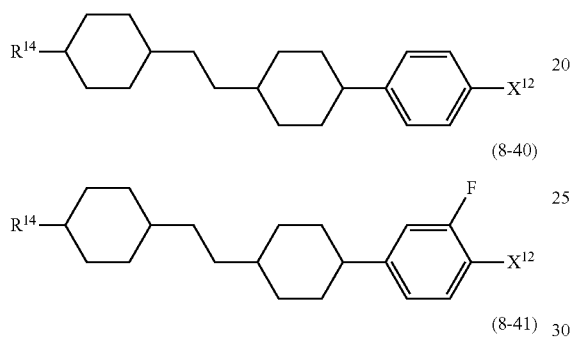
(8-40)
(8-41)
Formula 47
(8-42)
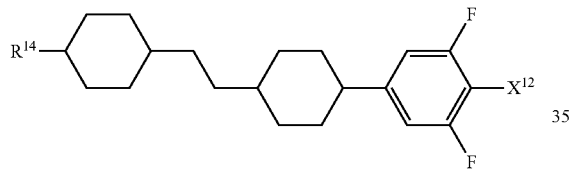
(8-43)
(8-44)
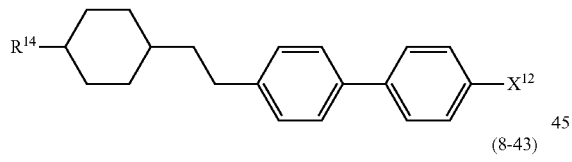
(8-45)
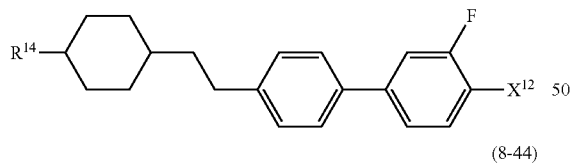
(8-46)
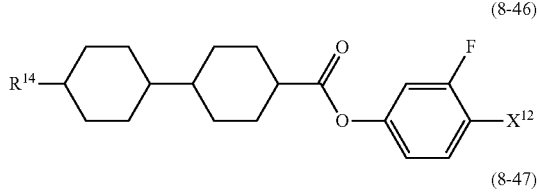
(8-47)
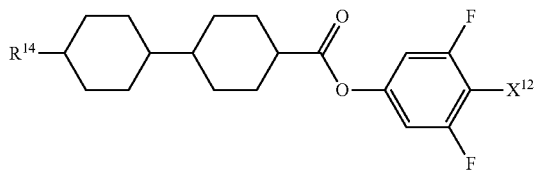
(8-48)
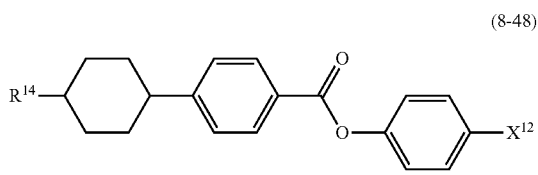
(8-49)
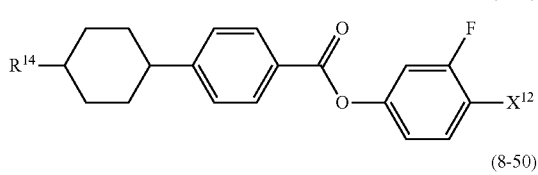
(8-50)
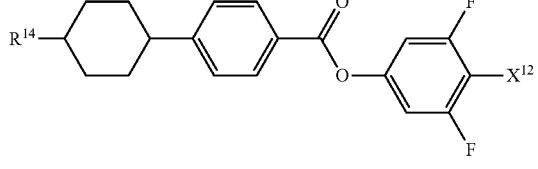
(8-51)
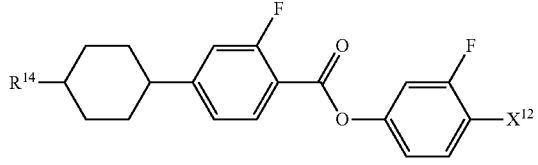
(8-52)
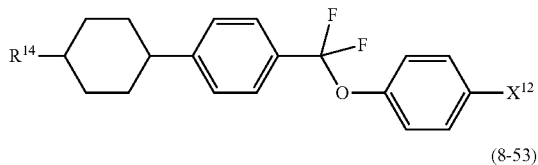
(8-53)
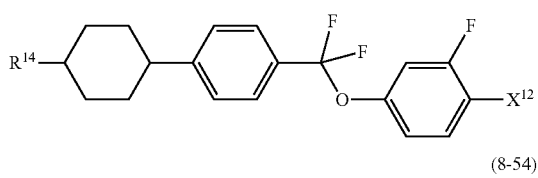
(8-54)
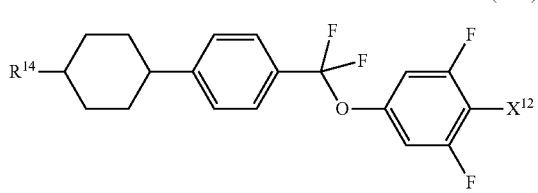

(8-55)
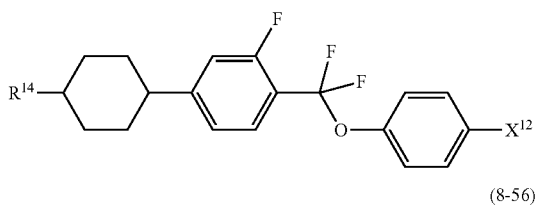

(8-56)
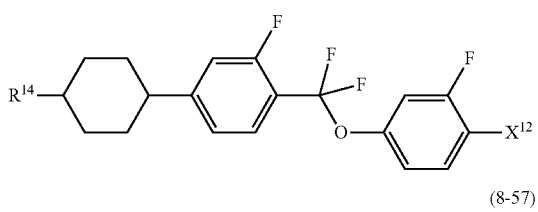

(8-57)
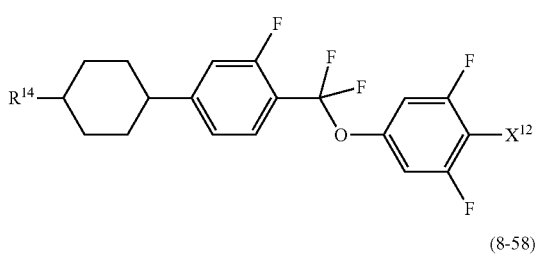

(8-58)
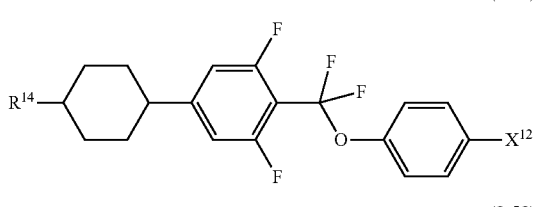

(8-59)
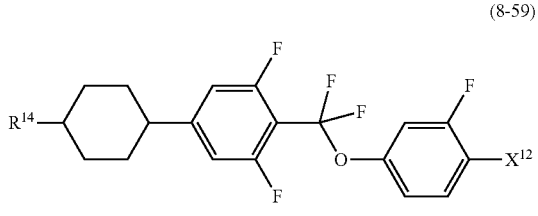

(8-60)
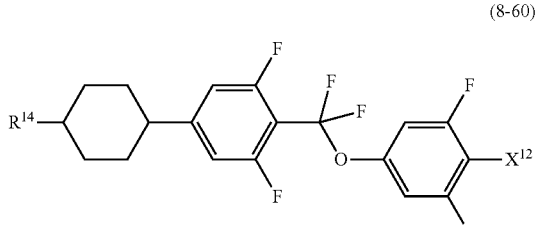

(8-61)
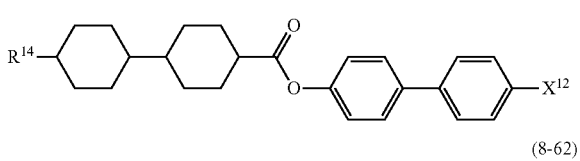

(8-62)
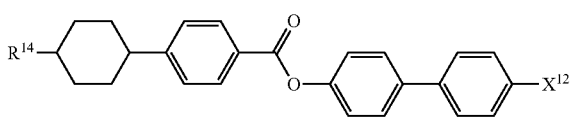

(8-63)
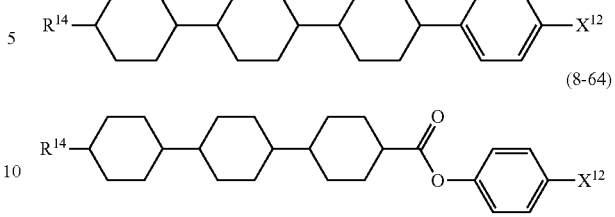

(8-64)
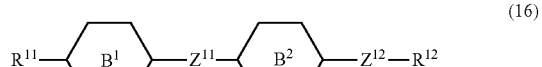

The liquid crystal compound represented by formula (8) has positive dielectric anisotropy and a value thereof is large, and therefore is mainly used when a composition for a TN mode or the like is prepared. Dielectric anisotropy of the composition can be increased by adding the compound thereto. The compound is effective in extending the temperature range of the liquid crystal phase, adjusting the viscosity or adjusting the optical anisotropy. The compound is also useful for adjustment of the voltage-transmittance curve of the device.

When the composition for the TN mode or the like is prepared, a content of the liquid crystal compound represented by formula (8) is suitably in the range of 1 to 99% by weight, preferably in the range of 10 to 97% by weight, and further preferably in the range of 40 to 95% by weight, based on the weight of the liquid crystal composition. When the compound is added to the composition having negative dielectric anisotropy, a content thereof is preferably 30% by weight or less based on the weight of the liquid crystal composition. The elastic constant of the composition can be adjusted, and the voltage-transmittance curve of the device can be adjusted, by adding the compound thereto.

2.3 Liquid Crystal Compound Represented by Formulas (16) to (18)

Formula 48

(16)
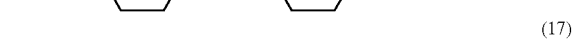

(17)
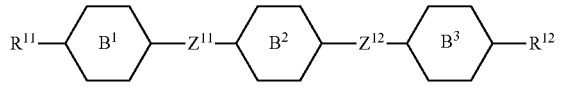

(18)
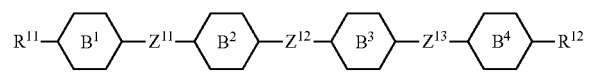

In formulas (16) to (18), $R^{11}$ and $R^{12}$ are independently alkyl having 1 to 10 carbons, alkoxy having 1 to 10 carbons, alkoxyalkyl having 2 to 10 carbons, alkenyl having 2 to 10 carbons or difluorovinyl, and in $R^{11}$ and $R^{12}$, at least one piece of —CH$_2$— may be replaced by —O—, and at least one hydrogen may be replaced by fluorine;

ring $B^1$, ring $B^2$, ring $B^3$ and ring $B^4$ are independently 1,4-cyclohexylene, 1,4-phenylene, 2-fluoro-1,4-phenylene, 2,5-difluoro-, 4-phenylene or pyrimidine-2,5-diyl; and $Z^{11}$, $Z^{12}$ and $Z^{13}$ are independently a single bond, —(CH$_2$)2-, —CH=CH—, —C≡C— or —COO—.

The liquid crystal compound represented by formulas (16) to (18) each is a compound in which two terminal groups are alkyl or the like. Preferred examples thereof include compounds (16-1) to (16-11), compounds (17-1) to (17-19) and compounds (18-1) to (18-7). In the formulas, $R^{11}$ and $R^{12}$ are defined in the same manner as in formulas (16) to (18).
Formula 49
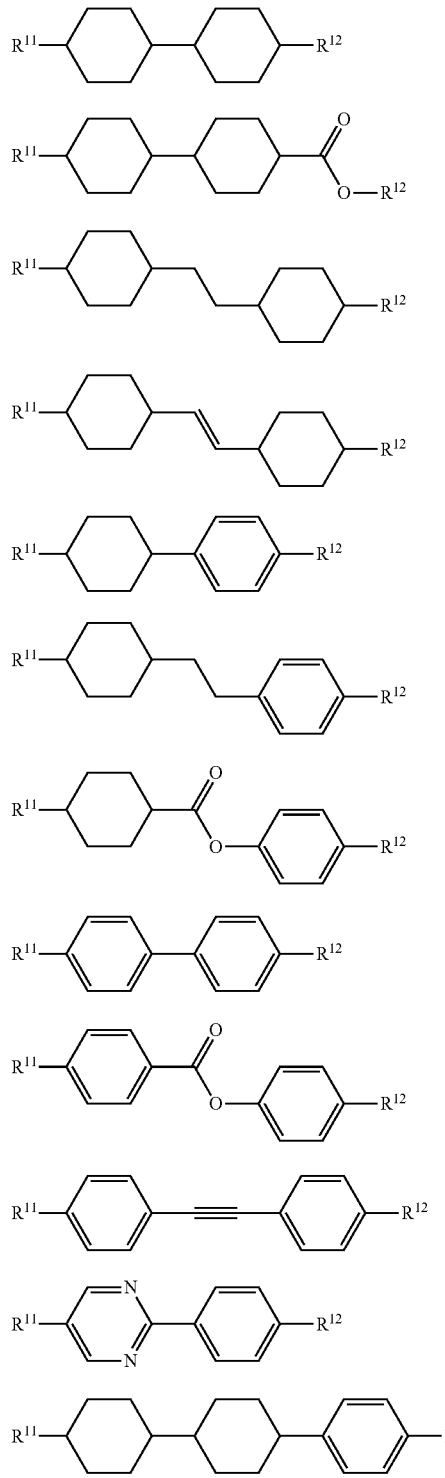
-continued
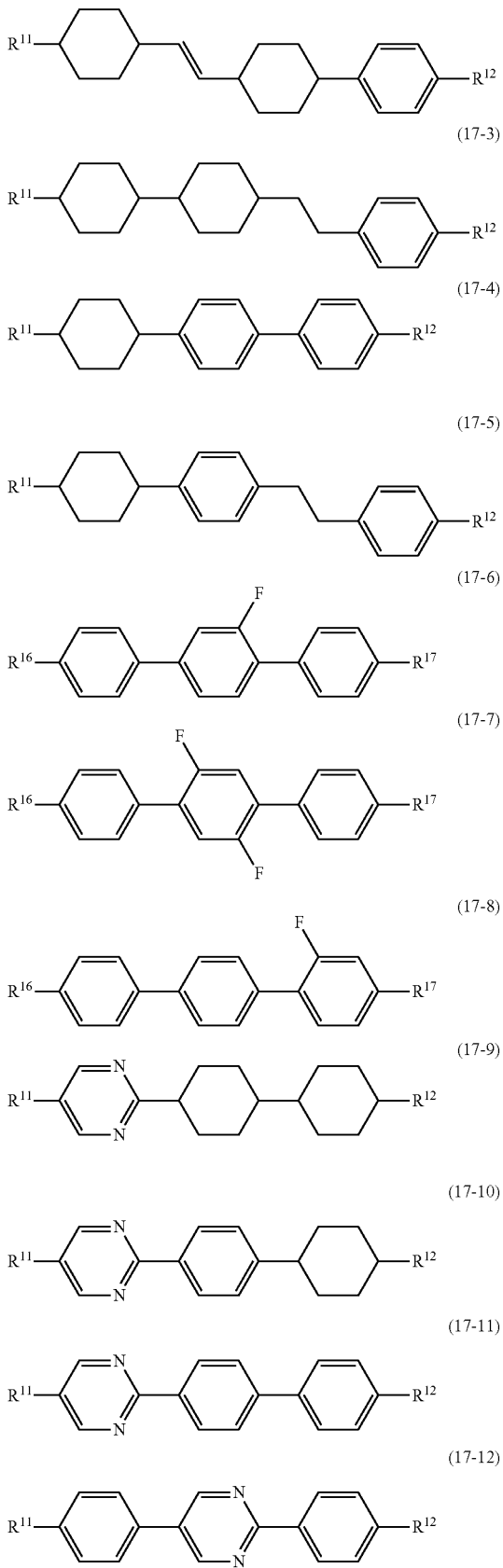

-continued (17-13) 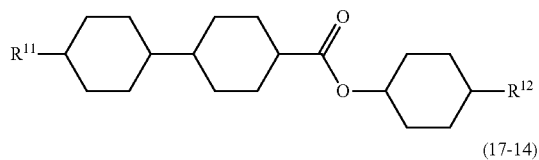

(17-14) 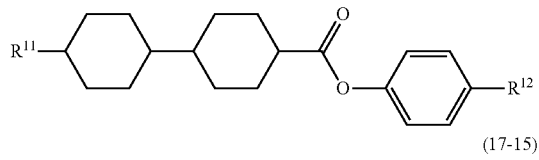

(17-15) 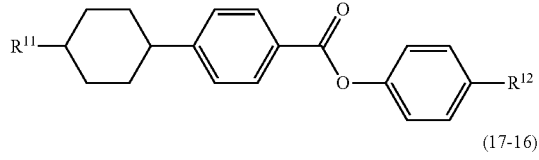

(17-16) 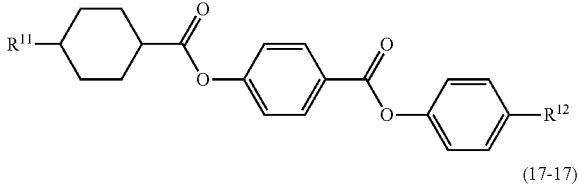

(17-17) 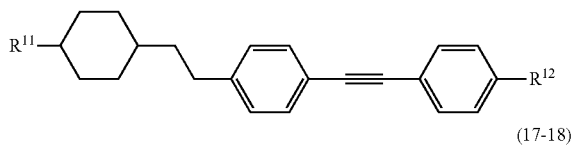

(17-18) 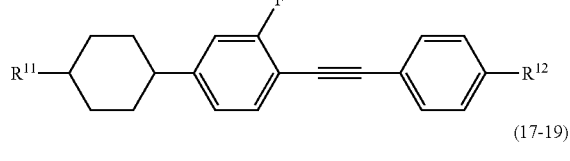

(17-19) 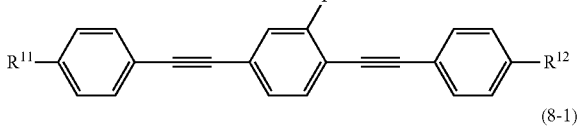

(8-1) 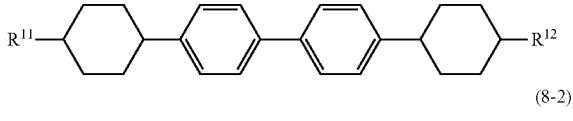

(8-2) 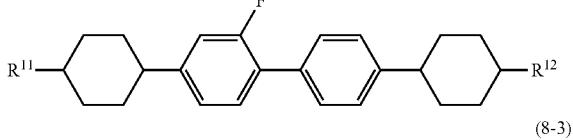

(8-3) 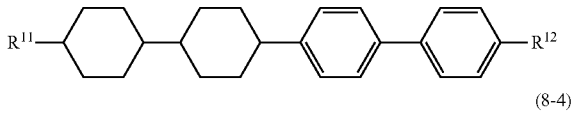

(8-4) 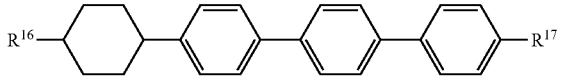

-continued (8-5) 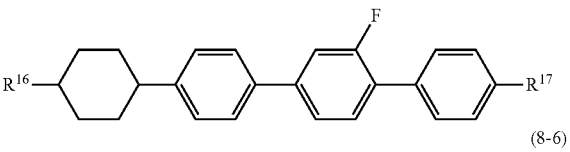

(8-6) 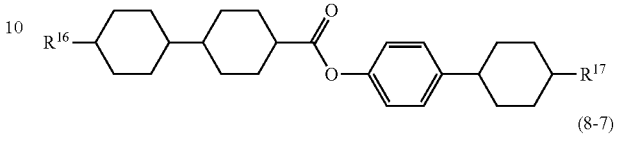

(8-7) 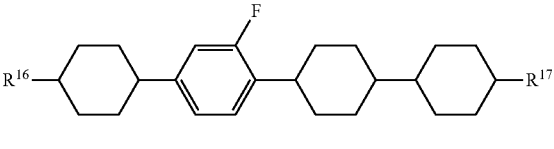

The liquid crystal compound represented by formulas (16) to (18) each has a small absolute value of dielectric anisotropy, and therefore is a compound close to neutrality. The compound represented by formula (16) is mainly effective in decreasing the viscosity or adjusting the optical anisotropy. The compound represented by formula (17) and the compound represented by formula (18) are effective in extending the temperature range of the nematic phase by increasing the maximum temperature, or in adjusting the optical anisotropy.

Accordingly as a content of the liquid crystal compound represented by formulas (16) to (18) each is increased, the dielectric anisotropy of the composition is decreased, but the viscosity is decreased. Thus, as long as a desired value of threshold voltage of the device is met, the content is preferably as large as possible. When a composition for the IPS mode or the like is prepared, a content of the liquid crystal compound represented by formulas (16) to (18) each is preferably 30% by weight or more, and further preferably 40% by weight or more, based on the weight of the liquid crystal composition.

3. Polymerizable Compound

The polymerizable compound is added for the purpose of forming the polymer in the liquid crystal composition. The polymerizable compound is polymerized by irradiation with ultraviolet light while voltage is applied between electrodes, and thus the polymer is formed in the liquid crystal composition. An initial state of alignment can be stabilized according to the method, and therefore a liquid crystal display device in which a response time is shortened and image persistence is improved can be obtained. Specific examples of a preferred polymerizable compound include acrylate, methacrylate, a vinyl compound, a vinyloxy compound, propenyl ether, an epoxy compound (oxirane, oxetane) and vinyl ketone. Further preferred examples thereof include a compound having at least one acryloyloxy and a compound having at least one methacryloyloxy. Still further preferred examples also include a compound having both acryloyloxy and methacryloyloxy. A specific polymerizable compound will be described below.

3.1 Polymerizable Compound Represented by Formula (19)

Formula 50

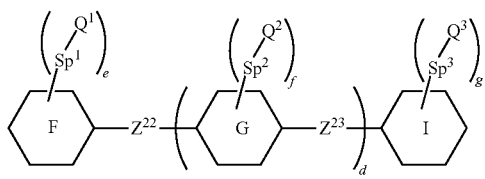

(19)

In formula (19), ring F and ring I are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one hydrogen may be independently replaced by halogen, alkyl having 1 to 12 carbons, alkoxy having 1 to 12 carbons, or alkyl having 1 to 12 carbons in which at least one hydrogen is replaced by halogen;

ring G is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one hydrogen may be independently replaced by halogen, alkyl having 1 to 12 carbons, alkoxy having 1 to 12 carbons, or alkyl having 1 to 12 carbons in which at least one hydrogen is replaced by halogen;

$Z^{22}$ and $Z^{23}$ are independently a single bond or alkylene having 1 to 10 carbons, and in $Z^{22}$ and $Z^{23}$, at least one piece of —$CH_2$— may be independently replaced by —O—, —CO—, —COO— or —OCO—, and at least one piece of —$CH_2CH_2$— may be independently replaced by —CH=CH—, —C($CH_3$)=CH—, —CH=C($CH_3$)— or —C($CH_3$)=C($CH_3$)—, and in the groups, at least one hydrogen may be replaced by fluorine or chlorine;

$Q^1$, $Q^2$ and $Q^3$ are independently a polymerizable group;

$Sp^1$, $Sp^2$ and $Sp^3$ are independently a single bond or alkylene having 1 to 10 carbons, and in $Sp^1$, $Sp^2$ and $Sp^3$, at least one piece of —$CH_2$— may be independently replaced by —O—, —COO—, —OCO— or —OCOO—, and at least one piece of —$CH_2CH_2$— may be independently replaced by —CH=CH— or —C≡C—, and in the groups, at least one hydrogen may be replaced by fluorine or chlorine;

d is 0, 1 or 2; and e, f and g are independently 0, 1, 2, 3 or 4, and a sum of e, f and g is 1 or more.

In formula (19), $Q^1$, $Q^2$ and $Q^3$ are preferably independently a polymerizable group represented by any one of formulas (Q-1) to (Q-5).

Formula 51

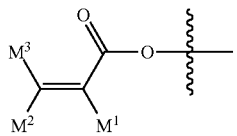

(Q-1)

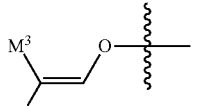

(Q-2)

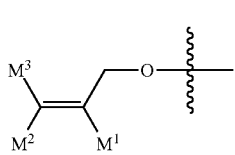

(Q-3)

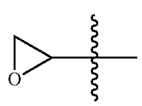

(Q-4)

(Q-5)

In formulas (Q-1) to (Q-5), $M^1$, $M^2$ and $M^3$ are independently hydrogen, fluorine, alkyl having 1 to 5 carbons, or alkyl having 1 to 5 carbons in which at least one hydrogen is replaced by halogen.

Specific examples of a preferred polymerizable compound represented by formula (19) include polymerizable compound (19-1) to (19-7):

Formula 52

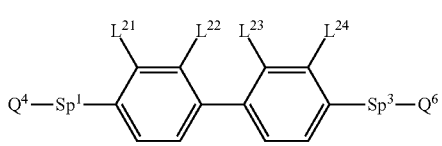

(19-1)

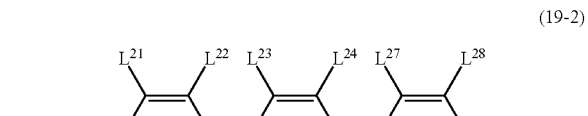

(19-2)

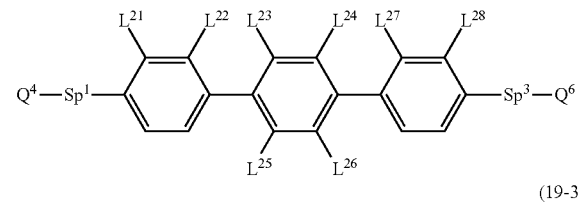

(19-3)

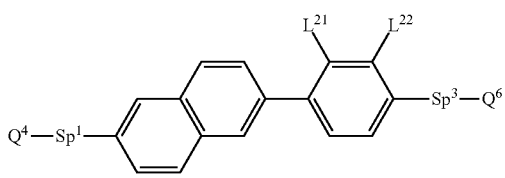

(19-4)

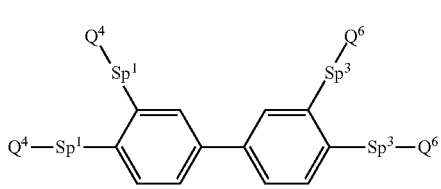

-continued

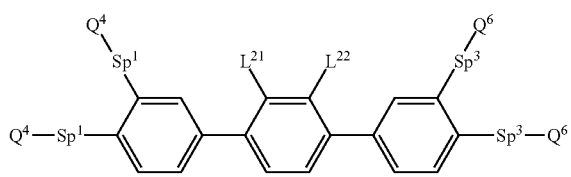
(19-5)

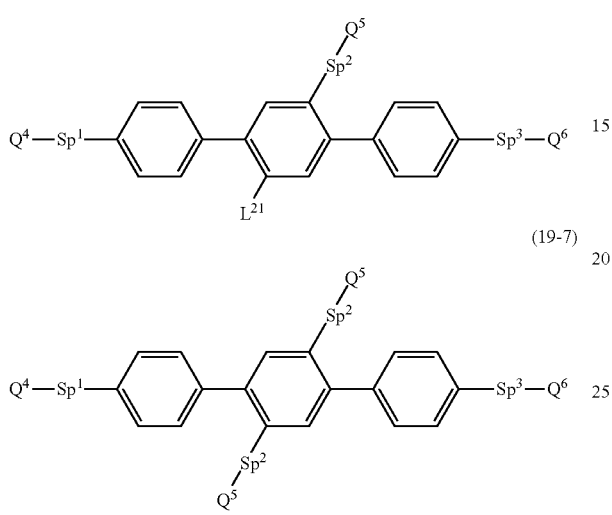
(19-6)
(19-7)

—CH=CH— or —C≡C—, and in the groups, at least one hydrogen may be independently replaced by fluorine or chlorine; and $Q^4$, $Q^5$ and $Q^6$ are independently a polymerizable group represented by any one of formulas (Q-1) to (Q-3), in which $M^1$, $M^2$ and $M^3$ are independently hydrogen, fluorine, alkyl having 1 to 5 carbons, or alkyl having 1 to 5 carbons in which at least one hydrogen is replaced by halogen:

Formula 53

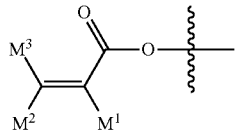
(Q-1)

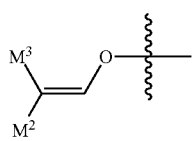
(Q-2)

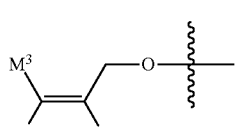
(Q-3)

In formulas (19-1) to (19-7),
$L^{21}$, $L^{22}$, $L^{23}$, $L^{24}$, $L^{25}$, $L^{26}$, $L^{27}$ and $L^{28}$ are independently hydrogen, fluorine or methyl;
$Sp^1$, $Sp^2$ and $Sp^3$ are independently a single bond or alkylene having 1 to 10 carbons, and in $Sp^1$, $Sp^2$ and $Sp^3$, at least one piece of —$CH_2$— may be independently replaced by —O—, —COO—, —OCO— or —OCOO—, and at least one piece of —$(CH_2)_2$— may be independently replaced by Specific examples of a further preferred polymerizable compound represented by formula (19) include polymerizable compound (M-1) to (M-17). In the compounds, $R^{25}$ to $R^{31}$ are independently hydrogen or methyl; v and x are independently 0 or 1; t and u are independently an integer from 1 to 10; s is 0 or 1; and $L^{21}$ to $L^{26}$ are independently hydrogen or fluorine, and $L^{27}$ and $L^{28}$ are independently hydrogen, fluorine or methyl.

Formula 54

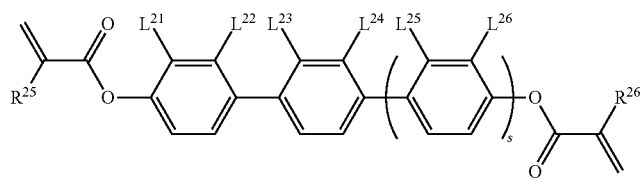
(M-1)

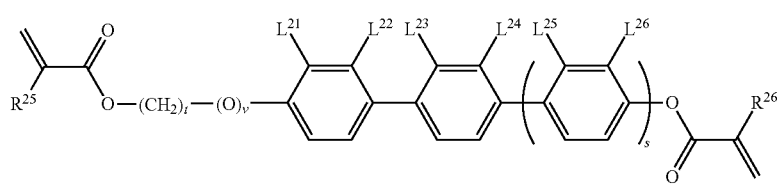
(M-2)

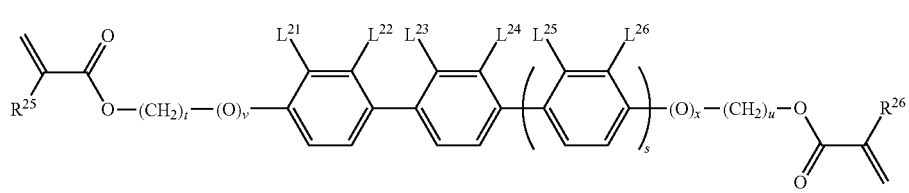
(M-3)

(M-4) 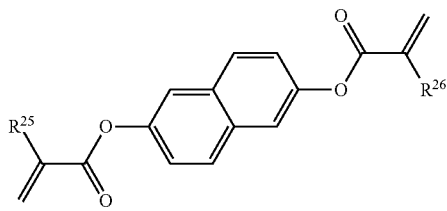
(M-5) 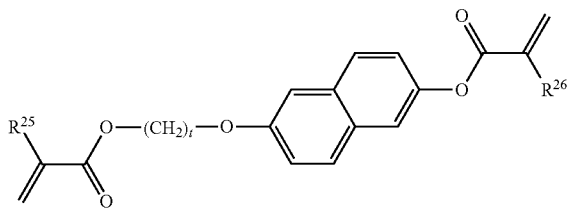
(M-6) 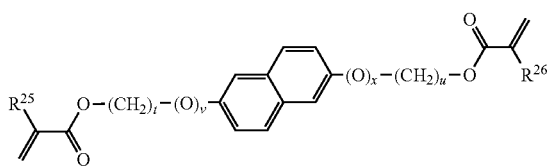
(M-7) 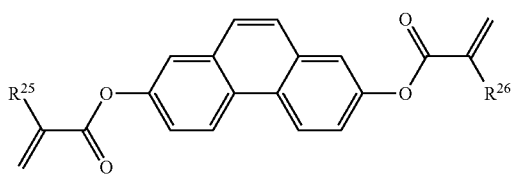
(M-8) 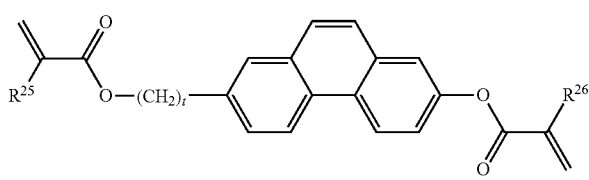
(M-9) 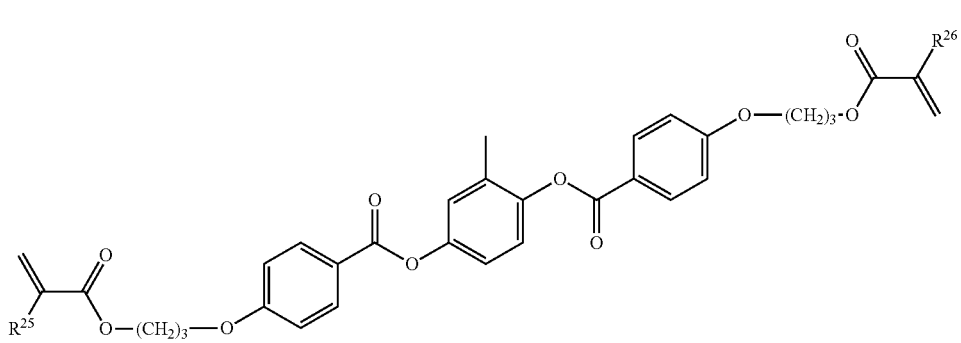
(M-10) 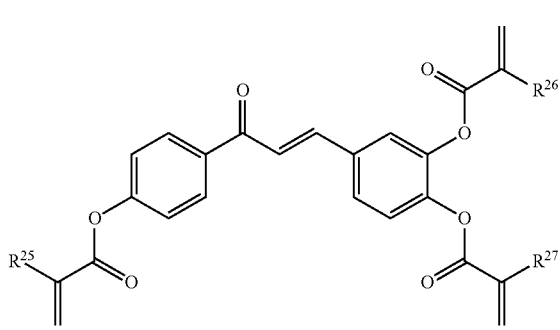
Formula 55
(M-11) 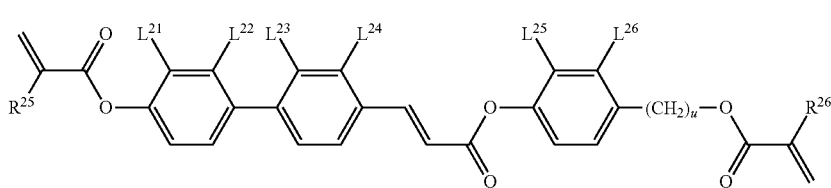

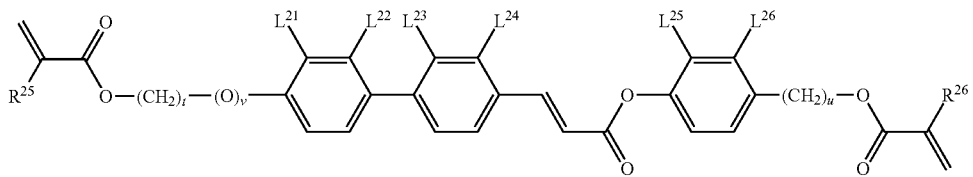

(M-12)

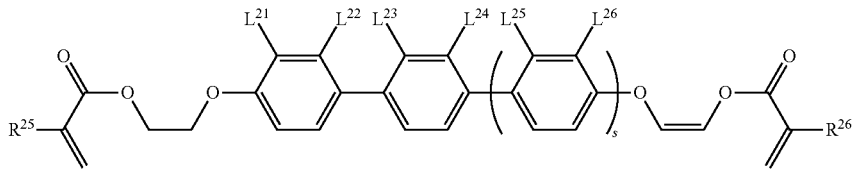

(M-13)

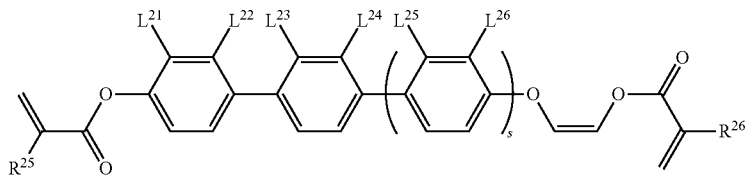

(M-14)

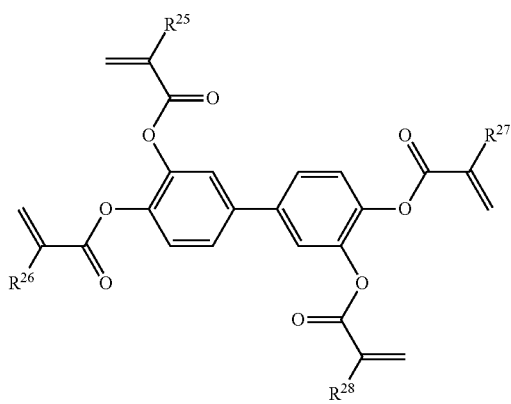

(M-15)

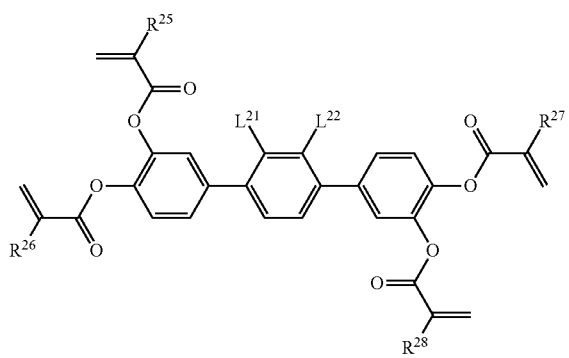

(M-16)

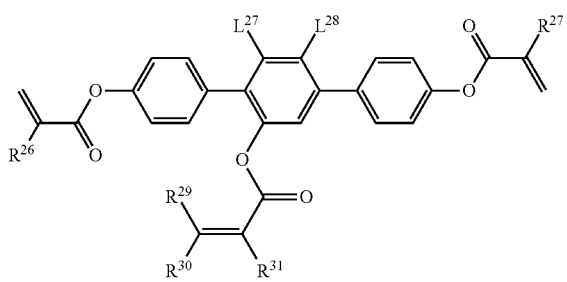

(M-17)

4. Additive
4.1 Polymerization Initiator

The polymerizable compound can be rapidly polymerized by adding the polymerization initiator. An amount of a remaining polymerizable compound can be decreased by optimizing a reaction temperature. Specific examples of a photoradical polymerization initiator include TPO, 1173 and 4265 from Darocur series of BASF SE, and 184, 369, 500, 651, 784, 819, 907, 1300, 1700, 1800, 1850 and 2959 from Irgacure series thereof.

Additional examples of the photoradical polymerization initiator include 4-methoxyphenyl-2,4-bis(trichloromethyl) triazine, 2-(4-butoxystyryl)-5-trichloromethyl-1,3,4-oxadiazole, 9-phenylacridine, 9,10-benzphenazine, a benzophenone-Michler's ketone mixture, a hexaarylbiimidazole-mercaptobenzimidazole mixture, 1-(4-isopropylphenyl)-2-hydroxy-2-methylpropane-1-one, benzyl dimethyl ketal, 2-methyl-1-[4-(methylthio)phenyl]-2-morpholinopropane-1-one, a mixture of 2,4-diethylxanthone and methyl p-dimethylaminobenzoate, and a mixture of benzophenone and methyltriethanolamine.

After the photoradical polymerization initiator is added to the liquid crystal composition, polymerization can be performed by irradiation with ultraviolet light while an electric field is applied thereto. However, an unreacted polymerization initiator or a decomposition product of the polymerization initiator may cause a poor display such as the image persistence in the device. In order to prevent such occurrence, photopolymerization may be performed with no addition of the polymerization initiator. A preferred wavelength of irradiation light is in the range of 150 to 500 nanometers. A further preferred wavelength is in the range of 250 to 450 nanometers, and a most preferred wavelength is in the range of 300 to 400 nanometers.

4.2 Polymerization Inhibitor

Upon storing the polymerizable compound, the polymerization inhibitor may be added thereto for preventing polymerization. The polymerizable compound is ordinarily added to the composition without removing the polymerization inhibitor. Specific examples of the polymerization inhibitor include hydroquinone, a hydroquinone derivative such as methylhydroquinone, 4-t-butylcatechol, 4-methoxyphenol and phenothiazine.

4.3 Optically Active Compound

The optically active compound is effective in inducing a helical structure in liquid crystal molecules to give a required twist angle, thereby preventing a reverse twist. A helical pitch can be adjusted by adding the optically active compound. Two or more optically active compounds may be added for the purpose of adjusting temperature dependence of the helical pitch. Specific examples of a preferred optically active compound include compounds (Op-1) to (Op-18). In compound (Op-18), ring J is 1,4-cyclohexylene or 1,4-phenylene, and $R^{28}$ is alkyl having 1 to 10 carbons.

Formula 56

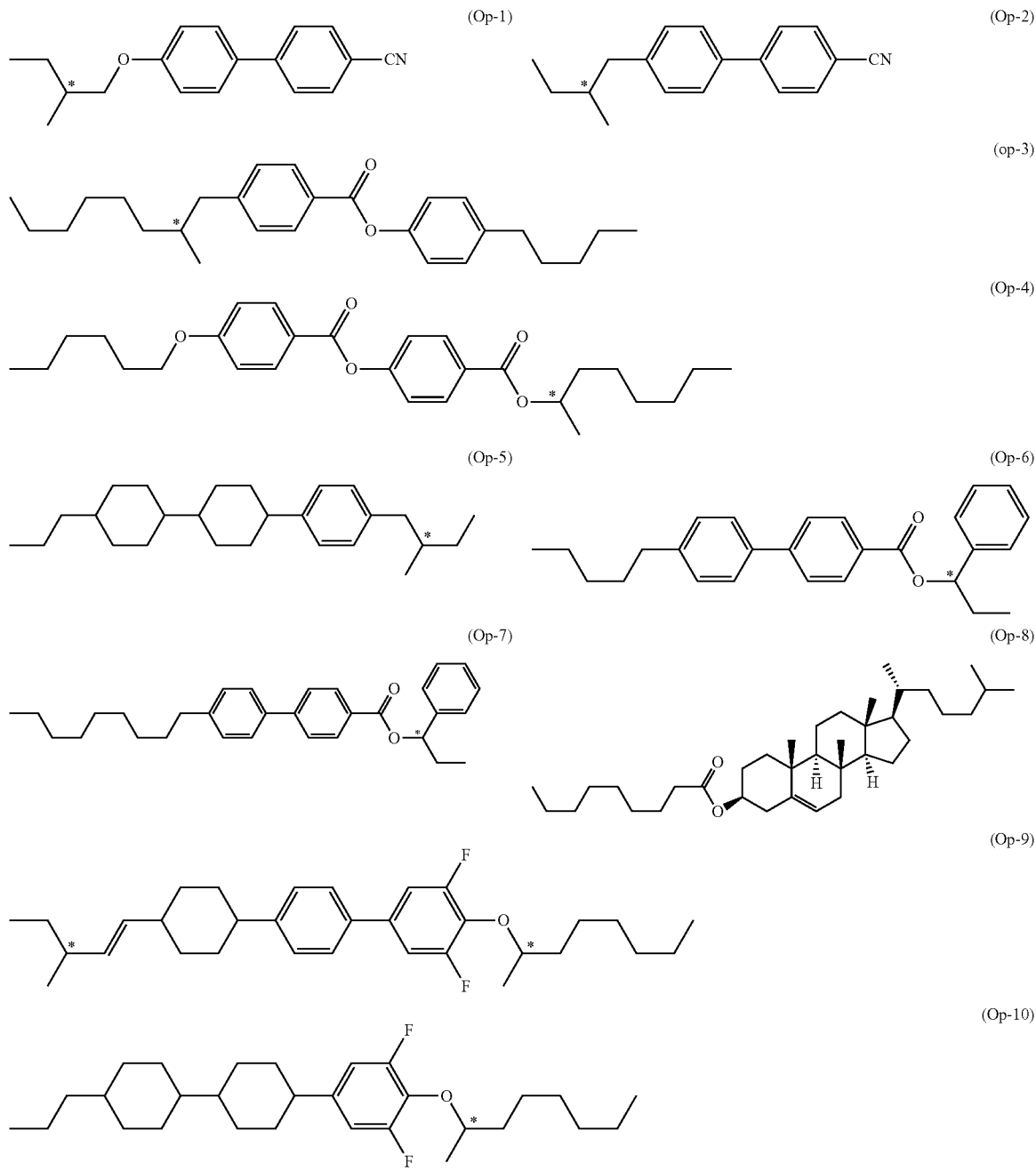

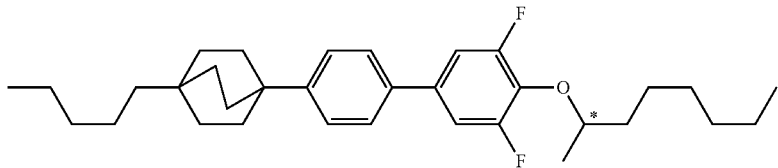
(Op-11)

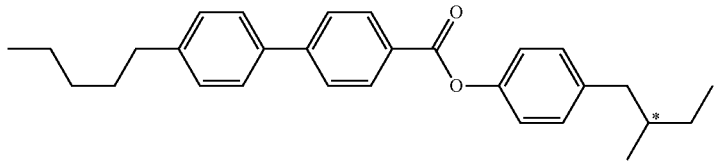
(Op-12)

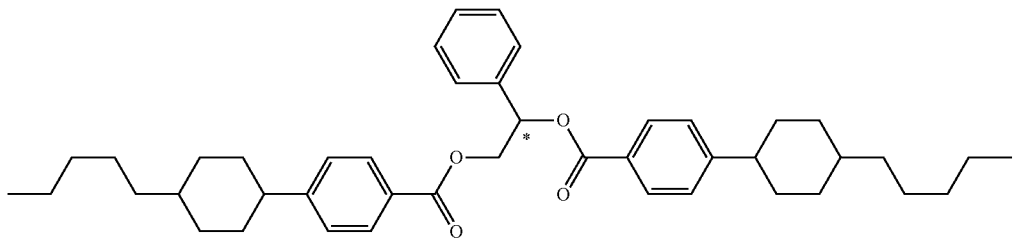
(Op-13)

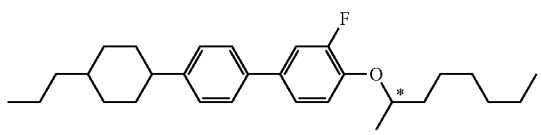
(Op-15)

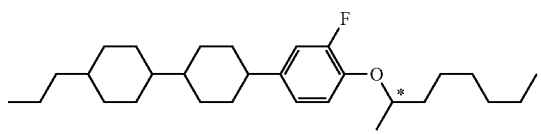
(Op-14)

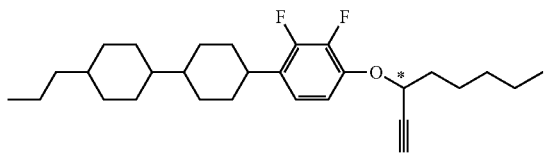
(Op-16)

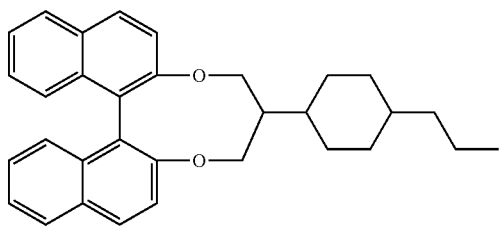
(Op-17)

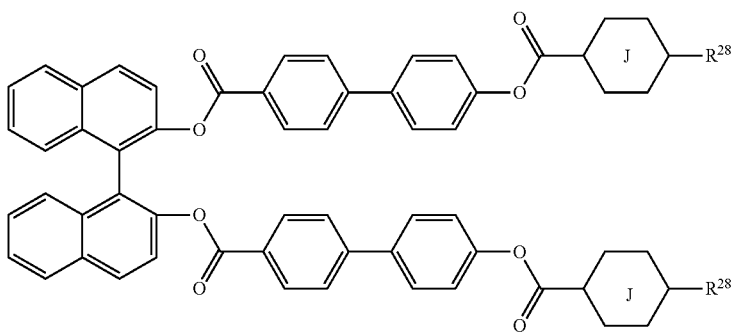
(Op-18)

4.4 Antioxidant, Ultraviolet Light Absorber, Light Stabilizer, Heat stabilizer, antifoaming agent The antioxidant is effective for maintaining a large voltage holding ratio. Specific examples of a preferred antioxidant include compounds (AO-1) and (AO-2); and IRGANOX 415, IRGANOX 565, IRGANOX 1010, IRGANOX 1035, IRGANOX 3114 and IRGANOX 1098 (trade names: BASF SE). The ultraviolet light absorber is effective for preventing a decrease of the maximum temperature. Specific examples of a preferred ultraviolet light absorber include a benzophenone derivative, a benzoate derivative and a triazole derivative. Specific examples thereof include compounds (AO-3) and (AO-4); TINUVIN 329, TINUVIN P, TINUVIN 326, TINUVIN 234, TINUVIN 213, TINUVIN 400, TINUVIN 328 and TINUVIN 99-2 (trade names: BASF SE); and 1,4-diazabicyclo[2.2.2]octane (DABCO).

The light stabilizer such as an amine having steric hindrance is preferred for maintaining the large voltage holding ratio. Specific examples of a preferred light stabilizer include compounds (AO-5) and (AO-6); and TINUVIN 144, TINUVIN 765 and TINUVIN 770DF (trade names: BASF SE). The heat stabilizer is also effective for maintaining the large voltage holding ratio, and preferred examples thereof include IRGAFOS 168 (trade name: BASF SE). The antifoaming agent is effective for preventing foam formation. Specific examples of a preferred antifoaming agent include dimethyl silicone oil and methylphenyl silicone oil.

Formula 57

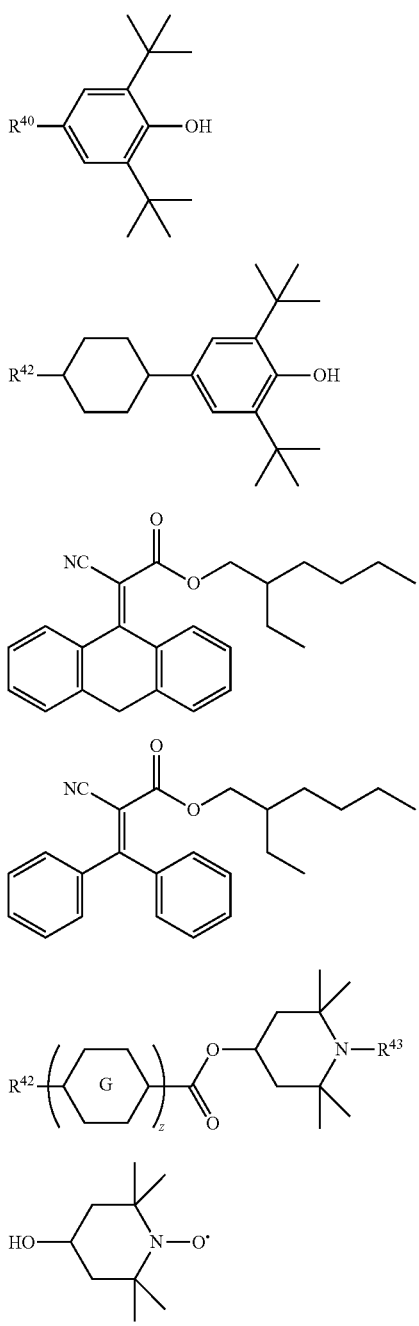

(AO-1)

(AO-2)

(AO-3)

(AO-4)

(AO-5)

(AO-6)

In compound (AO-1), $R^{40}$ is alkyl having 1 to 20 carbons, alkoxy having 1 to 20 carbons, —COOR$^4$ or —CH$_2$CH$_2$COOR$^{41}$, in which $R^{41}$ is alkyl having 1 to 20 carbons. In compounds (AO-2) and (AO-5), $R^{42}$ is alkyl having 1 to 20 carbons. In compound (AO-5), $R^{43}$ is hydrogen, methyl or O (oxygen radical), ring G is 1,4-cyclohexylene or 1,4-phenylene, and z is 1, 2 or 3.

5. Liquid Crystal Composition

The liquid crystal composition of the invention contains at least (1) the low molecular weight polar compound and (2) the liquid crystal compound. Moreover, the liquid crystal composition also contains (3) the polymerizable compound and (4) the additive such as the polymerization initiator, the polymerization inhibitor, the optically active compound, the antioxidant, the ultraviolet light absorber, the light stabilizer, the heat stabilizer and the antifoaming agent. The liquid crystal composition is prepared according to a publicly-known method. For example, the component compounds are mixed and dissolved in each other by heating.

When the liquid crystal composition of the invention is prepared, a kind of the liquid crystal compound is preferably selected by taking into account magnitude of positive or negative dielectric anisotropy, or the like. The composition in which the components are suitably selected has high maximum temperature, low minimum temperature, small viscosity, suitable optical anisotropy (namely, large optical anisotropy or small optical anisotropy), large positive or negative dielectric anisotropy, large specific resistance, stability to heat or ultraviolet light and a suitable elastic constant (namely, a large elastic constant or a small elastic constant).

A content of (1) the polar compound in the liquid crystal composition is 0.01 to 20% by weight, preferably 0.1 to 15% by weight, further preferably 0.3 to 10% by weight, and still further preferably 0.5 to 7% by weight.

However, the content of the polar compound is preferably determined in consideration of the positive-phase negative-phase CV product thereof. More specifically, the content is preferably adjusted in such a manner that the total positive-phase negative-phase CV product (positive-phase negative-phase CV product×content/100), which is the product of the positive-phase negative-phase CV product of the polar compound and the content thereof, becomes 0.01 or more. A term "total positive-phase negative-phase CV product" means, when plural kinds of the polar compounds are contained in the liquid crystal composition, a sum of respective total positive-phase negative-phase CV products of the polar compounds, and a sum of the positive-phase negative-phase CV products of the polar compounds existing in the liquid crystal composition.

The total positive-phase negative-phase CV product of the polar compound in the liquid crystal composition of the invention is preferably 0.01 or more, further preferably 0.05 to 20, still further preferably 0.1 to 10, and particularly preferably 1.0 to 6.0.

6. Liquid Crystal Display Device

The liquid crystal composition can be used in the liquid crystal display device having an operating mode such as a phase change (PC) mode, a twisted nematic (TN) mode, a super twisted nematic (STN) mode, an electrically controlled birefringence (ECB) mode, an optically compensated bend (OCB) mode, an in-plane switching (IPS) mode, a fringe field switching (FFS) mode and a field-induced photoreactive alignment (FPA) mode and driven by an active matrix mode. The composition can also be used in the liquid crystal display device having the operating mode such as the PC mode, the TN mode, the STN mode, the ECB mode, the OCB mode, the IPS mode, the FFS mode and the FPA mode, and driven by a passive matrix mode. The devices can be applied to any of a reflective type, a transmissive type and a transflective type.

The composition can also be used in a nematic curvilinear aligned phase (NCAP) device prepared by microencapsulating a nematic liquid crystal, and a polymer dispersed liquid crystal display device (PDLCD) and a polymer network liquid crystal display device (PNLCD) in which a three-dimensional network-polymer is formed in the liquid crystal. When an amount of adding the polymerizable compound is about 10% by weight or less based on the weight of the liquid crystal composition, the liquid crystal display device having the PS mode can be prepared. A preferred proportion is in the range of about 0.1 to about 2% by weight. A further preferred proportion is in the range of about 0.2 to about 1.0% by weight. The device having the PS mode can be driven by the driving mode such as the active matrix mode and the passive matrix mode. Such a device can also be applied to any of the reflective type, the transmissive type and the transflective type. A device having a polymer dispersed mode can also be prepared by increasing the amount of adding the polymerizable compound.

In a polymer sustained (PS) mode liquid crystal display device, the liquid crystal composition containing the polymer is used. First, a composition to which a small amount of a polymerizable compound is added is injected into the device. Next, the composition is irradiated with ultraviolet light. The polymerizable compound is polymerized to form a network structure of the polymer in the composition. In the composition, alignment of liquid crystal molecules can be controlled by the polymer, and therefore the response time in the device is shortened and also the image persistence is improved. The polar compound of the invention promotes the alignment of liquid crystal molecules. More specifically, the polar compound of the invention can be used in place of the alignment treatment. One example of a method for producing such a device is as described below. A device having a pair of transparent substrates subjected to neither alignment treatment nor an alignment film for aligning a liquid crystal medium is arranged. At least one of the substrates has an electrode layer. A liquid crystal composition is prepared by mixing liquid crystal compounds. A polymerizable compound and a polar compound are added to the composition. An additive may be further added thereto, when necessary. The composition is injected into the device. The device is irradiated with light. Ultraviolet light is preferred. The polymerizable compound is polymerized by irradiation with light. The composition containing the polymer is formed by the polymerization, and the polymer sustained alignment mode device having is prepared.

In the procedure, the polar compound is locally distributed on the substrate because the polar group interacts with the substrate surface. The polar compound aligns the liquid crystal molecules. The polymerizable compound is also aligned according to the alignment. The polymerizable compound is polymerized by ultraviolet light in the above state, and therefore the polymer in which the alignment is maintained is formed. The alignment of liquid crystal molecules is additionally stabilized by an effect of the polymer, and therefore the response time of the device is shortened. The image persistence is caused by poor operation of the liquid crystal molecules, and therefore the persistence is also simultaneously improved by the effect of the polymer. In particular, when the polar compound of the invention has the polymerizable group, the polar compound aligns the liquid crystal molecules, and simultaneously is copolymerized with any other polymerizable compound. Thus, the polar compound is no longer leaked into the liquid crystal composition, and therefore the liquid crystal display device having the large voltage holding ratio can be obtained.

6.1 Substrate Used in Liquid Crystal Display Device

As the substrate used in the liquid crystal display device, glass, ITO or any other transparent substrate can be used, and an insulating film (for example, polyimide) or the like may be formed thereon. The transparent electrode is required to be formed on at least one of the pair of substrates used. In order for the polar compound of the invention to sufficiently produce the effect, the substrate preferably has a predetermined uneven structure, and the liquid crystal compound aligns along a pattern of the structure. A pattern interval of the uneven structure is preferably 1 to 20 micrometers, further preferably 1 to 10 micrometers, and particularly preferably about 5 micrometers.

The uneven structure on the substrate may be formed by the electrode, and the electrode used is preferably a transparent electrode of ITO or the like.

With regard to a principle according to which the liquid crystal compound is aligned by the polar compound of the invention, although the invention is not always particularly limited thereto, the principle is considered in such a manner that the polar compound is locally distributed on the substrate surface by the polar group of the polar compound upon injecting the liquid crystal composition into the liquid crystal cell to operate surface tension on a side of the substrate to be acted on the liquid crystal compound.

6.2 Ratio of Total Positive-Phase Negative-Phase CV Product to Surface Free Energy In the polar compound of the invention, the total positive-phase negative-phase CV product in the liquid crystal composition is defined, and further in a relationship with the substrate composing the cell upon injecting the liquid crystal composition into the liquid crystal cell, a ratio (total positive-phase negative-phase CV product/surface free energy) of the total positive-phase negative-phase CV product of the polar compound to the surface free energy of the substrate is preferably 0.025 to 1. The ratio is further preferably 0.03 to 0.80, and still further preferably 0.05 to 0.5.

6.3 Alignment State of Liquid Crystal Medium in Liquid Crystal Display Device

The liquid crystal medium in the liquid crystal display device according to the invention homogeneously aligns relative thereto. An expression "state in which the liquid crystal medium homogeneously aligns relative thereto" means a state in which the liquid crystal medium aligns in parallel to the substrate surface, and also the liquid crystal medium aligns inside the plane in parallel to the substrate surface. Although a direction of in-plane alignment is not always limited to the following, the liquid crystal medium aligns along the uneven structure formed by the electrode or the like.

EXAMPLES

The invention will be described in greater detail by way of Examples. However, the invention is not limited by the Examples. A prepared compound was identified by a method such as an NMR analysis. Values of physical properties of a compound and a composition were determined according to methods described below.

NMR Analysis

As a measuring apparatus, DRX-500 (made by Bruker BioSpin Corporation) was used. In $^1$H-NMR measurement, a sample was dissolved in a deuterated solvent such as $CDCl_3$, and measurement was carried out under conditions of room temperature, 500 MHz and 16 times of accumulation. Tetramethylsilane was used as an internal standard. In $^{19}$F-NMR measurement, $CFCl_3$ was used as an internal standard, and measurement was carried out under conditions of 24 times of accumulation. In explaining nuclear magnetic resonance spectra obtained, s, d, t, q, quin, sex and m stand for a singlet, a doublet, a triplet, a quartet, a quintet, a sextet and a multiplet, and br being broad, respectively.

Sample for Measurement

Upon measuring a phase structure and transition temperature, a compound itself was used as a sample. Upon measuring physical properties such as maximum temperature of a nematic phase, viscosity, optical anisotropy and dielectric anisotropy, a composition prepared by mixing the compound with a base liquid crystal was used as the sample.

Measuring Method

Physical properties were measured according to methods described below. Most of the measuring methods are applied as described in the Standard of Japan Electronics and Information Technology Industries Association (hereinafter abbreviated as JEITA) (JEITA ED-2521B) discussed and established by JEITA or modified thereon. No TFT was attached to a TN device used for measurement.

(1) Phase Structure

A sample was placed on a hot plate in a melting point apparatus (FP-52 Hot Stage made by Mettler-Toledo International Inc.) equipped with a polarizing microscope, and a state of a phase and a change thereof were observed with the polarizing microscope while the sample was heated at a rate of 3° C. per minute, and a kind of the phase was specified.

(2) Transition Temperature (° C.)

A sample was heated and then cooled at a rate of 3° C. per minute by using a differential scanning calorimeter, DSC-7 System or Diamond DSC System, made by PerkinElmer, Inc., and a starting point of an endothermic peak or an exothermic peak caused by a phase change of the sample was determined by extrapolation, and thus a transition temperature was determined. Temperature at which a compound undergoes transition from a solid to a liquid crystal phase such as a smectic phase and the nematic phase may be occasionally abbreviated as "minimum temperature of the liquid crystal phase." Temperature at which the compound undergoes transition from the liquid crystal phase to a liquid may be occasionally abbreviated as "clearing point."

A crystal was expressed as C. When kinds of the crystals were distinguishable, each of the crystals was expressed as $C_1$ or $C_2$. The smectic phase or the nematic phase was expressed as S or N. When smectic A phase, smectic B phase, smectic C phase or smectic F phase was distinguishable among the smectic phases, the phases were expressed as $S_A$, $S_B$, $S_C$ or $S_F$, respectively. The liquid (isotropic) was expressed as I. A transition temperature was expressed as "C 50.0 N 100.0 I," for example. The expression indicates that a transition temperature from the crystals to the nematic phase is 50.0° C., and a transition temperature from the nematic phase to the liquid is 100.0° C.

(3) Compatibility at Low Temperature

Samples in which the base liquid crystal and the compound were mixed to be 20% by weight, 15% by weight, 10% by weight, 5% by weight, 3% by weight and 1% by weight in a proportions of the compound were prepared and put in glass vials. After the glass vials were kept in freezers at −10° C. or −20° C. for a predetermined period of time, whether or not the crystals (or the smectic phase) precipitated was observed.

(4) Maximum Temperature of Nematic Phase ($T_{NI}$ or NI; ° C.)

A sample was placed on a hot plate in a melting point apparatus equipped with a polarizing microscope, and heated at a rate of 1° C. per minute. Temperature when part of the sample began to change from the nematic phase to an isotropic liquid was measured. A maximum temperature of the nematic phase may be occasionally abbreviated as "maximum temperature." When the sample was a mixture of a compound and the base liquid crystal, the maximum temperature was expressed in terms of a symbol $T_{NI}$. When the sample was a mixture of a compound and component B or the like, the maximum temperature was expressed in terms of a symbol NI.

(5) Minimum Temperature of Nematic Phase ($T_C$; ° C.)

Samples each having the nematic phase were kept in freezers at temperatures of 0° C., −10° C., −20° C., −30° C. and −40° C. for 10 days, and then liquid crystal phases were observed. For example, when the sample maintained the nematic phase at −20° C. and changed to crystals or the smectic phase at −30° C., $T_C$ was expressed as $T_C \leq -20°$ C. A minimum temperature of the nematic phase may be occasionally abbreviated as "minimum temperature."

(6) Viscosity (Bulk Viscosity; q; Measured at 20° C.; mPa·s)

Measurement was carried out by using a cone-plate (E type) rotational viscometer.

(7) Viscosity (Rotational Viscosity; γ1; Measured at 25° C.; mPa·s)

Measurement was carried out according to the method described in M. Imai et al., Molecular Crystals and Liquid Crystals, Vol. 259, p. 37 (1995). A sample was put in a TN device in which a twist angle was 0 degrees and a distance (cell gap) between two glass substrates was 5 micrometers. Voltage was applied stepwise to the device in the range of 16 V to 19.5 V at an increment of 0.5 V. After a period of 0.2 second with no voltage application, voltage was repeatedly applied under conditions of only one rectangular wave (rectangular pulse; 0.2 second) and no voltage application (2 seconds). A peak current and a peak time of transient current generated by the applied voltage were measured. A value of rotational viscosity was obtained from the measured values and calculation equation (8) described on page 40 of the paper presented by M. Imai et al. A value of dielectric anisotropy required for the calculation was determined by using the device by which the rotational viscosity was measured according to the method described below.

(8) Optical Anisotropy (Refractive Index Anisotropy; Measured at 25° C.; Δn)

Measurement was carried out by an Abbe refractometer with a polarizing plate mounted on an ocular, using light at a wavelength of 589 nanometers. A surface of a main prism was rubbed in one direction, and then a sample was added dropwise onto the main prism. A refractive index (n∥) was measured when a direction of polarized light was parallel to a direction of rubbing. A refractive index (n⊥) was measured when the direction of polarized light was perpendicular to the direction of rubbing. A value of optical anisotropy (Δn) was calculated from an equation: Δn=n∥−n⊥.

(9) Dielectric Anisotropy (Δε; Measured at 25° C.)

A sample was put in a TN device in which a distance (cell gap) between two glass substrates was 9 micrometers and a twist angle was 80 degrees. Sine waves (10 V, 1 kHz) were applied to the device, and after 2 seconds, a dielectric constant (ε∥) of liquid crystal molecules in a major axis direction was measured. Sine waves (0.5 V, 1 kHz) were applied to the device, and after 2 seconds, a dielectric constant (ε⊥) of liquid crystal molecules in a minor axis direction was measured. A value of dielectric anisotropy was calculated from an equation: Δε=ε∥−ε⊥.

(10) Elastic Constant (K; Measured at 25° C.; pN)

For measurement, HP4284A LCR Meter made by Yokogawa-Hewlett-Packard Co. was used. A sample was put in a horizontal alignment device in which a distance (cell gap) between two glass substrates was 20 micrometers. An electric charge of 0 V to 20 V was applied to the device, and electrostatic capacity (C) and applied voltage (V) were measured. The measured values were fitted to equation (2.98) and equation (2.101) on page 75 of "Liquid Crystal Device Handbook" (Ekisho Debaisu Handobukku in Japanese; Nikkan Kogyo Shimbun, Ltd.) and values of K11 and K33 were obtained from equation (2.99). Next, K22 was calculated by using the previously determined values of K11 and K33 in equation (3.18) on page 171. Elastic constant K was expressed in terms of a mean value of the thus determined K11, K22 and K33.

(11) Threshold Voltage (Vth; Measured at 25° C.; V)

For measurement, an LCD5100 luminance meter made by Otsuka Electronics Co., Ltd. was used. A light source was a halogen lamp. A sample was put in a normally white mode TN device in which a distance (cell gap) between two glass substrates was 0.45/Δn (μm) and a twist angle was 80 degrees. A voltage (32 Hz, rectangular waves) to be applied to the device was stepwise increased from 0 V to 10 V at an increment of 0.02 V. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. A threshold voltage is expressed in terms of a voltage at 90% transmittance.

(12) Voltage Holding Ratio (VHR-1; Measured at 25° C.; %)

A TN device used for measurement had a polyimide-alignment film, and a distance (cell gap) between two glass substrates was 5 micrometers. A sample was put in the device, and then the device was sealed with an ultraviolet-curable adhesive. A pulse voltage (60 microseconds at 5 V) was applied to the TN device, and the device was charged. A decaying voltage was measured for 16.7 milliseconds with a high-speed voltmeter, and area A between a voltage curve and a horizontal axis in a unit cycle was determined. Area B is an area without decay. A voltage holding ratio is a percentage of area A to area B.

(13) Voltage Holding Ratio (VHR-2; Measured at 80° C.; %)

A TN device used for measurement had a polyimide-alignment film, and a distance (cell gap) between two glass substrates was 5 micrometers. A sample was put in the device, and then the device was sealed with an ultraviolet-curable adhesive. A pulse voltage (60 microseconds at 5 V) was applied to the TN device, and the device was charged. A decaying voltage was measured for 16.7 milliseconds with a high-speed voltmeter, and area A between a voltage curve and a horizontal axis in a unit cycle was determined. Area B is an area without decay. A voltage holding ratio is a percentage of area A to area B.

Raw material: Solmix A-11 (registered trade name) is a mixture of ethanol (85.5% by weight), methanol (13.4% by weight) and isopropanol (1.1% by weight), and was purchased from Japan Alcohol Trading Co., Ltd.

Synthesis Example of Polar Compound (2-1-1)

Formula 58

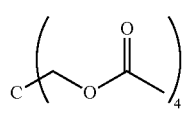

(2-1-1)

Polar compound (2-1-1) was obtained from Tokyo Chemical Industry Co., Ltd.

Synthesis Example of Polar Compound (2-2-1)

Formula 59

(2-2-1)

Polar compound (2-2-1) was obtained from Tokyo Chemical Industry Co., Ltd.

Synthesis Example of Polar Compound (3-1-1)

Formula 60

(3-1-1)

Polar compound (3-1-1) was obtained from Tokyo Chemical Industry Co., Ltd.

Synthesis Example of Polar Compound (3-1-2)

Formula 61

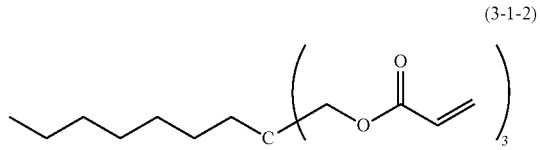

(3-1-2)

First Step

Paraformaldehyde (12 g) and 2-methyl 2-methoxypropane (t-BuOMe, 31 g) were put in a reaction vessel, and while maintaining the resulting mixture inside a system at about 40° C., an aqueous solution of water (6 g), NaOH (8 g) and nonanal (10.5 g) was added dropwise thereto. Then, an aqueous solution of water (2 g) and NaOH (2 g) was added thereto, and the resulting mixture was refluxed for 1 hour. The resulting mixture inside the system was neutralized with formic acid, and the resulting mixture was poured into water and subjected to extraction with toluene. The resulting solution was concentrated under reduced pressure, and the residue was purified by silica gel column (solvent: ethyl acetate) to obtain intermediate compound (T-1) (10 g).

Second Step

Intermediate compound (T-1) (3.5 g), triethylamine (6.1 g) and dichloromethane (30 mL) were put in a reaction vessel, and the resulting mixture was cooled down to 0° C. Thereto, a dichloromethane solution (10 mL) of acrylic acid chloride (6.2 g) was added dropwise, and the resulting mixture was stirred for 1 hour while raising temperature to room temperature, and then the resulting reaction mixture was poured into water, and an aqueous layer was subjected to extraction with dichloromethane. The resulting solution was concentrated under reduced pressure, and the residue was purified by silica gel column (solvent: toluene/ethyl acetate=20/1 in a volume ratio) to obtain oily polar compound (3-1-2) (5 g).

Formula 62

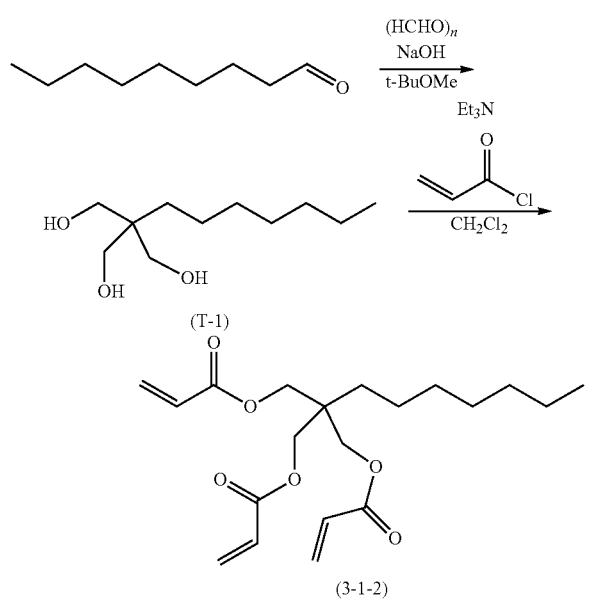

(3-1-2)

An NMR analysis value of the resulting polar compound (3-1-2) was as described below.

$^1$H-NMR: chemical shift δ (ppm; CDCl$_3$): 6.40 (d, 3H), 6.11 (dd, 3H), 5.86 (d, 3H), 4.67 (s, 6H), 1.52-1.19 (m, 12H) 0.87 (t, 3H).

Synthesis Example of Polar Compound (4-11-1)

Formula 63

(4-11-1)

Compound (A) (3.00 g), diethylamine (1.30 g) and cyclohexane (100 mL) were put in a reaction vessel, and the resulting mixture was stirred at 75° C. for 12 hours. An insoluble matter was filtered off, and then the resulting reaction mixture was poured into water, and an aqueous layer was subjected to extraction with ethyl acetate. A combined organic layer was washed with water and dried over anhydrous magnesium sulfate. The resulting solution was concentrated under reduced pressure, and the residue was purified by silica gel column (solvent: toluene/ethyl acetate=1/1 in a volume ratio) to obtain polar compound (4-11-1) (0.52 g, yield: 15%).

Formula 64

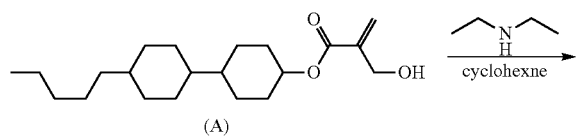

(A)

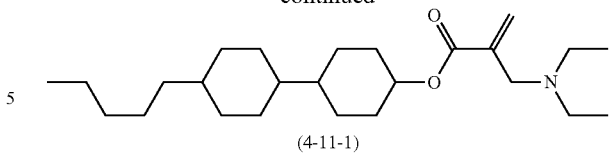

(4-11-1)

An NMR analysis value of the resulting polar compound (4-11-1) was as described below.

$^1$H-NMR: chemical shift δ (ppm; CDCl$_3$): 6.18 (s, 1H), 5.74 (s, 1H), 4.74-4.67 (m, 1H), 3.23 (s, 2H), 2.50 (q, J=7.1 Hz, 4H), 2.03-2.01 (m, 2H), 1.78-1.68 (m, 6H), 1.37-0.80 (m, 28H).

Physical properties of polar compound (4-11-1) were as described below.

Transition temperature: C 14.1 S$_A$ 58.9 I.

In addition, compound (A) was prepared as described below.

Formula 65

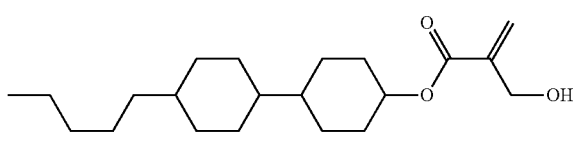

(A)

First Step

Compound (T-1) (25.0 g), acrylic acid (7.14 g), N,N-dimethyl-4-aminopyridine (DMAP, 1.21 g) and dichloromethane (300 mL) were put in a reaction vessel, and the resulting mixture was cooled down to 0° C. Thereto, a dichloromethane (125 mL) solution of N, N'-dicyclohexylcarbodiimide (DCC, 24.5 g) was slowly added dropwise, and the resulting mixture was stirred for 12 hours while returning to room temperature. An insoluble matter was filtered off, and then the resulting reaction mixture was poured into water, and an aqueous layer was subjected to extraction with dichloromethane. A combined organic layer was washed with water and dried over anhydrous magnesium sulfate. The resulting solution was concentrated under reduced pressure, and the residue was purified by silica gel column (solvent: heptane/toluene=2/1 in a volume ratio). The residue was further purified by recrystallization from Solmix (registered trade name) A-11 to obtain intermediate compound (T-2) (11.6 g, yield: 38%).

Second Step

Paraformaldehyde (2.75 g), 1,4-diazabicyclo[2.2.2]octane (DABCO, 4.62 g) and water (40 mL) were put in a reaction vessel, and the resulting mixture was stirred at room temperature for 15 minutes. Thereto, a THF (90 mL) solution of intermediate compound (T-2) (6.31 g) was added dropwise, and the resulting mixture was stirred at room temperature for 72 hours. The resulting reaction mixture was poured into water, and an aqueous layer was subjected to extraction with ethyl acetate. A combined organic layer was washed with water and dried over anhydrous magnesium sulfate. The resulting solution was concentrated under reduced pressure, and the residue was purified by silica gel column (solvent: toluene/ethyl acetate=5/1 in a volume ratio). The residue was further purified by recrystallization from a mixed solvent of heptane and toluene (1:1 in a volume ratio) to obtain compound (A) (1.97 g, yield: 29%).

Formula 66

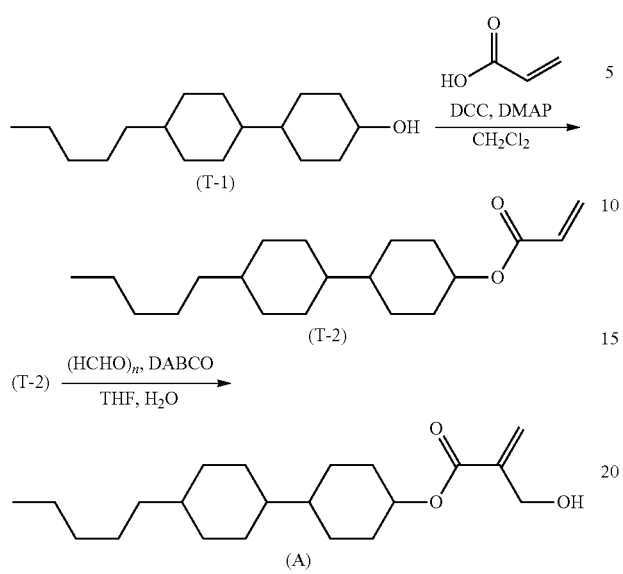

An NMR analysis value of the resulting compound (A) was as described below.

$^1$H-NMR: chemical shift δ (ppm; CDCl$_3$): 6.23 (s, 1H), 5.79 (d, J=1.2 Hz, 1H), 4.79-4.70 (m, 1H), 4.32 (d, J=6.7 Hz, 2H), 2.29 (t, J=6.7 Hz, 1H), 2.07-2.00 (m, 2H), 1.83-1.67 (m, 6H), 1.42-1.18 (m, 8H), 1.18-0.91 (m, 9H), 0.91-0.79 (m, 5H).

Physical properties of compound (A) were as described below.

Transition temperature: C 40.8 S$_A$ 109 I.

Synthesis Example of Polar Compound (4-21-1)

Formula 67

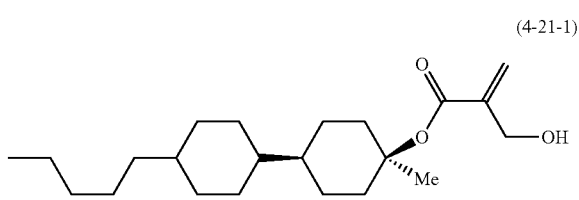

First Step

Compound (T-64) (10.0 g) and THF (200 mL) were put in a reaction vessel, and the resulting mixture was cooled down to 0° C. Methylmagnesium bromide (MeMgBr, 1.00 M, THF solution, 48 mL) was slowly added thereto, and the resulting mixture was stirred for 6 hours while returning to room temperature. An insoluble matter was filtered off, and then the resulting reaction mixture was poured into water, and an aqueous layer was subjected to extraction with ethyl acetate. A combined organic layer was washed with water and dried over anhydrous magnesium sulfate. The resulting solution was concentrated under reduced pressure, and the residue was purified by silica gel column (solvent: toluene/ethyl acetate=9/1 in a volume ratio) to obtain intermediate compound (T-65) (4.58 g, yield: 43%).

Second Step

Intermediate compound (T-65) (4.58 g), triethylamine (2.87 mL) and THF (200 mL) were put in a reaction vessel, and the resulting mixture was cooled down to 0° C. Acrylic acid chloride (1.68 mL) was slowly added thereto, and the resulting mixture was stirred for 5 hours while returning to room temperature. An insoluble matter was filtered off, and then the resulting reaction mixture was poured into water, and an aqueous layer was subjected to extraction with toluene. A combined organic layer was washed with water and dried over anhydrous magnesium sulfate. The resulting solution was concentrated under reduced pressure, and the residue was purified by silica gel column (solvent: toluene/heptane=3/2 in a volume ratio) to obtain intermediate compound (T-66) (3.20 g, yield: 58%).

Third Step

Operation was made by using intermediate compound (T-66) (3.20 g) as a raw material in a manner similar to the technique in the second step in the method for preparing compound (A) to obtain polar compound (4-21-1) (1.12 g, yield: 32%).

Formula 68

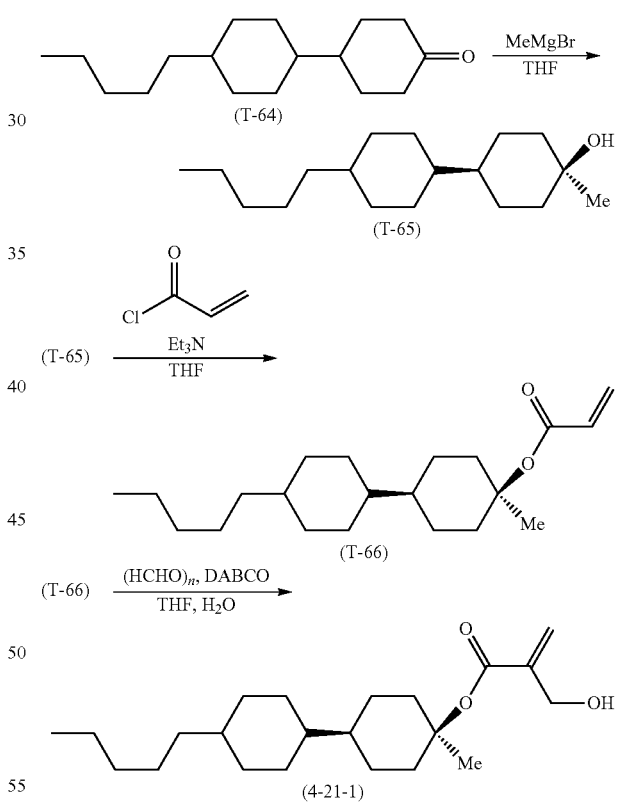

An NMR analysis value of the resulting polar compound (4-21-1) was as described below.

$^1$H-NMR: chemical shift δ (ppm; CDCl$_3$): 6.15 (s, 1H), 5.73 (d, J=1.2 Hz, 1H), 4.28 (d, J=6.6 Hz, 2H), 2.34-2.32 (m, 1H), 2.13-2.11 (m, 2H), 1.76-1.67 (m, 8H), 1.54 (s, 3H), 1.32-1.03 (m, 13H), 0.97-0.80 (m, 7H).

Physical properties of polar compound (4-21-1) were as described below.

Transition temperature: C 66.5 S$_A$ 81.1 I.

Synthesis Example of Polar Compound (4-22-1)

Formula 69

(4-22-1)

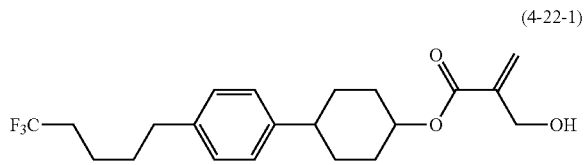

First Step
Compound (T-49) (15.0 g) and triphenyl phosphine (PPh₃, 24.8 g) were put in a reaction vessel, and the resulting mixture was stirred at 100° C. for 6 hours. The resulting material was filtrated and washed with heptane cooled with ice to obtain intermediate compound (T-50) (16.4 g, yield: 52%).

Second Step
Compound (T-51) (10.0 g) and THF (200 mL) were put in a reaction vessel, and the resulting mixture was cooled down to −70° C. Then, n-butyllithium (1.63 M, hexane solution, 25 mL) was slowly added thereto, and the resulting mixture was stirred for 1 hour. DMF (4.0 mL) was slowly added thereto, and the resulting mixture was stirred for 12 hours while returning to room temperature. An insoluble matter was filtered off, and then the resulting reaction mixture was poured into water, and an aqueous layer was subjected to extraction with toluene. A combined organic layer was washed with water and dried over anhydrous magnesium sulfate. The resulting solution was concentrated under reduced pressure, and the residue was purified by silica gel column (solvent: toluene/ethyl acetate=9/1 in a volume ratio) to obtain intermediate compound (T-52) (6.37 g, yield: 77%).

Third Step
Intermediate compound (T-50) (14.3 g) and THF (200 mL) were put in a reaction vessel, and the resulting mixture was cooled down to −30° C. Thereto, potassium t-butoxide (3.21 g) was slowly added, and the resulting mixture was stirred at −30° C. for 1 hour. A THF (100 mL) solution of intermediate compound (T-52) (6.37 g) was slowly added thereto, and the resulting mixture was stirred for 4 hours while returning to room temperature. An insoluble matter was filtered off, and then the resulting reaction mixture was poured into water, and an aqueous layer was subjected to extraction with toluene. A combined organic layer was washed with water and dried over anhydrous magnesium sulfate. The resulting solution was concentrated under reduced pressure, and the residue was purified by silica gel column (solvent: toluene) to obtain intermediate compound (T-53) (7.50 g, yield: 85%).

Fourth Step
Intermediate compound (T-53) (7.50 g), Pd/C (0.11 g), IPA (200 mL) and toluene (200 mL) were put in a reaction vessel, and the resulting mixture was stirred at room temperature for 12 hours under a hydrogen atmosphere. An insoluble matter was filtered off, and then the resulting reaction mixture was poured into water, and an aqueous layer was subjected to extraction with toluene. A combined organic layer was washed with water and dried over anhydrous magnesium sulfate. The resulting solution was concentrated under reduced pressure, and the residue was purified by silica gel column (solvent: toluene) to obtain intermediate compound (T-54) (7.21 g, yield: 95%).

Fifth Step
Intermediate compound (T-54) (7.21 g), formic acid (9.70 g) and toluene (200 mL) were put in a reaction vessel, and the resulting mixture was stirred at 100° C. for 4 hours. An insoluble matter was filtered off, and then the resulting material was neutralized with a sodium hydrogencarbonate aqueous solution, and an aqueous layer was subjected to extraction with toluene. A combined organic layer was washed with water and dried over anhydrous magnesium sulfate. The resulting solution was concentrated under reduced pressure, and the residue was purified by silica gel column (solvent: toluene) to obtain intermediate compound (T-55) (5.65 g, yield: 90%).

Sixth Step
Lithium aluminum hydride (LAH, 0.43 g) and THF (100 mL) were put in a reaction vessel, and the resulting mixture was cooled with ice. A THF (100 mL) solution of intermediate compound (T-55) (5.65 g) was slowly added thereto, and the resulting mixture was stirred for 2 hours while returning to room temperature. The resulting reaction mixture was poured into water, and an aqueous layer was subjected to extraction with ethyl acetate. A combined organic layer was washed with brine and dried over anhydrous magnesium sulfate. The resulting solution was concentrated under reduced pressure, and the residue was purified by silica gel column (solvent: toluene/ethyl acetate=9/1 in a volume ratio). The residue was further purified by recrystallization from heptane to obtain intermediate compound (T-56) (4.83 g, yield: 85%).

Seventh Step
Intermediate compound (T-56) (4.83 g), compound (T-18), N,N-dimethyl-4-aminopyridine (DMAP) and dichloromethane were put in a reaction vessel, and the resulting mixture was cooled down to 0° C. Thereto, a dichloromethane solution of N,N'-dicyclohexylcarbodiimide (DCC) was slowly added dropwise, and the resulting mixture was stirred for 12 hours while returning to room temperature. An insoluble matter was filtered off, and then the resulting reaction mixture was poured into water, and an aqueous layer was subjected to extraction with dichloromethane. A combined organic layer was washed with water and dried over anhydrous magnesium sulfate. The resulting solution was concentrated under reduced pressure, and the residue was purified by silica gel column (solvent: heptane/toluene=1/1 in a volume ratio) to obtain intermediate compound (T-57) (8.41 g, yield: 84%). In addition, "OTBDPS" in a synthesis scheme is a t-butylphenylsilyloxy group.

Eighth Step
Intermediate compound (T-57) (8.41 g) and THF were put in a reaction vessel, and the resulting mixture was cooled down to 0° C. Thereto, tetrabutylammonium fluoride (TBAF, 1.00 M, THF solution) was slowly added, and the resulting mixture was stirred for 1 hour while returning to room temperature. The resulting reaction mixture was poured into water, and an aqueous layer was subjected to extraction with ethyl acetate. A combined organic layer was washed with brine and dried over anhydrous magnesium sulfate. The resulting solution was concentrated under reduced pressure, and the residue was purified by silica gel column (solvent: toluene/ethyl acetate=9/1 in a volume ratio). The residue was further purified by recrystallization from heptane to obtain polar compound (4-22-1) (3.22 g, yield: 62%).

Formula 70

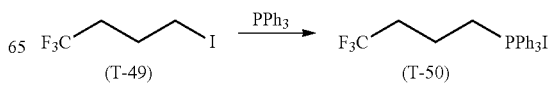

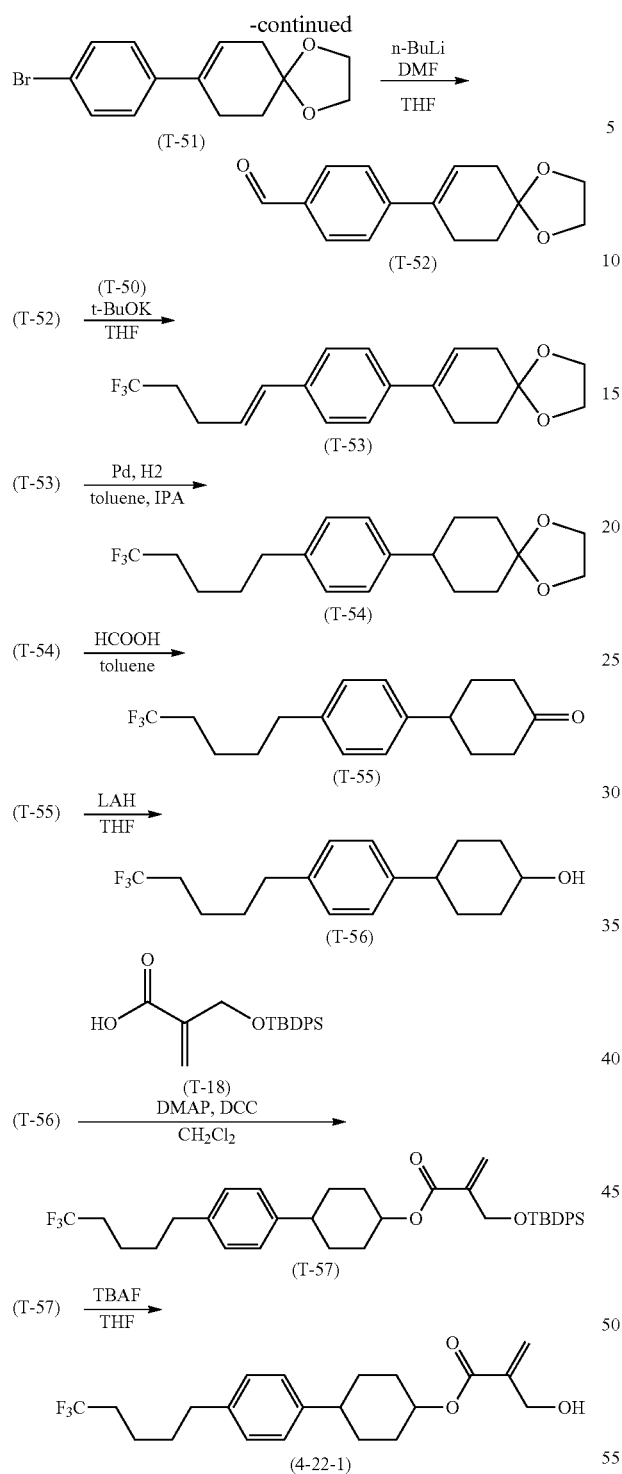

According to the synthesis methods described in Synthesis Examples described above, compounds (2-1-1) to (2-1-4), compounds (2-2-1) to (2-2-7) and compounds (3-1-1) to (3-1-11) described below can be prepared.

Formula 71

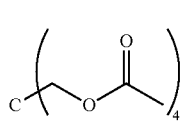 (2-1-1)

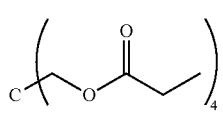 (2-1-2)

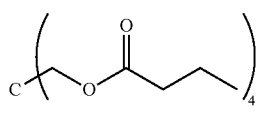 (2-1-3)

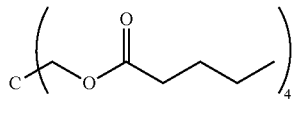 (2-1-4)

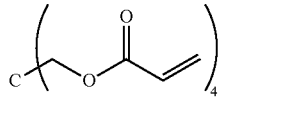 (2-2-1)

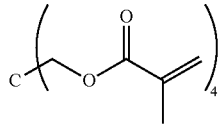 (2-2-2)

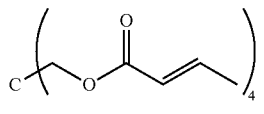 (2-2-3)

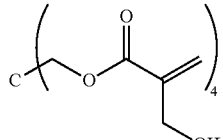 (2-2-4)

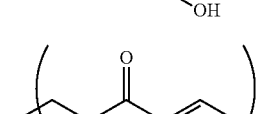 (2-2-5)

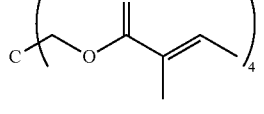 (2-2-6)

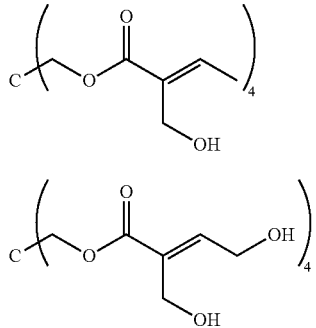 (2-2-7)

An NMR analysis value of the resulting polar compound (4-22-1) was as described below.

$^1$H-NMR: chemical shift δ (ppm; CDCl$_3$): 7.13 (d, J=8.2 Hz, 2H), 7.10 (d, J=8.2 Hz, 2H), 6.26 (s, 1H), 5.82 (d, J=1.1 Hz, 1H), 4.92-4.87 (m, 1H), 4.34 (d, J=6.7 Hz, 2H), 2.60 (t, J=7.3 Hz, 2H), 2.54-2.49 (m, 1H), 2.31 (t, J=6.5 Hz, 1H), 2.15-2.04 (m, 4H), 1.98-1.96 (m, 2H), 1.66-1.52 (m, 8H).

Physical properties of polar compound (4-22-1) were as described below.

Transition temperature: C 62.0 I.

(3-1-1) 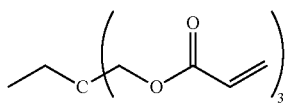

(3-1-2) 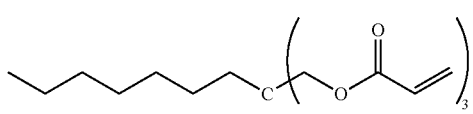

(3-1-3) 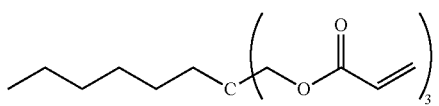

(3-1-4) 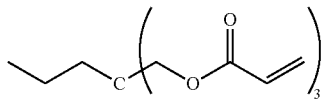

(3-1-5) 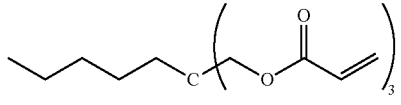

(3-1-6) 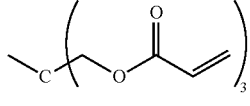

(3-1-7) 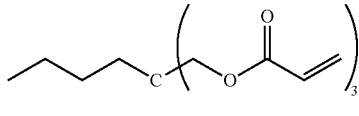

(3-1-8) 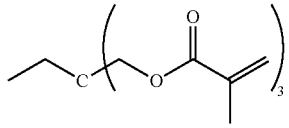

(3-1-9) 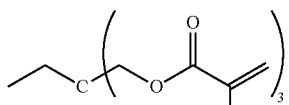

(3-1-10) 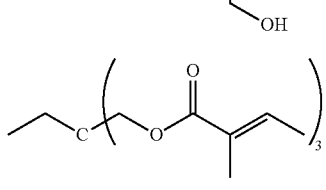

(3-1-11) 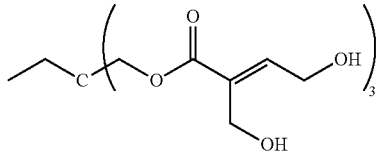

Positive-Phase Negative-Phase CV Product of Low Molecular Weight Polar Compound

The term "positive-phase negative-phase CV product" means the value expressed in terms of the numerical form as to what degree of the polar group and the nonpolar group exist in one molecule, in which the value increases in the compound having the chemical structure in which a strong polar group and a strong nonpolar group coexist, and the value decreases in the compound having the chemical structure in which the molecule as a whole is neutral.

The positive-phase negative-phase CV product is measured by developing the compound by normal-phase TLC and reversed-phase TLC, and expressed in terms of a product of reciprocal CV values (1/Rf) of each Rf value (development distance of sample/development distance of moving layer). The compound having a small Rf value upon measuring the compound by the normal-phase TLC has the polar group, and the compound having the small Rf value upon measuring the compound by the reversed-phase TLC has the nonpolar group. Two characteristics described above may be occasionally simultaneously satisfied in one compound, and neither may be occasionally satisfied. As a standard measuring method, the compound is developed with a mixed solvent (4:1 in a volume ratio) of toluene and ethyl acetate by using TLC (Silica gel 60 F254) made by Merck Ltd. in measuring the compound by the normal-phase TLC, and the compound is developed with methanol by using TLC (Silica gel 60 RP-18 F254s) made by Merck Ltd. in measuring the compound by the reversed-phase TLC.

Positive-phase negative-phase $CV$ product$=1/Rf(p) \times 1/Rf(n)$

Rf (p): Rf value in a positive phase

Rf(n): Rf value in a negative phase

In addition, in the case of the polar compound that is difficult to be developed with the mixed solvent of toluene and ethyl acetate or methanol, the Rf value can be determined even for the polar compound that is unable to be developed with the solvent described above by using a polar compound that can be developed according to the method described above and has polarity comparatively close thereto as a reference, and developing the polar compound simultaneously with the compound that is unable to be developed with the solvent described above, with any other solvent easily causing development, and by conversion from a ratio of the Rf values on the above occasion. For example, when a development width of the compound that is unable to be developed with the solvent described above is twice as large as the development width of the reference compound, a value twice the Rf value obtained by measuring the reference compound according to an inherent method is applied as the Rf value of the compound that is unable to be developed with the solvent described above.

TABLE 1

| Low molecular weight polar compound | Rf(p) | Rf(n) | 1/Rf(p) | 1/Rf(n) | Positive-phase negative-phase CV product |
|---|---|---|---|---|---|
| 2-1-1 | 0.26 | 0.85 | 3.83 | 1.18 | 4.52 |
| 2-2-1 | 0.56 | 0.90 | 1.78 | 1.11 | 1.98 |
| 3-1-1 | 0.68 | 0.82 | 1.48 | 1.22 | 1.81 |
| 3-1-2 | 0.73 | 0.70 | 1.37 | 1.43 | 1.96 |
| 4-11-1 | 0.81 | 0.40 | 1.24 | 2.52 | 3.12 |
| 4-21-1 | 0.60 | 0.46 | 1.68 | 2.18 | 3.66 |
| 4-22-1 | 0.46 | 0.71 | 2.17 | 1.41 | 3.06 |

Preparation of Liquid Crystal Composition (i)

Liquid crystal composition (i) was prepared by mixing compounds below at the following component proportion.

| 3HHV | 23% by weight |
|---|---|
| 1BHHV | 5% by weight |
| 1BB(F)B2V | 6% by weight |

-continued

| | |
|---|---|
| 3BB(F)B2V | 5% by weight |
| 3B3(F,F)XB(F,F)-F | 12% by weight |
| 3HHXB(F,F)-F | 24% by weight |
| 3HBB(F,F)-F | 11% by weight |
| 4BB(F)B(F,F)XB(F,F)-F | 7% by weight |
| 5BB(F)B(F,F)XB(F,F)-F | 7% by weight |

Formula 72

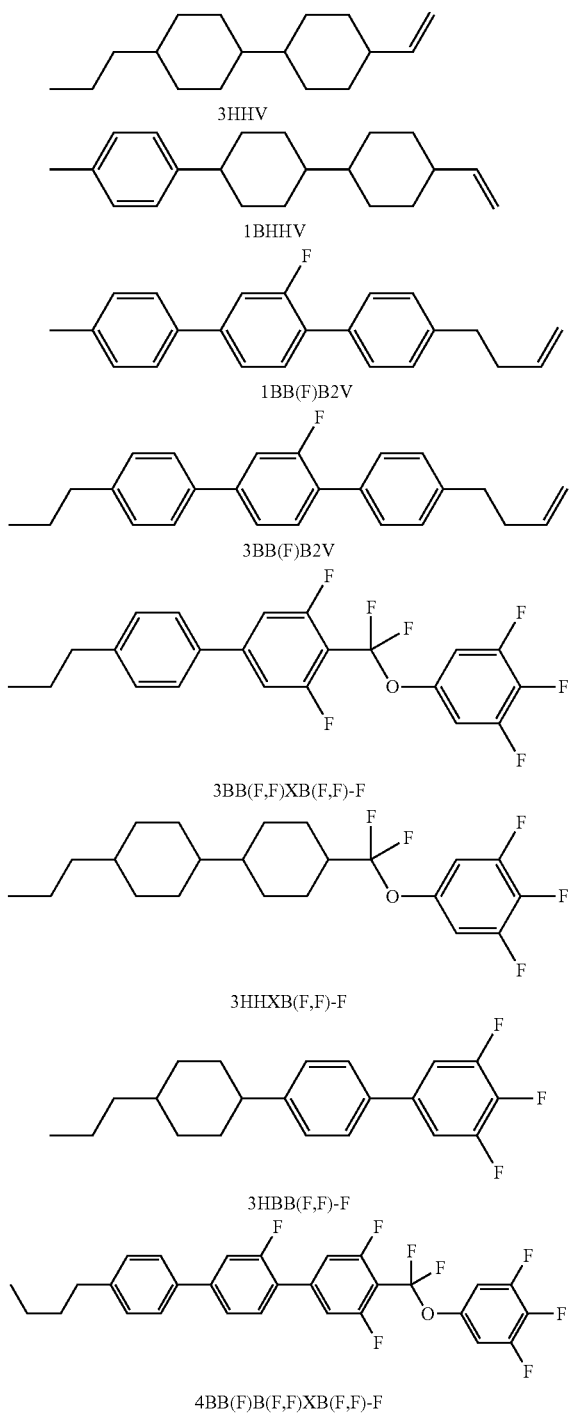

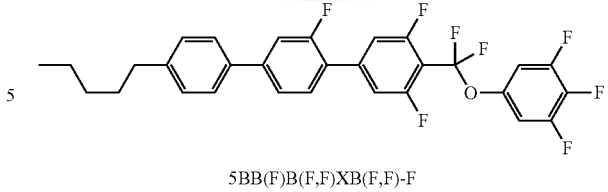

5BB(F)B(F,F)XB(F,F)-F

Example 1

Polar compound (3-1-2) was dissolved in liquid crystal composition (i) to be 3% by weight to obtain liquid crystal composition (1) of the invention.

NI=80.6° C.; η=18.0 mPa·s; Δn=0.123; Δε=10.3.

Liquid crystal composition (1) obtained was injected into a cell (upper surface: bare glass, lower surface: ITO patterning glass, cell gap: 5 μm, comb-shaped electrode having an interelectrode distance of 5 μm and an electrode width of 5 μm) by capillary force. In addition, a glass substrate of the cell is subjected to no alignment treatment. The cell was interposed between two polarizing plates formed in a crossed Nicols state, and the cell was observed visually and by a polarizing microscope while rotating the cell. As a result, the cell was confirmed in homogeneous alignment from repeating light and darkness at a cycle of 45 degrees.

A device was prepared by interposing the cell with the polarizing plates to be normally black, and voltage (60 Hz, rectangular wave) was applied thereto from 0 to 11 V. On the above occasion, the device was irradiated with light from a direction perpendicular to the device, and a change of an amount of light transmitted through the device was measured to obtain a voltage-transmittance curve (FIG. 1).

Examples 2 to 8

Liquid crystal compositions (2) to (8) of the invention were prepared according to Example 1 except that other polar compounds were used in place of polar compound (3-1-2). With regard to each liquid crystal composition, as a result of observing a cell by a polarizing microscope in the same manner as in Example 1, the cell was confirmed to be in homogeneous alignment. Moreover, voltage and transmittance were measured from a device prepared to confirm that a transmitted light amount was significantly changed.

Further, liquid crystal compositions (9) to (19) of the invention were prepared according to Example 1. With regard to each liquid crystal composition, as a result of observing a cell by a polarizing microscope in the same manner as in Example 1, the cell was confirmed to be in homogeneous alignment. Moreover, voltage and transmittance were measured from a device prepared to confirm that a transmitted light amount was significantly changed. Compounds in liquid crystal compositions (9) to (19) were represented by using symbols according to definitions in Table 2 described below. In Table 2, a configuration with regard to 1,4-cyclohexylene is trans. A proportion (percentage) of the liquid crystal compound is expressed in terms of weight percent (% by weight) based on the total weight of the liquid crystal composition. Values of physical properties of the composition are summarized in a last part. The physical properties were measured according to the methods described above, and measured values are directly described without extrapolation.

TABLE 2

Method for description of compounds using symbols
R—(A$_1$)—Z$_1$— . . . —Z$_n$—(A$_n$)—R'

| | Symbol |
|---|---|
| 1) Left-terminal group R— | |
| C$_n$H$_{2n+1}$— | n- |
| C$_n$H$_{2n+1}$O— | nO— |
| C$_m$H$_{2m+1}$OC$_n$H$_{2n}$— | mOn— |
| CH$_2$=CH— | V— |
| C$_n$H$_{2n+1}$—CH=CH— | nV— |
| CH$_2$=CH—C$_n$H$_{2n}$— | Vn— |
| C$_m$H$_{2m+1}$—CH=CH—C$_n$H$_{2n}$— | mVn— |
| CF$_2$=CH— | VFF— |
| CF$_2$=CH—C$_n$H$_{2n}$— | VFFn— |
| 2) Right-terminal group —R' | |
| —C$_n$H$_{2n+1}$ | -n |
| —OC$_n$H$_{2n+1}$ | —On |
| —COOCH$_3$ | —EMe |
| —CH=CH$_2$ | —V |
| —CH=CH—C$_n$H$_{2n+1}$ | —Vn |
| —C$_n$H$_{2n}$—CH=CH$_2$ | —nV |
| —C$_m$H$_{2m}$—CH=CH—C$_n$H$_{2n+1}$ | —mVn |
| —CH=CF$_2$ | —VFF |
| —F | —F |
| —Cl | —CL |
| —OCF$_3$ | —OCF3 |
| —OCF$_2$H | —OCF2H |
| —CF$_3$ | —CF3 |
| —OCH=CH—CF$_3$ | —OVCF3 |
| —C≡N— | —C |
| 3) Bonding group —Z$_n$— | |
| —C$_n$H$_{2n}$— | n |
| —COO— | E |
| —CH=CH— | V |
| —CH$_2$O— | 1O |
| —OCH$_2$— | O1 |
| —CF$_2$O— | X |
| —C≡C— | T |
| 4) Ring structure —A$_n$— | |
|  | H |
|  | B |
| 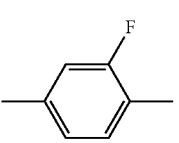 | B(F) |
| 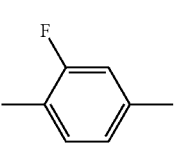 | B(2F) |
| 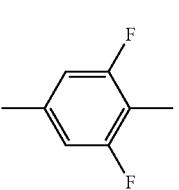 | B(F, F) |

TABLE 2-continued
Method for description of compounds using symbols
R—(A$_1$)—Z$_1$— ... —Z$_n$—(A$_n$)—R'
| | Symbol |
|---|---|
| 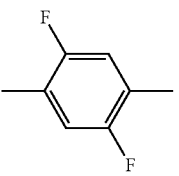 | B(2F, 5F) |
| 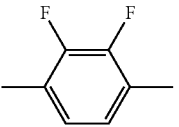 | B(2F, 3F) |
| 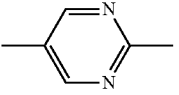 | Py |
| 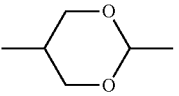 | G |
| 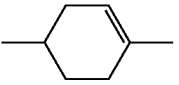 | ch |
5) Examples of description
Example 1 3-HB-CL
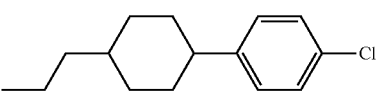 [SMILES: CCCC1CCC(c2ccc(Cl)cc2)CC1]
Example 2 5-HHBB(F, F)-F
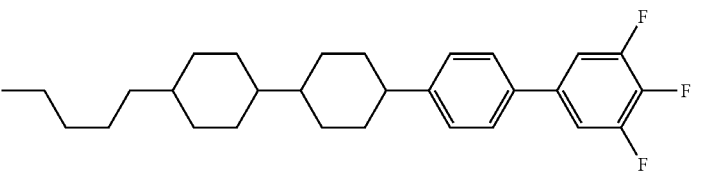 [SMILES: CCCCCC1CCC(C2CCC(c3ccc(-c4cc(F)c(F)c(F)c4)cc3)CC2)CC1]
Example 3 3-HB-O2
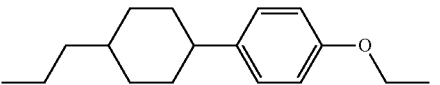 [SMILES: CCCC1CCC(c2ccc(OCC)cc2)CC1]
Example 4 3-HBB(F, F)-F
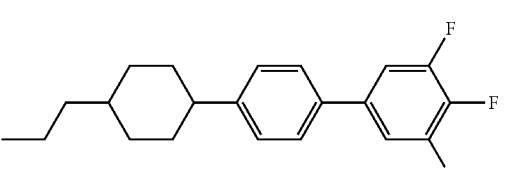

Liquid Crystal Composition 9

| | |
|---|---|
| 2-HB-C | 7% |
| 3-HB-C | 5% |
| 3-HB-O2 | 12% |
| 2-BTB-1 | 6% |
| 3-HHB-F | 5% |
| 3-HHB-1 | 7% |
| 3-HHB-O1 | 7% |
| 3-HHB-3 | 13% |
| 3-HHEB-F | 5% |
| 5-HHEB-F | 5% |
| 2-HHB(F)-F | 7% |
| 3-HHB(F)-F | 7% |
| 5-HHB(F)-F | 7% |
| 3-HHB(F,F)-F | 7% |

Compound (3-1-2) below was added to the composition described above at a proportion of 3% by weight.

Formula 73

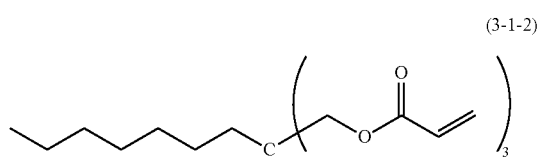

(3-1-2)

NI=105.7° C.; η=19.4 mPa·s; Δn=0.104; Δε=4.4.

Liquid Crystal Composition 10

| | |
|---|---|
| 3-HB-CL | 15% |
| 3-HB-O2 | 12% |
| 3-HHB(F,F)-F | 6% |
| 3-HBB(F,F)-F | 30% |
| 5-HBB(F,F)-F | 25% |
| 5-HBB(F)B-2 | 6% |
| 5-HBB(F)B-3 | 6% |

Compound (2-1-1) below was added to the composition described above at a proportion of 2% by weight.

Formula 74

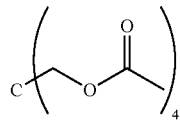

(2-1-1)

Compound (RM-1) below was further added to the composition at a proportion of 0.3% by weight.

Formula 75

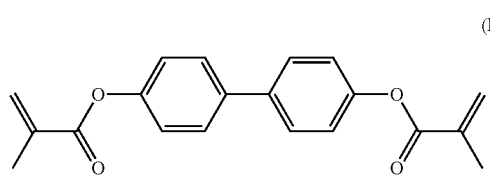

(RM-1)

NI=70.5° C.; η=22.3 mPa·s; Δn=0.125; Δε=6.1.

Liquid Crystal Composition 11

| | |
|---|---|
| 7-HB(F,F)-F | 5% |
| 3-HB-O2 | 8% |
| 2-HHB(F)-F | 10% |
| 3-HHB(F)-F | 10% |
| 5-HHB(F)-F | 11% |
| 2-HBB(F)-F | 7% |
| 3-HBB(F)-F | 8% |
| 5-HBB(F)-F | 14% |
| 2-HBB-F | 4% |
| 3-HBB-F | 4% |
| 5-HBB-F | 3% |
| 3-HBB(F,F)-F | 8% |
| 5-HBB(F,F)-F | 8% |

Compound (2-2-1) below was added to the composition described above at a proportion of 2% by weight.

Formula 76

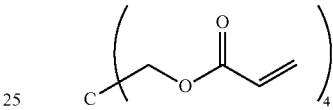

(2-2-1)

NI=81.9° C.; η=23.9 mPa·s; Δn=0.111; Δε=5.4.

Liquid Crystal Composition 12

| | |
|---|---|
| 5-HB-CL | 18% |
| 3-HHB-F | 10% |
| 3-HHB-CL | 5% |
| 4-HHB-CL | 4% |
| 3-HHB(F)-F | 12% |
| 4-HHB(F)-F | 9% |
| 5-HHB(F)-F | 9% |
| 7-HHB(F)-F | 8% |
| 5-HBB(F)-F | 4% |
| 101-HBBH-5 | 3% |
| 3-HHBB(F,F)-F | 4% |
| 4-HHBB(F,F)-F | 3% |
| 5-HHBB(F,F)-F | 4% |
| 3-HH2BB(F,F)-F | 4% |
| 4-HH2BB(F,F)-F | 3% |

Compound (3-1-1) below was added to the composition described above at a proportion of 3% by weight.

Formula 77

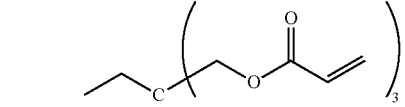

(3-1-1)

NI=125.2° C.; η=26.4 mPa·s; Δn=0.104; Δε=4.9.

Liquid Crystal Composition 13

| | |
|---|---|
| 3-HHB(F,F)-F | 8% |
| 3-H2HB(F,F)-F | 8% |
| 4-H2HB(F,F)-F | 8% |
| 5-H2HB(F,F)-F | 9% |
| 3-HBB(F,F)-F | 17% |
| 5-HBB(F,F)-F | 19% |
| 3-H2BB(F,F)-F | 12% |
| 5-HHBB(F,F)-F | 5% |

| | |
|---|---|
| 5-HHEBB-F | 2% |
| 3-HH2BB(F,F)-F | 4% |
| 101-HBBH-4 | 4% |
| 101-HBBH-5 | 4% |

Compound (4-11-1) below was added to the composition described above at a proportion of 1% by weight.

Formula 78

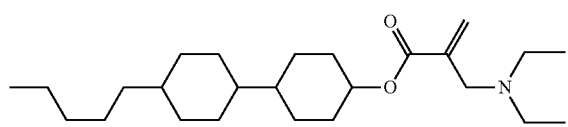

(4-11-1)

Compound (4-21-1) below was further added to the composition at a proportion of 2% by weight.

Formula 79

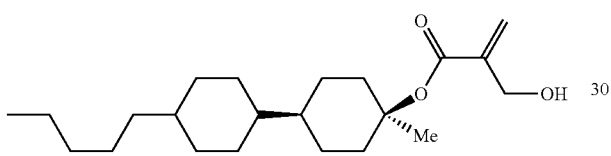

(4-21-1)

NI=102.2° C.; η=36.2 mPa·s; Δn=0.117; Δε=8.9.

Liquid Crystal Composition 14

| | |
|---|---|
| 5-HB-F | 12% |
| 6-HB-F | 9% |
| 7-HB-F | 7% |
| 2-HHB-OCF3 | 9% |
| 3-HHB-OCF3 | 5% |
| 4-HHB-OCF3 | 7% |
| 5-HHB-OCF3 | 7% |
| 3-HH2B-OCF3 | 5% |
| 5-HH2B-OCF3 | 4% |
| 3-HHB(F,F)-OCF2H | 5% |
| 3-HHB(F,F)-OCF3 | 3% |
| 3-HH2B(F)-F | 3% |
| 3-HBB(F)-F | 8% |
| 5-HBB(F)-F | 8% |
| 5-HBBH-3 | 5% |
| 3-HB(F)BH-3 | 3% |

Compound (4-22-1) below was added to the composition described above at a proportion of 1% by weight.

Formula 80

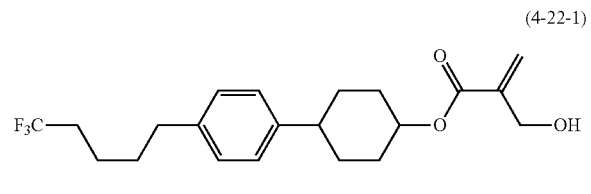

(4-22-1)

Compound (RM-2) below was further added to the composition at a proportion of 0.3% by weight.

Formula 81

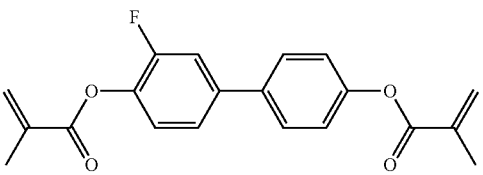

(RM-2)

NI=89.3° C.; η=14.8 mPa·s; Δn=0.092; Δε=4.2.

Liquid Crystal Composition 15

5-HB-CL 13%
3-HHB-1 7%
3-HHB (F, F)-F 8%
3-HBB (F, F)-F 20%
5-HBB (F, F)-F 16%
3-HHEB (F, F)-F 12%
4-HHEB (F, F)-F 5%
5-HHEB (F, F)-F 4%
2-HBEB (F, F)-F 4%
3-HBEB (F, F)-F 3%
5-HBEB (F, F)-F 3%
3-HBEB (F, F)-F 5%

Compound (3-1-2) below was added to the composition described above at a proportion of 2% by weight.

Formula 82

(3-1-2)

NI=80.5° C.; η=25.0 mPa·s; Δn=0.106; Δε=9.2.

Liquid Crystal Composition 16

| | |
|---|---|
| 3-HB-CL | 3% |
| 5-HB-CL | 5% |
| 3-HHB-OCF3 | 6% |
| 3-H2HB-OCF3 | 5% |
| 5-H4HB-OCF3 | 15% |
| V-HHB(F)-F | 6% |
| 3-HHB(F)-F | 5% |
| 5-HHB(F)-F | 6% |
| 3-H4HB(F,F)-CF3 | 8% |
| 5-H4HB(F,F)-CF3 | 10% |
| 5-H2HB(F,F)-F | 3% |
| 5-H4HB(F,F)-F | 7% |
| 2-H2BB(F)-F | 5% |
| 3-H2BB(F)-F | 10% |
| 3-HBEB(F,F)-F | 6% |

Compound (2-1-1) below was added to the composition described above at a proportion of 2% by weight.

Formula 83

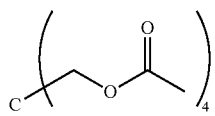

(2-1-1)

NI=72.8° C.; η=26.1 mPa·s; Δn=0.098; Δε=8.5.

Liquid Crystal Composition 17

| | |
|---|---|
| 5-HB-CL | 19% |
| 7-HB(F,F)-F | 5% |
| 3-HB-O2 | 17% |
| 3-HHB-1 | 12% |
| 3-HHB-O1 | 8% |
| 2-HHB(F)-F | 6% |
| 3-HHB(F)-F | 7% |
| 5-HHB(F)-F | 7% |
| 3-HHB(F,F)-F | 8% |
| 3-H2HB(F,F)-F | 6% |
| 4-H2HB(F,F)-F | 5% |

Compound (2-2-1) below was added to the composition described above at a proportion of 1% by weight.

Formula 84

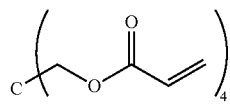
(2-2-1)

Compound (3-1-1) below was further added to the composition at a proportion of 1% by weight.

Formula 85

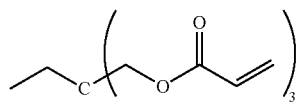
(3-1-1)

NI=73.0° C.; η=17.5 mPa·s; Δn=0.081; Δε=3.5.

Liquid Crystal Composition 18

| | |
|---|---|
| 5-HB-CL | 5% |
| 7-HB(F)-F | 7% |
| 3-HB-O2 | 16% |
| 3-HHEB-F | 10% |
| 5-HHEB-F | 10% |
| 3-HHEB(F,F)-F | 12% |
| 4-HHEB(F,F)-F | 7% |
| 3-GHB(F,F)-F | 6% |
| 4-GHB(F,F)-F | 8% |
| 5-GHB(F,F)-F | 8% |
| 2-HHB(F,F)-F | 5% |
| 3-HHB(F,F)-F | 6% |

Compound (4-11-1) below was added to the composition described above at a proportion of 1% by weight.

Formula 86

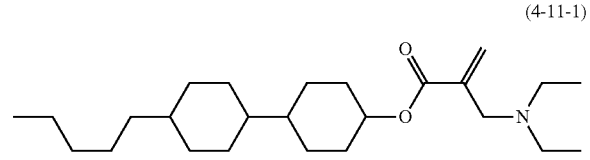
(4-11-1)

NI=70.4° C.; η=26.8 mPa·s; Δn=0.074; Δε=7.8.

Liquid Crystal Composition 19

| | |
|---|---|
| 1V2-BEB(F,F)-C | 15% |
| 3-HB-C | 20% |
| 2-BTB-1 | 13% |
| 3-HHB-1 | 7% |
| VFF-HHB-1 | 10% |
| VFF2-HHB-1 | 14% |
| 3-H2BTB-2 | 8% |
| 3-H2BTB-3 | 7% |
| 3-H2BTB-4 | 6% |

Compound (4-21-1) below was added to the composition described above at a proportion of 2% by weight.

Formula 87

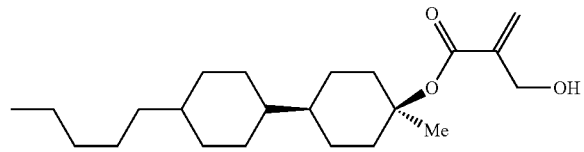
(4-21-1)

NI=94.1° C.; η=23.0 mPa·s; Δn=0.168; Δε=13.6.

Liquid Crystal Composition 20

| | |
|---|---|
| 3-HH-V | 36% |
| 3-HH-V1 | 9% |
| 3-BB(F)B(F,F)XB(F,F)-F | 2% |
| 4-BB(F)B(F,F)XB(F,F)-F | 10% |
| 5-BB(F)B(F,F)XB(F,F)-F | 9% |
| V2-HHB-1 | 11% |
| 3-HBBXB(F,F)-F | 7% |
| 4-GB(F)B(F,F)XB(F,F)-F | 6% |
| 5-GB(F)B(F,F)XB(F,F)-F | 5% |
| 3-GB(F,F)XB(F,F)-F | 5% |

Compound (2-2-1) below was added to the composition described above at a proportion of 2% by weight.

Formula 88

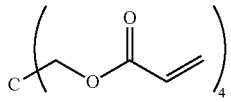
(2-2-1)

NI=86.7° C.; η=13.1 mPa·s; Δn=0.108; Δε=11.9.

Liquid Crystal Composition 21

| | |
|---|---|
| 3-HH-V | 23% |
| 3-HH-V1 | 5% |
| 2-HH-3 | 7% |
| 3-HB-O2 | 5% |
| 3-GB(F,F)XB(F,F)-F | 4% |
| 3-BB(F,F)XB(F,F)-F | 9% |
| 2-HHB-1 | 3% |
| 3-HHB-1 | 6% |
| 2-BB(F)B-3 | 4% |
| 3-HHB-O1 | 2% |
| 3-HHBB(F,F)-F | 4% |
| 4-HHBB(F,F)-F | 3% |
| 4-GB(F)B(F,F)XB(F,F)-F | 2% |
| 3-BB(F,F)XB(F)B(F,F)-F | 5% |
| V-HHB-1 | 14% |
| V2-HHB-1 | 4% |

Compound (4-11-1) below was added to the composition described above at a proportion of 1% by weight.

Formula 89

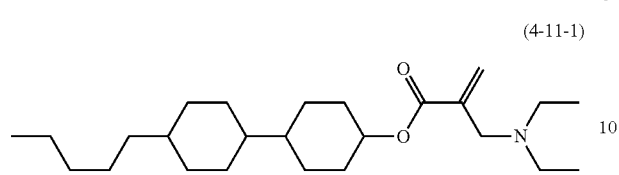

(4-11-1)

NI=91.2° C.; Δn=0.099; Δε=4.8.

Liquid Crystal Composition 22

| | |
|---|---|
| 3-HH-V | 35% |
| 3-HH-V1 | 5% |
| 1V2-HH-3 | 4% |
| 3-BB(F,F)XB(F,F)-F | 12% |
| V-HHB-1 | 14% |
| V2-HHB-1 | 10% |
| 2-BB(F)B-3 | 4% |
| 4-GB(F)B(F,F)XB(F,F)-F | 2% |
| 3-HBB(F,F)XB(F,F)-F | 5% |
| 3-HBBXB(F,F)-F | 9% |

Compound (3-1-2) below was added to the composition described above at a proportion of 3% by weight.

Formula 90

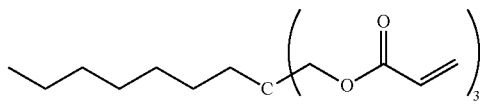

(3-1-2)

NI=90.5° C.; η=11.0 mPa·s; Δn=0.100; Δε=4.6.

Comparative Example 1

Liquid crystal composition (i) itself was applied as comparative liquid crystal composition (Cl) without adding a polar compound. When a cell was observed with regard to the liquid crystal composition by a polarizing microscope in the same manner as in Example 1, the cell was unable to be confirmed to be in homogeneous alignment.

For liquid crystal compositions (1) to (8), a used polar compound, a positive-phase negative-phase CV product thereof, a content (% by weight) in the liquid crystal composition, a total positive-phase negative-phase CV product, and a value obtained by dividing the total positive-phase negative-phase CV product by surface free energy of the substrate are shown below.

TABLE 3

| Liquid crystal composition | Polar compound | Positive-phase negative-phase CV product | Content | Total positive-phase negative-phase CV product | Total positive-phase negative-phase CV product / surface free energy Bare glass | ITO glass |
|---|---|---|---|---|---|---|
| 1 | (3-1-2) | 1.96 | 3 | 0.059 | 0.173 | 0.167 |
| 2 | (2-1-1) | 4.52 | 2 | 0.090 | 0.266 | 0.257 |
| 3 | (2-2-1) | 1.98 | 2 | 0.040 | 0.116 | 0.112 |
| 4 | (3-1-1) | 1.81 | 3 | 0.054 | 0.159 | 0.154 |

TABLE 3-continued

| Liquid crystal composition | Polar compound | Positive-phase negative-phase CV product | Content | Total positive-phase negative-phase CV product | Total positive-phase negative-phase CV product / surface free energy Bare glass | ITO glass |
|---|---|---|---|---|---|---|
| 5 | 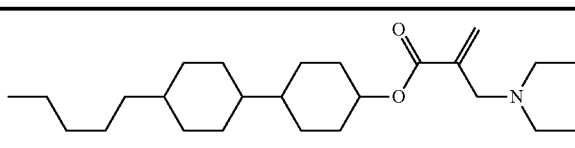 (4-11-1) | 3.12 | 1 | 0.031 | 0.092 | 0.089 |
| 7 | 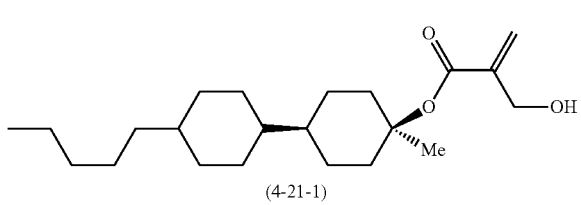 [SMILES: C=C(CO)C(=O)O[C@]1(C)CC[C@H](C2CCC(CCCCC)CC2)CC1] (4-21-1) | 3.66 | 3 | 0.110 | 0.323 | 0.312 |
| 8 | 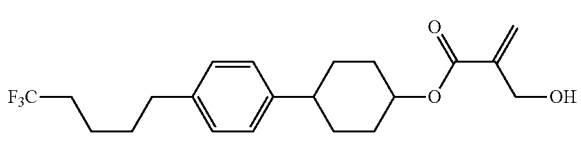 (4-22-1) | 3.06 | 1 | 0.031 | 0.090 | 0.087 |

The total positive-phase negative-phase CV product is the product (positive-phase negative-phase CV product×content/100) of the positive-phase negative-phase CV product of the polar compound and the content (% by weight) of the polar compound in the liquid crystal composition, which means, when plural kinds of the polar compounds are contained in the liquid crystal composition, a sum of respective total positive-phase negative-phase CV products of the polar compounds, and the sum of the positive-phase negative-phase CV products of the polar compounds existing in the liquid crystal composition. Moreover, surface free energy in the used bare glass and the used ITO patterning glass was 0.340 N/m and 0.352 N/m, respectively, and therefore the product was calculated by using respective values in the Table described above. The surface free energy on both substrates between which the liquid crystal compositions used in Examples 1 to 8 are interposed is substantially the same with each other, and therefore the ratio (total positive-phase negative-phase CV product/surface free energy) of the total positive-phase negative-phase CV product to the surface free energy on the substrate is specified in a narrow specific range as shown in Table 3.

The surface free energy on the substrate can be calculated from a contact angle of a liquid on the substrate by the Owens-Wendt method ordinarily used. Ordinarily, in measuring the surface free energy by using the contact angle of a liquid drop to be formed, at least two kinds of liquids are ordinarily used, and as the two kinds of liquids, use of a liquid having high polarity and a liquid having low polarity is already known to be preferable, and as the liquid having high polarity, water is used, and as the liquid having low polarity, diiodomethane is used. The liquid is gently added dropwise onto the substrate by using a pipe having an internal diameter of 0.05 to 0.3 millimeter and an outer diameter of 0.2 to 0.6 millimeter to form the liquid drop, and the liquid drop is recorded on a video, an advancing contact angle (contact angle when the liquid drop is formed) and a receding contact angle (contact angle when the liquid drop disappears) are measured, and the surface free energy is calculated based on the following expressions.

In a case where liquid 1 is added dropwise thereon, when a contact angle θ is 90 degrees or less, if a height of a liquid drop is taken as h, and a diameter of a contact circle of the liquid drop is taken as φ, or an expression: x=φ/2 holds, θ1 of the liquid is calculated according to the following expression (1-1).

$$\theta = 2\tan^{-1}(h/x) \quad \text{Expression (1-1)}$$

In the case where liquid 1 is added dropwise thereon, when the contact angle θ is 90 degrees or more, θ1 of the liquid is calculated according to the following expression (1-2).

$$\theta = 90 + \cos^{-1}(\varphi h/h2 + x2) \quad \text{Expression (1-2)}$$

In θ to be measured in this manner, from advancing θa and receding θr, θ1 of the liquid to a surface of a solid is determined according to the following expression.

$$\theta 1 = \cos^{-1}((\cos\theta a + \cos\theta r)/2)$$

Also for liquid 2, θ2 is calculated in a similar manner and substituted for expression (2-1) representing adhesion work to create two equations in which γsd (dispersion force component of surface free energy of solid) and γsp (polar force component of surface free energy of solid) are taken as unknown quantities, and γsd and γsp can be obtained by solving the simultaneous equations. Here, γ(liquid), γ(liquid)s and γ(liquid)p each are a characteristic value of the liquid and a known value.

$$\gamma(\text{liquid})(1+\cos\theta) = 2(\gamma sd \cdot \gamma(\text{liquid})d)^{1/2} + 2(\gamma sp \cdot \gamma(\text{liquid})p)^{1/2} \quad \text{Expression (2-1)}$$

Among γ, γsd and γsp, a relationship according to the following expression (2-2) exists, and therefore the surface free energy of the solid can be calculated by determining a sum of γsd and γsp determined.

$$\gamma = \gamma sd + \gamma sp \quad \text{Expression (2-2)}$$

Thus, if the contact angle is measured and the surface free energy on the substrate surface is measured by using the two kinds of liquids, the surface free energy can be measured with a small site difference and with good reproducibility.

Moreover, in the case of the substrate having significantly large surface free energy, the Owens-Wendt method may be occasionally hard to use, and therefore on the above occasion, the surface tension is calculated by the Dietzel equation, and the resulting value can be taken as the surface free energy. The Dietzel equation is shown below.

$$\gamma = M_1 F_1 + M_2 F_2 + \ldots + MiFi$$

γ: surface tension
Mi: mol % of i component, Fi: surface tension coefficient

In addition, the surface tension coefficient is a characteristic value of each component substance, and a known value.

The surface free energy γ of each substrate used in Examples 1 to 8 was calculated by using the Dietzel equation.

γ of bare glass=0.340 N/m
γ of ITO patterning glass=0.352 N/m

INDUSTRIAL APPLICABILITY

A technology capable of homogeneously aligning a liquid crystal medium by using an additive has not been found so far. According to preferred embodiments in the present application invention, the liquid crystal medium can be homogeneously aligned merely by adding a specific low molecular weight polar compound thereto, and a need for an alignment film or alignment treatment that has been applied so far can be eliminated. As a result, for example, a polyimide-less device can be achieved for a mode using a transverse electric field, such as an FFS mode.

What is claimed is:

1. A liquid crystal medium-sealed between a pair of substrates subjected to neither alignment treatment nor an alignment film and having a transparent electrode formed on at least one of the substrates, wherein the liquid crystal medium contains a low molecular weight polar compound for homogeneously aligning the liquid crystal medium relative to the substrate, so that the homogeneous alignment of the liquid crystal medium relative to the substrate occurs spontaneously, wherein the low molecular weight polar compound is represented by formula (2) or (3):

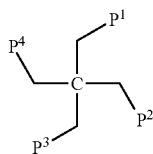

(2)

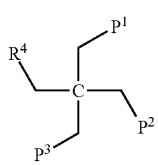

(3)

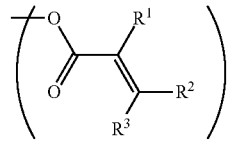

(Q-0)

wherein, in formulas (2) and (3), $R^4$ is hydrogen, halogen or alkyl having 1 to 20 carbons, and in $R^4$, at least one —$CH_2$— may be independently replaced by —O— or —S—, and at least one —$(CH_2)_2$— may be replaced by —CH=CH—, and in the groups, at least one hydrogen may be replaced by halogen, $P^1$, $P^2$, $P^3$ and $P^4$ are independently a group represented by formula (Q-0) or straight-chain, branched-chain or cyclic alkyl having 1 to 25 carbons, and in $P^1$, $P^2$, $P^3$ and $P^4$, at least one —$CH_2$— nonadjacent to each other may be independently replaced by —N(—$P^0$)—, —O—, —S—, —CO—, —CO—O—, —O—CO— or —O—CO—O— in such a manner that N, O and/or S atoms are not directly connected to each other, at least one tertiary carbon (CH group) may be replaced by N, at least one hydrogen may be independently replaced by F or Cl, and at least one —$(CH_2)_2$— may be independently replaced by —CH=CH— in which $P^1$, $P^2$, $P^3$ and $P^4$ contain one or more heteroatoms selected from N, S and/or O, and $P^0$ is independently straight-chain, branched-chain or cyclic alkyl having 1 to 25 carbons, and in $P^0$, at least one —$CH_2$— nonadjacent to each other may be independently replaced by —N(—$P^0$)—, —O—, —S—, —CO—, —CO—O—, —O—CO— or —O—CO—O— in such a manner that N, O and/or S atoms are not directly connected to each other, at least one tertiary carbon (CH group) may be replaced by N, at least one hydrogen may be independently replaced by F or Cl, and at least one —$(CH_2)_2$— may be independently replaced by —CH=CH— or —C≡C—, in which $P^0$ contains one or more heteroatoms selected from N, S and/or O, and in formula (Q-0), $R^1$, $R^2$ and $R^3$ are independently hydrogen, halogen or alkyl having 1 to 20 carbons, and in $R^1$, $R^2$ and $R^3$, at least one —$CH_2$— may be independently replaced by —O— or —S—, and at least one —$(CH_2)_2$— may be replaced by —CH=CH—, and in the groups, at least one hydrogen may be replaced by halogen.

2. The liquid crystal medium according to claim 1, wherein the low molecular weight compound has having a positive-phase negative-phase CV product of 1.3 or more.

3. A liquid crystal composition containing at least one low molecular weight polar compound represented by formula (2) or (3):

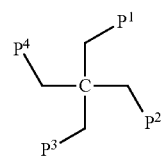

(2)

-continued

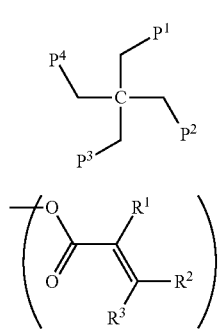
(3)

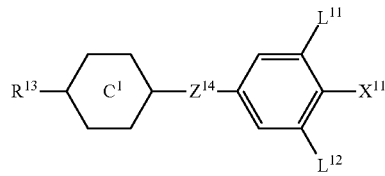
(Q-0)

wherein, in formulas (2) and (3),
R⁴ is hydrogen, halogen or alkyl having 1 to 20 carbons, and in R⁴, at least one —CH₂— may be independently replaced by —O— or —S—, and at least one —(CH₂)₂— may be replaced by —CH═CH—, and in the groups, at least one hydrogen may be replaced by halogen, P¹, P², P³ and P⁴ are independently a group represented by formula (Q-0) or straight-chain, branched-chain or cyclic alkyl having 1 to 25 carbons, and in P¹, P², P³ and P⁴, at least one —CH₂— nonadjacent to each other may be independently replaced by —N(—P⁰)—, —O—, —S—, —CO—, —CO—O—, —O—CO— or —O—CO—O— in such a manner that N, O and/or S atoms are not directly connected to each other, at least one tertiary carbon (CH group) may be replaced by N, at least one hydrogen may be independently replaced by F or Cl, and at least one —(CH₂)₂— may be independently replaced by —CH═CH— or —C≡C—, in which P¹, P², P³ and P⁴ contain one or more heteroatoms selected from N, S and/or O, and P⁰ is independently straight-chain, branched-chain or cyclic alkyl having 1 to 25 carbons, and in P⁰, at least one —CH₂— nonadjacent to each other may be independently replaced by —N(—P⁰)—, —O—, —S—, —CO—, —CO—O—, —O—CO— or —O—CO—O— in such a manner that N, O and of S atoms are not directly connected to each other, at least one tertiary carbon (CH group) may be replaced by N, at least one hydrogen may be independently replaced by F or Cl, and at least one —(CH₂)₂— may be independently replaced by —CH═CH— or —C≡C—, in which P⁰ contains one or more heteroatoms selected from N, S and/or O, and in formula (Q-0), R¹, R² and R³ are independently hydrogen, halogen or alkyl having 1 to 20 carbons, and in R¹, R² and R³, at least one —CH₂— may be independently replaced by —O— or —S—, and at least one —(CH₂)₂— may be replaced by —CH═CH—, and in the groups, at least one hydrogen may be replaced by halogen.

4. The liquid crystal composition according to claim 3, wherein a total positive-phase negative-phase CV product, which is a product of a positive-phase negative-phase CV product and a content of the low molecular weight polar compound, is 0.01 or more.

5. The liquid crystal composition according to claim 4, wherein a ratio of the total positive-phase negative-phase CV product to a surface free energy of the substrate is 0.025 to 1.

6. The liquid crystal composition according to claim 3, further containing at least one liquid crystal compound represented by any one of formulas (5) to (7):

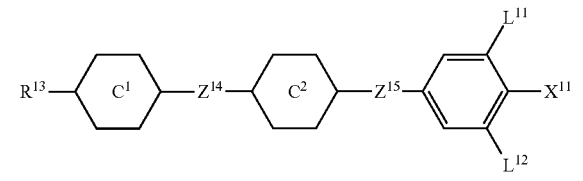
(5)

(6)

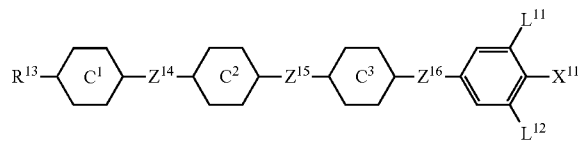
(7)

wherein, in formulas (5) to (7),
R¹³ is alkyl having 1 to 10 carbons or alkenyl having 2 to 10 carbons, and in R¹³, at least one —CH₂— may be replaced by —O—, and at least one hydrogen may be replaced by fluorine;

X¹¹ is fluorine, chlorine, —OCF₃, —OCHF₂, —CF₃, —CHF₂, —CH₂F, —OCF₂CHF₂ or —OCF₂CHFCF₃;

ring C¹, ring C² and ring C³ are independently 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;

Z¹⁴, and Z¹⁶ are independently a single bond, —(CH₂)₂—, —CH═CH—, —C≡C—, —COO—, —CF₂O—, —OCF₂—, —CH₂O— or —(CH₂)₄—; and L¹¹ and L¹² are independently hydrogen or fluorine.

7. The liquid crystal composition according to claim 3, further containing a liquid crystal compound represented by formula (8):

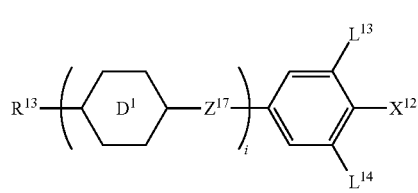
(8)

wherein, in formula (8),
R¹⁴ is alkyl having 1 to 10 carbons or alkenyl having 2 to 10 carbons, and in R¹⁴, at least one —CH₂— may be replaced by —O—, and at least one hydrogen may be replaced by fluorine;

X¹² is —C≡N or —C≡C—C≡N;

ring $D^1$ is 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;

$Z^{17}$ is a single bond, —(CH$_2$)$_2$—, —C≡C—, —COO—, —CF$_2$O—, —OCF$_2$— or —CH$_2$O—;

$L^{13}$ and $L^{14}$ are independently hydrogen or fluorine; and i is 1, 2, 3 or 4.

8. The liquid crystal composition according to claim 3, further containing at least one liquid crystal compound represented by any one of formulas (16) to (18):

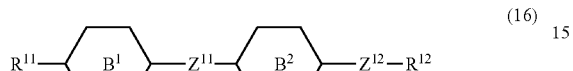

(16)

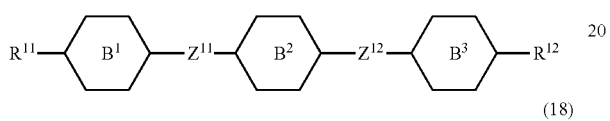

(17)

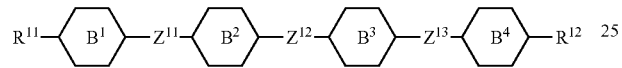

(18)

wherein, in formulas (16) to (18), $R^{11}$ and $R^{12}$ are independently alkyl having 1 to 10 carbons, alkoxy having 1 to 10 carbons, alkoxyalkyl having 2 to 10 carbons, alkenyl having 2 to 10 carbons or difluorovinyl;

ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and $Z^{11}$, $Z^{12}$ and $Z^{13}$ are independently a single bond, —(CH$_2$)$_2$—, —CH═CH—, —C≡C— or —COO—.

9. The liquid crystal composition according to claim 3, further containing a polymerizable compound represented by formula (19):

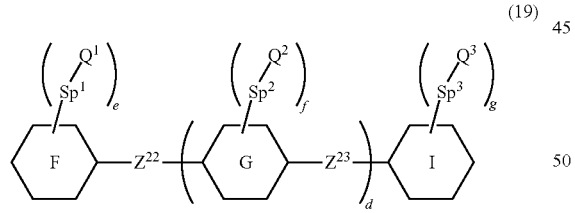

(19)

wherein, in formula (19), ring F and ring I are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one hydrogen may be independently replaced by halogen, alkyl having 1 to 12 carbons, alkoxy having 1 to 12 carbons, or alkyl having 1 to 12 carbons in which at least one hydrogen is replaced by halogen;

ring G is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one hydrogen may be independently replaced by halogen, alkyl having 1 to 12 carbons, alkoxy having 1 to 12 carbons, or alkyl having 1 to 12 carbons in which at least one hydrogen is replaced by halogen;

$Z^{22}$ and $Z^{23}$ are independently a single bond or alkylene having 1 to 10 carbons, and in $Z^{22}$ and $Z^{23}$, at least one —CH$_2$— may be independently replaced by —O—, —CO— or —COO—, and at least one —CH$_2$CH$_2$— may be independently replaced by —CH═CH—, —C(CH$_3$)═CH— or —C(CH$_3$)═C(CH$_3$)—, and in the groups, at least one hydrogen may be replaced by fluorine or chlorine;

$Q^1$, $Q^2$ and $Q^3$ are independently a polymerizable group;

$Sp^1$, $Sp^2$ and $Sp^3$ are independently a single bond or alkylene having 1 to 10 carbons, and in $Sp^1$, $Sp^2$ and $Sp^3$, at least one —CH$_2$— may be independently replaced by —O—, —COO—, —OCO— or —OCOO—, and at least one —CH$_2$CH$_2$— may be independently replaced by —CH═CH— or —C≡C—, and in the groups, at least one hydrogen may be independently replaced by fluorine or chlorine;

d is 0, 1 or 2; and e, f and g are independently 0, 1, 2, 3 or 4, and a sum of e, f and g is 1 or more.

10. The liquid crystal composition according to claim 9, wherein, in formula (19), $Q^1$, $Q^2$ and $Q^3$ are independently a polymerizable group represented by any one of formulas (Q-1) to (Q-5):

(Q-1)

(Q-2)

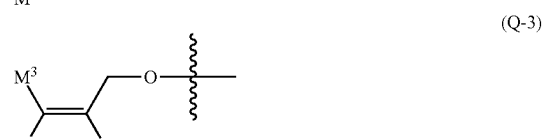

(Q-3)

(Q-4)

(Q-5)

wherein, in formulas (Q-1) to (Q-5), $M^1$, $M^2$ and $M^3$ are independently hydrogen, fluorine, alkyl having 1 to 5 carbons, or alkyl having 1 to 5 carbons in which at least one hydrogen is replaced by halogen.

11. The liquid crystal composition according to claim 9, wherein the polymerizable compound represented by formula (19) is a polymerizable compound represented by any one of formulas (19-1) to (19-7):

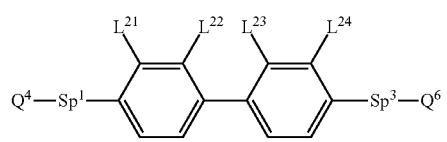
(19-1)

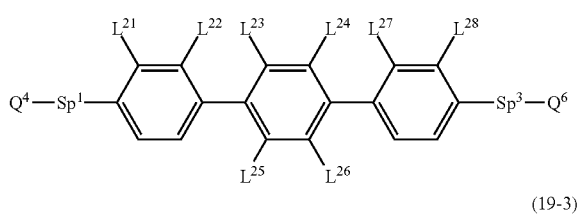
(19-2)

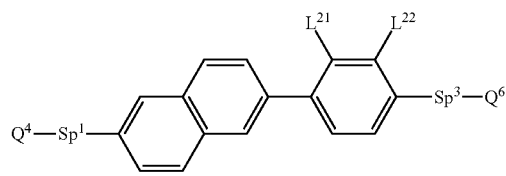
(19-3)

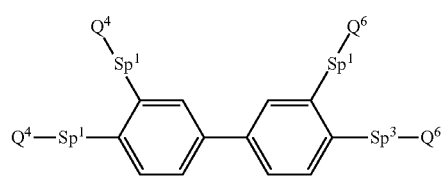
(19-4)

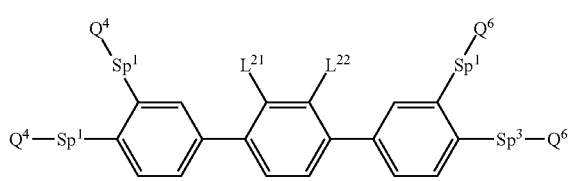
(19-5)

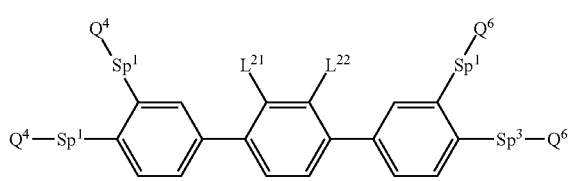
(19-6)

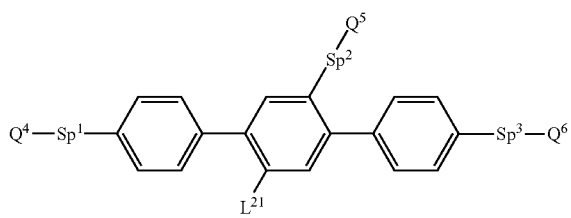
(19-7)

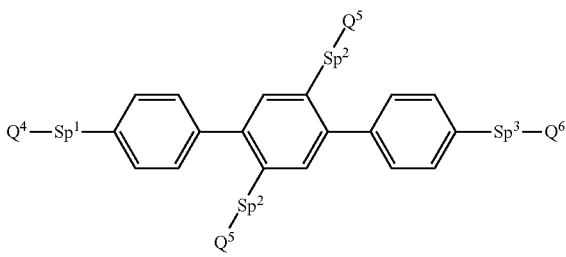

wherein, in formulas (19-1) to (19-7),
$L^{21}$, $L^{22}$, $L^{23}$, $L^{24}$, $L^{25}$, $L^{26}$, $L^{27}$ and $L^{28}$ are independently hydrogen, fluorine or methyl;
$Sp^1$, $Sp^2$ and $Sp^3$ are independently a single bond or alkylene having 1 to 10 carbons, and in $Sp^1$, $Sp^2$ and $Sp^3$, at least one —CH$_2$— may be independently replaced by —O—, —COO—, —OCO— or —OCOO—, and at least one —(CH$_2$)$_2$— may be independently replaced by —CH=CH— or —C≡C—, and in the groups, at least one hydrogen may be independently replaced by fluorine or chlorine; and
$Q^4$, $Q^5$ and $Q^6$ are independently a polymerizable group represented by any one of formulas (Q-1) to (Q-3), in which $M^1$, $M^2$ and $M^3$ are independently hydrogen, fluorine, alkyl having 1 to 5 carbons, or alkyl having 1 to 5 carbons in which at least one hydrogen is replaced by halogen:

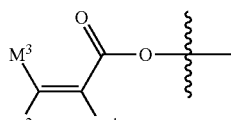
(Q-1)

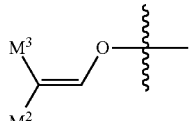
(Q-2)

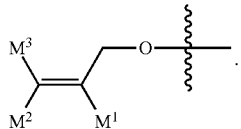
(Q-3)

12. The liquid crystal composition according to claim 3, further containing at least one selected from a polymerization initiator, a polymerization inhibitor, an optically active compound, an antioxidant, an ultraviolet light absorber, a light stabilizer, a heat stabilizer and an antifoaming agent.

* * * * *